US008889678B2

(12) United States Patent
Ruat et al.

(10) Patent No.: US 8,889,678 B2
(45) Date of Patent: Nov. 18, 2014

(54) ACYL GUANIDINE DERIVATIVES MODULATING THE HEDGEHOG PROTEIN SIGNALING PATHWAY

(75) Inventors: Martial Ruat, Orsay (FR); Hélène Faure, Gif-sur-Yvette (FR); Elisabeth Traiffort, Paris (FR); Hermine Roudaut, Marly-la-Ville (FR); André Mann, Ostwald (FR); Angèle Schoenfelder, Lampertheim (FR); Maurizio Taddei, Monteriggioni (IT); Fabrizio Manetti, Castelnuovo Berardenga (IT); Antonio Solinas, Siena (IT)

(73) Assignees: Centre National de la Recherche Scientifique, Paris (FR); Universite de Strasbourg, Strasbourg Cedex (FR)

( * ) Notice: Subject to any disclaimer, the term of this patent is extended or adjusted under 35 U.S.C. 154(b) by 0 days.

(21) Appl. No.: 13/386,782

(22) PCT Filed: Jul. 19, 2010

(86) PCT No.: PCT/FR2010/000516
§ 371 (c)(1),
(2), (4) Date: Apr. 5, 2012

(87) PCT Pub. No.: WO2011/010013
PCT Pub. Date: Jan. 27, 2011

(65) Prior Publication Data
US 2012/0196865 A1    Aug. 2, 2012

(30) Foreign Application Priority Data
Jul. 24, 2009   (FR) ...................... 09 03654

(51) Int. Cl.
| C07D 295/00 | (2006.01) |
| C07D 213/02 | (2006.01) |
| C07D 513/02 | (2006.01) |
| C07D 209/04 | (2006.01) |
| C07D 317/44 | (2006.01) |
| C07D 307/02 | (2006.01) |
| C07C 239/00 | (2006.01) |
| A61K 31/5377 | (2006.01) |
| A61K 31/44 | (2006.01) |
| A61K 31/429 | (2006.01) |
| A61K 31/404 | (2006.01) |
| A61K 31/357 | (2006.01) |
| A61K 31/34 | (2006.01) |
| A61K 31/16 | (2006.01) |
| C07D 209/08 | (2006.01) |
| A61K 31/155 | (2006.01) |
| C07D 317/68 | (2006.01) |
| C07D 213/56 | (2006.01) |
| C07C 279/22 | (2006.01) |
| C07D 513/04 | (2006.01) |
| C07D 307/68 | (2006.01) |
| C07D 209/14 | (2006.01) |
| C07D 295/155 | (2006.01) |
| C07D 213/81 | (2006.01) |

(52) U.S. Cl.
CPC ............ *C07C 279/22* (2013.01); *C07D 209/08* (2013.01); *A61K 31/155* (2013.01); *C07D 317/68* (2013.01); *C07D 213/56* (2013.01); *C07D 513/04* (2013.01); *C07D 307/68* (2013.01); *C07D 209/14* (2013.01); *C07D 295/155* (2013.01); *C07D 213/81* (2013.01); *C07C 2101/14* (2013.01)
USPC ........ 514/239.5; 514/354; 514/368; 514/415; 514/466; 514/471; 514/616; 544/165; 546/323; 548/155; 548/511; 549/436; 549/487; 564/157

(58) Field of Classification Search
USPC .............. 514/239.5, 354, 368, 415, 466, 471, 514/616; 544/165; 546/323; 548/155, 511; 549/436, 487; 564/157
See application file for complete search history.

(56) References Cited

U.S. PATENT DOCUMENTS

| 6,291,516 B1 | 9/2001 | Dudek et al. |
| 6,432,970 B2 | 8/2002 | Beachy et al. |
| 2005/0085519 A1 | 4/2005 | Rubin et al. |

FOREIGN PATENT DOCUMENTS

| EP | 0 003 640 A2 | 6/1979 |
| FR | 2 850 022 A1 | 7/2004 |
| WO | WO 99/52534 A1 | 10/1999 |
| WO | WO 00/41545 A2 | 7/2000 |
| WO | WO 01/19800 A2 | 3/2001 |
| WO | WO 01/26644 A2 | 4/2001 |
| WO | WO 01/27135 A2 | 4/2001 |
| WO | WO 01/74344 A2 | 10/2001 |
| WO | WO 01/98344 A2 | 12/2001 |

(Continued)

OTHER PUBLICATIONS

Iwanowicz, Edwin J. Novel Guanidine-Based Inhibitors of Inosine Monophosphate Dehydrogenase. Bioorganic & Medicinal Chemistry Letters. 12 (2002) 2931-2934.*

Angot, Elodie, et al.; "Chemoattactrive Activity of Sonic Hedgehog in the Adult Subventrocular Zone Modulates the Number of Neural Precursors Reaching the Olfactory Bulb"; Stems Sells, The Stem Cell Niche; Downloaded from www.StemCells.com at CNRS Inst De Neurobiolg Alfred F on Oct. 3, 2008.

(Continued)

*Primary Examiner* — Samantha Shterengarts
(74) *Attorney, Agent, or Firm* — Alston & Bird LLP

(57) ABSTRACT

The present invention relates to acyl guanidine derivatives modulating the hedgehog protein signaling pathway to be used as drugs, in particular for treating diseases involving a tissue dysfunction associated with a deregulation of the hedgehog protein signaling pathway, as well as to pharmaceutical compositions containing same. The present invention also relates to novel acyl guanidine derivatives as such.

27 Claims, 5 Drawing Sheets

(56) References Cited

FOREIGN PATENT DOCUMENTS

| WO | WO 02/30421 A2 | 4/2002 |
|---|---|---|
| WO | WO 02/30462 A2 | 4/2002 |
| WO | WO 2006/028958 A2 | 3/2006 |
| WO | WO 2006/050506 A1 | 5/2006 |
| WO | WO 2007/059157 A1 | 5/2007 |

OTHER PUBLICATIONS

Borzillo, GV, et al.; "The Hedgehog Signaling Pathway as a Target for Anticancer Drug Discovery"; Cancer Biology, Pfizer Global Research and Development, Groton Laboratories, Eastern Point Road, Groton, CT 06340 USA; Curr Top Med Chem; 2005.

Charytoniuk, D, et al.; "Intrastiatal Sonic Hedgehog Injection Increases Patched Transcript Levels in Adult Rat Subventricular Zone"; European Journal of Neuroscience, vol. 16, pp. 2351-2357, 2002.

Chen, James K., et al; "Small Molecule Modulation of Smoothhead Activity"; PNAS, vol. 99, No. 22, pp. 14071-14076; Oct. 29, 2002.

Frank-Kamenetsky, Maria, et al.; "Small-Molecule Modulators of Hedgehog Signaling: Identification and Characterization of Smoothened Agonists and Antagonists"; Journal of Biology; 2002, vol. 1, Issue 2, Article 10.

Loulier, Karine, et al.; "Increase of Proliferating Oligodendroglial Progenitors in the Adult Mouse Brain Upon Sonic Hedgehog Delivery in the Lateral Ventricle"; Journal of Neurochemistry, 2006, 98, 530-542.

Mahindroo, Neeraj, et al.; "Hedgehog-Gli Signaling Pathway Inhibitors as Anticancer Agents", American Chemical Society, Publication Date (Web) Mar. 23, 2009.

Yang, Hongbo, et al.; "Converse Conformational Control of Smoothened Activity by Structurally Related Small Molecules", Copyright 2009 by The American Society for Biochemistry and Molecular Biology, Inc.

International Search Report and Written Opinion for International Application No. PCT/FR2010/000516, mailed Sep. 24, 2010.

Aggarwal et al., Synth. Comm., 2006, 36, 875.

Ahn and Joyner, Nature, 2005, 437, 894-897.

Angot et al., 2008.

Berman et al., Science, 2002, 297, 1559-1561.

Borzillo et al., Curr. Top Med. Chem., 2005, 5(2), 147-57.

Burkholder et al., Tetrahedron Lett., 2001, 42, 3077.

Charytoniuk et al., 2002.

Charytoniuk et al., Eur. J. Neurosci., 2002, 16, 2351-2357.

Charytoniuk et al., J. Physiol. Paris, 2002, 96, 9-16.

Chen et al., Genes Dev., 2002, 16(21), 2743-2748.

Chen et al. (Proc. Natl. Acad. Sci. USA, 2002, 99, 14071.

Curis and Chen et al., PNAS, 2002, 99, 14071-14076.

Curis and Kamenetsky et al., J. Biol., 2002, 1, 1-19.

Dahmane et al., Development, 1999, 126, 3089-3100.

Frank-Kamenetsky et al., J. Biol., 2002, 1, 10.

Goodrich et al., Science, 1997, 277, 1109-1113.

Ho et al., Curr. Opin. Neurobiol., 2002, 12, 57-63.

Indardona et al., Development, 1998, 125, 3553.

Ingham, P.W.; "Hedgehog signaling in animal development: paradigms and principles"; Genes Dev.; vol. 15; Issue 23; Dec. 2001; pp. 3059-3087.

Loulier et al., 2006.

Ma et al., Cell, 2002, 111, 63-75.

Mahindroo et al., J. Med. Chem. 2009, 52, 3829-3845.

Marti, E., et al., "Sonic hedgehog in CNS development: one signal, multiple outputs"; Trends in Neurosciences; vol. 25; Issue 2; Feb. 2002; pp. 89-96.

Miller-Moslin et al., J. Med. Chem., 2009, 52, 3954-3968.

Georges Paxinos, Keith B. J., Franklin, 2nd edition, 2001, Academic Press (San Diego, United States).

Pepinsky et al. (J. Biol. Chem., 1998, 273, 14037.

Pepinski et al., J. Pharm. Sci., 2002, 91, 371-387.

Pierron, P.; "Mode de Preparation des Acylguanidines Aromatiques"; Compte Rendus Des Seances De L'Academie Des Sciences; vol. 151; 1911; pp. 1364-1366; XP008119681.

Rasmussen et al., Synthesis, 1988, 456-459.

Reilly et al., Mol. Cell. Neurosci., 2002, 19, 88-96.

Shirada et al., Tetrahedron Lett., 2006, 47, 1945.

Taipale et al., Nature, 2001, 411, 349-354.

Talpale et al., Nature, 2000, 406, 1005-1009.

Taipale et al., Nature, 2002, 418, 892-896.

Traiffort et al., Eur. J. Neursci, 1999, 11, 3199-3214.

Tsuboi et al., Exp. Neurol., 2002, 173, 95-104.

Wallace et al., Curr. Biol., 1999, 22, 103-114.

Weshler-Reya et al., Neuron., 1999, 22, 103-114.

Weschler-Reya, R, et al.; "The Develpmental Biology of Brain Tumors"; Annual Reviews Neuroscience; vol. 24; 2001; pp. 385-428.

Xie et al., Nature, 1998, 391, 90-92.

Yang et al., Angew. Chem. Int., Ed. 2008, 47, 1473

Yang et al., The Journal of Biological Chemistry, published on Apr. 14, 2009.

Zhang et al., J. Org. Chem., 2005, 70, 5164.

Aggarwal et al. Synth. Comm., 2006, 36, 875.

Burkholder et al. Tetrahedron Lett., 2001, 42, 3077.

Chen, J.K. et al., *Inhibition of Hedgehog signaling by direct binding of cyclopamine to smoothened*, Genes & Dev., vol. 16 (2002) pp. 2743-2748.

Dahmane, N. et al., *Sonic Hedgehog Regulates the Growth and Patterning of the Cerebellum*, Development, vol. 126 (1999) pp. 3089-3100.

Goodrich, L.V. et al., *Altered Neural Cell Fates and Medulloblastoma in Mouse patched Mutants*, Science, vol. 277 (1997) pp. 1109-1113.

Ho, K.S. et al.., *Sonic Hedgehog in the Nervous System: Functions, Modifications and Mechanisms*, Current Opinion in Neurobiology, Vo. 12 (2002) pp. 57-63.

Incardona, J.P. et al., *The Teratogenic Veratrum Alkaloid Cyclopamine Inhibits Sonic Hedgehog Signal Transduction*, Development, vol. 125 (1998) pp. 3553-3562.

Ingham, P.W. et al., *Hedgehog Signaling in Animal Development: Paradigms and Principles*, Genes Dev., vol. 15, (2001) pp. 3059-3087.

Ma, Y. et al., *Hedgehog-Mediated Patterning of the Mammalian Embryo Requires Transporter-like Function of Dispatched*, Cell, vol. 111 (2002) pp. 63-75.

Marti, E. et al., *Sonic Hedgehog in CNS Development: One Signal, Multiple Outputs*, Trends in Neurosciences, vol. 25, No. 2, (2002) pp. 89-96.

Miller-Moslin, K. et al., *1-Amino-4-Benzylphthazines as Orally Bioavailable Smoothened Antagonists with Antitumor Activity*, J. Med. Chem., vol. 52 (2009) pp. 3954-3968.

Pepinsky, R.B. et al., *Identification of a Palmitic Acid-modified Form of Human Sonic Hedgehog*, The Journal of Biological Chemistry, vol. 279, No. 22(1998) pp. 14037-14045.

Pepinsky, R.B. et al., *Long-acting Forms of Sonic Hedgehog with Improved Pharmacokinetic and Pharmacodynamic Properties are Efficacious in a Nerve Injury Model*, Pharm Sci. vol. 91, No. 2, (2002) pp. 371-387.

Pierron, P. *Mode de Preparation des Acylguanidines Aromatiques*, Compte rendus des Seances de l'Academie des Sciences, vol. 151, pp. 1364-1366.

Ott Reilly, J. et al., *Cooperative Effects of Sonic Hedgehog and NGF on Basal forebrain and Cholinergic Neurons*, Molecular Cellular Neuroscience, vol. 19 (2002) pp. 88-96.

Taipale, J. et al., *The Hedgehog and Wnt Signalling Pathways in Cancer*, Nature, vol. 411 (2001) pp. 349-354.

Taipale, J. et al., *Effects of Oncogenic Mutations in Smoothened and Patched can be Reversed by Cyclopamine*, Nature, vol. 406 (2000) pp. 1005-1009.

Tailpale, J. et al., *Patched Acts Catalytically to Suppress the Activity of Smoothened*, Nature, vol. 418 (2002) pp. 892-445.

(56) References Cited

OTHER PUBLICATIONS

Traiffort, E. et al., *Discrete Localizations of Hedgehog Signalling Components in the Developing and Adult Rat Nervous System*, European Journal of Neuroscience, vol. 11 (1999) pp. 3199-3214.
Traiffort, E. et al., *High Expression and Anterograde Axonal Transport of Aminoterminal Sonic Hedgehog in the Adult Hamster Brain*, European Journal of Neuroscience, vol. 14 (2001) pp. 839-850.
Tsuboi, K. et al.,*Intrastriatal Injection of Sonic Hedgehog Reduces Behavioral Impairmetn in a Rat Model of Parkinson's Disease*, Experimental Neurology, vol. 173 (2002) pp. 95-104.
Wechsler-Rena, R.J. et al., *Control of Neuronal Precursor Proliferation in the Cerebellum by Sonic Hedgehog*, Neuron, vol. 22 (1999) pp. 103-114.
Wechsler-Reya, R. et al., *The Developmental Biology of Brain Tumors*, Annu. Rev. Neurosci., vol. 24 (2001) pp. 385-428.
Xie, J. et al., *Activating Smoothened Mutations in Sporadic Basal-Cell Carcinoma*, Nature, vol. 391 (1998) pp. 90-92.
Zhang, H. et al., *Amino Acid Promoted CuI-Catalyzed C-N Bond Formation between Aryl Halides and Amines or N-Containing Heterocycles*, J. Org. Chem., vol. 70 (2005) pp. 5164-5173.

* cited by examiner

ACYL GUANIDINE DERIVATIVES MODULATING THE HEDGEHOG PROTEIN SIGNALING PATHWAY

FIELD OF THE INVENTION

The present invention relates to acyl guanidine derivatives modulating the Hedgehog protein signaling pathway used as medicaments, in particular for treating pathological conditions involving a tissue dysfunction linked to a dysregulation of the Hedgehog protein signaling pathway, and also to the pharmaceutical compositions containing same. The present invention also relates to novel acyl guanidine derivatives as such.

BACKGROUND OF THE INVENTION

The Hedgehog (Hh) signaling molecule is a secreted autoproteolytic protein that activates the Hedgehog protein signaling pathway, which is a signaling pathway that plays a fundamental role in the morphogenesis of many tissues, in particular in the formation of the endoderm and of the embryonic axis, the development of the brain and hair follicles, and also in cell proliferation, and appears to be involved in tissue maintenance and repair in adults (Ingham et al., Genes Dev., 2001, 15, 3059-3087; Marti et al., Trends Neurosci., 2002, 25, 89-96; Weschler et al., Annu. Rev. Neurosci., 2001, 24, 385-428).

The Hedgehog protein and the associated transduction pathway, initially demonstrated in *drosophila*, are conserved in vertebrates and invertebrates. A single homolog of Hh is present in *drosophila*, while three homologs of Hh: Sonic (Shh), Indian (Ihh) and Desert (Dhh) are present in mammals. Among these three homologs, Shh has been the most widely studied owing to its extended expression profile during development. Shh participates in neural tube ventralization by specifying the early phenotype of several types of neurons along the ventral median line (spinal cord motoneurons, dopaminergic or cholinergic neurons) and by inducing the generation of oligodendrocyte precursors from the ventral spinal cord. Moreover, Shh induces survival of gabaergic and dopaminergic neurons, orientates the fate of serotoninergic precursors and prevents dopaminergic neuron death caused by the toxin MPP. Finally, it induces granular cell precursor proliferation in the early post-natal cerebelum. The other members of the Hedgehog family participate, for their part, respectively in the development of bone tissue (Ihh), the testicles and the peripheral nerves (Dhh). In addition, the results obtained with Shh are also applicable to Dhh and Ihh.

The regulatory role of the Hedgehog protein signaling pathway during embryonic development has been widely studied: Hh has been associated with maintenance and repair processes in normal tissue, and in the spatiotemporal regulation of proliferation and differentiation, thus allowing developing tissues to reach their correct size with the appropriate cell types and appropriate degrees of vascularization and innvervation. The essential role of the Hh signaling function is demonstrated by the dramatic consequences of defects in this signaling pathway in the human fetus, such as holoprosencephaly observed in Shh mutants.

More recently, the Shh pathway has been identified in the adult brain, where the amino-terminal active form of the molecule is expressed in many regions of the mature nervous system at a higher level than that encountered during the early post-natal period (Traiffort et al., Eur. J. Neurosci., 1999, 11, 3199-3214 et 2001, 14, 839-850). Although the roles of Shh in adults have not been completely elucidated, it first appeared, like other neutrotrophic molecules, to be a factor capable of promoting survival and maintenance of the phenotype of cells of the nervous system (Reilly et al., Mol. Cell. Neurosci., 2002, 19, 88-96; Charytoniuk et al., Eur. J. Neurosci., 2002, 16, 2351-2357). Under pathological conditions, such as a model for Parkinson's disease or a model for peripheral neuropathy, Shh is capable of preserving axonal projections of dopaminergic neurons in the striatum or of improving the time required for motor recovering subsequent to crushing of the sciatic nerve (Tsuboi et al., Exp. Neurol., 2002, 173, 95-104; Pepinski et al., J. Pharm. Sci., 2002, 91, 371-387).

Hh proteins are synthesized in the form of immature precursors of approximately 45 kDa which undergo intramolecular cleavage catalyzed by the C-terminal region of the precursor. This cleavage produces a 25 kDa C-terminal fragment with no known additional function and a 19 kDa active amino-terminal fragment (called HhNp for N-terminal processed domain) linked at its C-terminal end to a cholesterol molecule, sufficient for all the known signaling activities of Hedgehog proteins.

The Hedgehog protein signaling pathway comprises three main components; the Hh ligand, a transmembrane receptor circuit composed of the Patched (Ptc) negative regulator and the Smoothened (Smo) activator, and a cytoplasmic complex which regulates the transcriptional effectors.

The cellular response to the Hedgehog morphogen is controlled by the expression products of the Patched (Ptc) gene, which is a tumor suppressor gene, and of the Smoothened (Smo) protooncogene; however, the exact mechanism for Hedgehog pathway regulation has not been completely elucidated. In mammals, there are two Patched genes encoding respectively Ptc1 and Ptc2, glycoproteins with 12 transmembrane domains which are homologous to bacterial transporters. The product of the Smo gene which encodes a protein of the G protein-coupled receptor family has no known endogenous ligand. In the absence of Hedgehog proteins, Ptc appears to block the constitutive activity of Smo. The binding of Hedgehog to Ptc appears to lift this inhibition and to allow signal transduction by means of Smo. The mechanism for regulating the activity of Smo by Ptc, in mammals, could involve a molecule transported by Ptc and interacting with Smo (Taipale et al., Nature, 2002, 418, 892-896). The activation of Gli transcription factors is involved in the cascade of events resulting from the activity of Smo. The type I transmembrane protein, HIP (Hedgehog Interacting Protein), constitutes another receptor for Hedgehog molecules which it binds with an affinity comparable to that of Ptc; HIP has been proposed as a negative regulator of the pathway (Ingham et al., mentioned above; Ho et al., Curr. Opin. Neurobiol., 2002, 12, 57-63; Taipale et al., Nature, 2001, 411, 349-354). In addition, the products of the dispatched (Disp) gene, in particular DispA, appear to be involved in the release of Hedgehog proteins in the soluble form into the extracellular medium and the accumulation thereof in said medium (Ma et al., Cell, 2002, 111, 63-75).

Shh signaling pathway dysfunctions have been associated with numerous cancers, in particular following the characterization of Ptc as a tumor suppressor gene. Indeed, inactivating mutations of Ptc are associated with Gorlin syndrome or basal cell nevus syndrome, an autosomal dominant disease characterized by cranofacial and cerebral malformations, particularly by a high incidence of various tumors, more particularly basal cell carcinomas of the skin and medulloblastomas in the brain. Mice heterozygous for the Ptc gene develop cerebellar tumors, suggesting that a modification of the Shh pathway is responsible for these tumors (Goodrich et al., Science, 1997, 277, 1109-1113).

Mutations of human Ptc or Smo genes are also observed in primitive neuroectodermal tumors of the central nervous system, mainly medulloblastomas (30% of cases), but also in sporadic forms of basal cell carcinomas (respectively 40% to 20% of cases for Ptc and Smo). In addition, mutations in Shh (H133Y) are also associated with basal cell carcinomas. Smo mutations, which mainly involve two amino acids located in the seventh hydrophobic domain of the receptor (W535L and S533N), induce constitutive activation of the pathway which escapes the negative control of Ptc. In contrast, those of Ptc result in a reduction in the inhibition exerted thereby on Smo in the absence of Shh. In the two cases, activation of the Shh pathway results therefrom and leads to a powerful mitogenic activity demonstrated in cultures of precursors of granular cells of the developing cerebellum, and to blocking of the terminal step of differentiation of these neuroblasts (Traiffort et al., Eur. J; Neurosci., 1999, mentioned above; Charytoniuk et al., J. Physiol. Paris, 2002, 96, 9-16; Dahmane et al., Development, 1999, 126, 3089-3100; Wallace et al., Curr. Biol., 1999, 22, 103-114; Weshler-Reya et al., Neuron., 1999, 22, 103-114). Likewise, the expression of Smo carrying one of these mutations in transgenic mice results in the presence of basal cell carcinomas, thereby demonstrating the direct involvement of Smo in the development of these tumors (Xie et al., Nature, 1998, 391, 90-92).

Apart from basal cell carcinomas and medulloblastomas, other types of tumors have been associated with a defect in the Hedgehog signaling pathway; the location of these tumors is closely correlated with the sites of expression of the components of the pathway during embryonic development. By way of nonlimiting example, mention may be made of: breast cancers and meningiomas associated with Ptc mutations, glioblastomas associated with Gli mutations, gastrointestinal cancers, in particular primary cancers of the stomach, prostate cancers, ovarian fibromas and dermoids, rhabdomyosarcomas, small cell lung cancers, an oral squamous cell carcinomas. Recently, Shh has been associated with psoriasis.

Because of the essential role of the Hedgehog protein signaling pathway in numerous physiological processes and consequently of the significance of the pathological conditions linked to the dysfunction thereof, the components of this pathway, such as the Smoothened and Patched (Patched 1 and Patched 2) proteins, the Dispatched (Dispatched 1 and Dispatched 2) proteins or else the HIP protein, represent targets for developing novel molecules capable of modulating (activating or inhibiting) this pathway and thus upregulating or downregulating the development [proliferation, differentiation, migration, survival (apoptosis)] and/or the activity of differentiated cells and stem cells, in vitro and/or in vivo, in embryos or in adults.

Such molecules are of use in the treatment of tumors associated with hyperactivation of the Hedgehog pathway: nervous tissue tumors (medulloblastomas, primative neuroectodermal tumors, glioblastomas, meningiomas and oligodendrogliomas), skin tumors (basal cell carcinomas, trichoepitheliomas), muscle and bone tissue tumors (rhabdomyosarcomas, osteosarcomas) and tumors of other tissues (kidney, bladder).

Such molecules are also of use in the treatment of neurodegenerative pathological conditions requiring blocking of the Hedgehog pathway (Parkinson's disease, Huntington's chorea, Alzheimer's disease, multiple sclerosis, motoneuron disease), and diseases in which blocking of the Hedgehog signaling pathway could be beneficial, such as diabetes.

Such molecules are also of use in the medical or surgical treatment (plastic or reconstructive surgery, tissue or organ transplantation) of numerous acute, subacute or chronic, genetic or acquired pathological conditions—involving a tissue dysfunction linked to disregulation of the Hedgehog pathway—, for inducing the formation, regeneration, repair and/or increase in activity of tissues such as, in a nonlimiting manner: nerve tissue [central nervous system (brain) and peripheral nervous system (sensory neurons, motor neurons, sympathetic neurons)], bone, cartilage, testicles, liver, spleen, intestine, pancreas, kidneys, smooth and skeletal muscles, heart, lungs, skin and hair system, mucous membranes, blood cells and cells of the immune system. By way of nonlimiting example of these pathological conditions, mention may in particular be made of neuropathies and associated neuromuscular diseases, diabetes, alopecia, burns, ulcers (skin and mucous membranes) and problems with spermatogenesis.

Various molecules, capable of modulating the activity of the Hedgehog pathway, have been identified:

Hedgehog proteins and derived polypeptides (fragments, variants, etc.), in particular Hedgehog protein agonists and antagonists (PCT International Application WO 01/98344 in the name of Biogen); owing to their size, these proteins and the derived polypeptides cannot cross the blood-brain barrier and cannot therefore be administered systemically, in particular for the treatment of brain tumors linked to hyperactivation of the Hedgehog protein signaling pathway. In addition, such molecules are not very stable and are difficult to produce and to purify;

heterocyclic organic molecules (PCT International Application WO 01/74344 in the name of Curis and Chen et al., PNAS, 2002, 99, 14071-14076);

nitrogenous heterocyclic molecules (PCT International Applications WO 01/19800, WO 01/26644 and WO 02/30421 in the name of Curis and Kamenetsky et al., J. Biol., 2002, 1, 1-19); and plant steroids derived from *Veratrum* spp (jervine, cyclopamine and cycloposine) and from *Solanum* spp. (solanidine), substituted in position 16, 17 or 18 with an amine or an amine derivative, and cholesterol: U.S. Pat. No. 6,432,970 and PCT International Applications WO 99/52534 and WO 01/27135 in the name of Johns Hopkins University School of Medicine; U.S. Pat. No. 6,291, 516; PCT International Application WO 00/41545 in the name of Ontogeny Inc.; PCT International Application WO 02/30462 in the name of Curis; Talpale et al., Nature, 2000, 406, 1005-1009; Berman et al., Science, 2002, 297, 1559-1561). However, cyclopamine is a teratogenic agent responsible for holoprosencephaly and cyclopia in the embryo in mammals, and it has also been demonstrated that cyclopamine concentrations above 10 µM prove to be cytotoxic for cells (Borzillo et al., Curr. Top Med. Chem., 2005, 5(2), 147-57). With regard to the other compounds derived from plant steroids, the absence of toxicity thereof in mammals has not yet been demonstrated;

mifepristone (17β-hydroxy-11β-(4-dimethylaminophenyl)-17α-(prop-1-ynyl)estra-4,9-dien 3-one), also called RU-486 or RU-38486 (French patent FR 2 850 022 in the name of CNRS), for which an inhibitory activity of the activity of the Hedgehog protein signaling pathway has been demonstrated;

urea or thiourea derivatives which are antagonists of the Hedgehog protein signaling pathway have also been described in application US 2005/0085519 A1.

The molecules SANT74 and SANT75 which have a structure analogous to that of SAG, a synthetic activator compound of chlorobenzothiophene type (CAS No.: 364590-63-6) corresponding to the following formula:

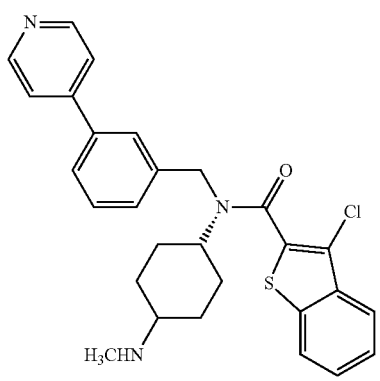

are also known to be stable inhibitors which make it possible to effectively control the conformation of the Smo activator (Yang et al., The Journal of Biological Chemistry, published on Apr. 14, 2009).

Other compounds inhibiting the Hedgehog signaling pathway have also been described recently: pyridyl-based inhibitors (PCT International Application WO 2006/028958 in the name of Genentech Inc. and Curis Inc.) and bisamide-based inhibitors (PCT International Application WO 2007/059157 in the name of Genentech Inc. and Curis Inc.).

Other molecules which act in particular on the transcription factors of the Gli family have also been described (Mahindroo et al., J. Med. Chem. 2009, 52, 3829-3845).

It follows from the aforementioned that there is currently no molecule which makes it possible to modulate the activity of the Hedgehog protein signaling pathway and for which an absence of toxicity has been established by means of clinical trials in humans.

SUMMARY OF THE INVENTION

Consequently, the inventors gave themselves the aim of providing novel compounds which modulate (stimulate or inhibit) the Hedgehog protein signaling pathway and which more successfully meet the practical needs, in particular in that they are simple to synthesize and can potentially be used in human therapy.

This objective is achieved through the compounds of formula (I) which are described hereinafter and which constitute the first subject matter of the invention insofar as these molecules have the advantage of comprising a main function of acyl guanidine type which is obtained from readily available raw materials. The guanidine function, as a base, can be salified, which has the advantage of producing compounds having good solubility in an aqueous medium. All of the compounds of formula (I) are obtained very conveniently using simple chemical reactions well known to those skilled in the art.

Consequently, the subject of the present invention is the compounds of formula (I) below:

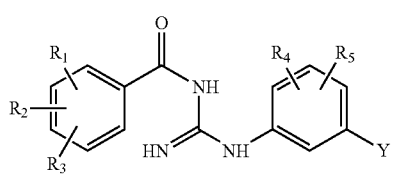

(I)

in which:

$R_1$, $R_2$ and $R_3$, which may be identical or different, and independently of one another, represent a hydrogen or halogen atom, a hydroxyl radical, an alkyl group, a perfluoroalkyl group, an optionally substituted alkoxy group, an alkylthio group, a nitrile group, or a fused heterocycle obtained from two of $R_1$, $R_2$ and $R_3$ which are fused with two adjacent carbon atoms of the phenyl ring to which they are bonded, the phenyl ring with said fused heterocycle preferably representing a benzodioxole, an oxindole, a benzoxazolone or a quinoline;

Y represents a monocyclic or polycyclic heteroaryl group, —NH—(C=O)—$R_6$, —(C=O)—NH—$R_6$ or —NH—(C=O)—NH—$R_6$, in which $R_6$ represents an unsubstituted monocyclic or polycyclic aryl group; an aryl group comprising one or more substituents chosen from a halogen atom, an alkyl, alkoxy or alkoxyaryl, monoalkylamino or dialkylamino radical, an aryl or heteroaryl group, a heterocycle; a monocyclic or polycyclic heteroaryl group; a linear or branched alkyl radical; a saturated or unsaturated, monocyclic or polycyclic hydrocarbon-based group;

$R_4$ and $R_5$, which may be identical or different, and independently of one another, represent a hydrogen or halogen atom, or an alkoxy, alkylthio, alkyl, perfluoroalkyl, nitrile or nitro group, as medicaments.

As is demonstrated in the examples which illustrate the present invention, the compounds of formula (I) in accordance with the invention have an inhibitory activity on the Hedgehog protein signaling pathway, and are therefore of use in the treatment of pathological conditions requiring a modulation of the Hedgehog pathway, such as cancer, neurodegenerative diseases and diabetes.

The compounds of formula (I) in accordance with the present invention can be divided up into subunits A, B, C (or C' or C") and D (or D' or D") and represented by the following formulae (I-a), (I-b), (I-c) and (I-d):

Compounds (I-a)

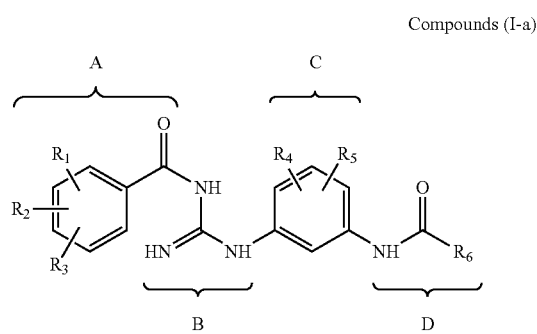

Compounds (I-b)

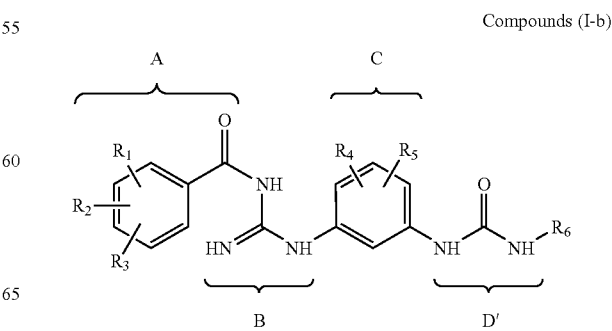

Compounds (I-c)

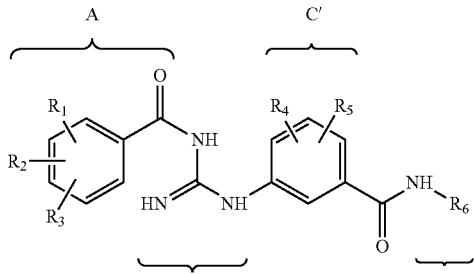

Compounds (I-d)

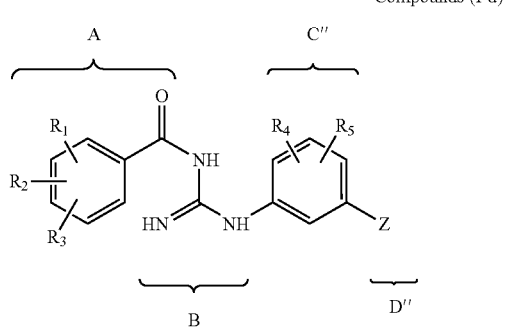

in which $R_1$, $R_2$, $R_3$, $R_4$, $R_5$ and $R_6$ have the same meanings as indicated above.

In these formulae, the subunit A corresponds to an acylaryl part, the subunit B to a guanidine, the subunit C to a 1,3-diaminoaryl group, the subunit C' to a 1,3-aminophenyl group, the subunit C" to an aminophenyl group, the subunit D to an alkyloyl, aroyl or heteroaroyl residue; the subunit D' to an alkylamino, arylamino or heteroarylamino residue; and the subunit D" (group —Z) to a monocyclic or polycyclic heteroaryl residue.

For the purpose of the present invention, the following terms have the following meanings:

- alkyl: a linear or branched, saturated aliphatic hydrocarbon-based group containing from 1 to 5 carbon atoms, preferably from 1 to 2 carbon atoms. The term "branched" means that at least one lower alkyl group such as a methyl or an ethyl is carried by a linear alkyl chain. The term "lower" alkyl denotes an alkyl containing 1 or 2 carbon atoms; the term "higher alkyl" denotes a linear or branched alkyl group containing from 3 to 5 carbon atoms. By way of an alkyl group, mention may be made, for example, of methyl, ethyl, n-propyl, i-propyl, n-butyl, t-butyl and n-pentyl groups;
- halogen atom: denotes a bromine, chlorine, iodine or fluorine atom; the designations bromine, chlorine and fluorine being preferred;
- perfluoroalkyl: denotes an alkyl group as defined above, in which all the hydrogen atoms have been replaced with fluorine atoms. Among the perfluoroalkyl groups, trifluoromethyl and perfluoroethyl groups are preferred;
- alkoxy: denotes an O-alkyl group in which the alkyl group can have the same meaning as that indicated above. By way of example of alkoxy groups, mention may in particular be made of methoxy, ethoxy, n-propoxy, isopropoxy, n-butoxy and pentoxy groups;
- alkylthio: denotes an S-alkyl group in which the alkyl group can have the same meaning as that indicated above. By way of examples of alkylthio groups, mention may in particular be made of methylthio, ethylthio, isopropylthio, butylthio and pentylthio groups;
- aryl group: denotes any functional group or substituent derived from at least one aromatic ring; an aromatic ring corresponds to any planar monocyclic or polycyclic group comprising a delocalized π system in which each atom of the ring comprises a p orbital, said p orbitals overlapping one another; among such aryl groups, mention may be made of phenyl, benzylcyclobutene, pentalene, naphthalene, benzylphenyl and anthracene groups;
- heteroaryl group: denotes any functional group or substituent derived from at least one aromatic ring as defined above and containing at least one heteroatom chosen from P, S, O and N; among the heteroaryl groups, mention may be made of furan, pyridine, pyrrole, thiophene, imidazole, pyrazole, oxazole, isoxazole, thiazole, pyridine, pyrazine, pyrimidine, pyridazine, benzofuran, isobenzofuran, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine groups;
- saturated or unsaturated, monocyclic or polycyclic hydrocarbon-based group: denotes any functional group or substituent derived from a nonaromatic ring containing at least three carbon atoms which may optionally contain one or more heteroatoms chosen from P, S, O and N. Among such groups, mention may in particular be made of cyclopropyl, cyclobutyl, cyclopentyl and cyclohexyl; the cyclohexyl group being preferred.

According to one preferred embodiment of the invention, the compounds of formula (I) are chosen from those in which:

$R_1$, $R_2$ and $R_3$, which may be identical or different, represent a hydrogen atom, a methyloxy or ethyloxy radical, or a dioxolane fused with two adjacent carbon atoms of the phenyl ring to which they are bonded;

$R_4$ and $R_5$, which may be identical or different, represent a hydrogen, chlorine, bromine or fluorine atom, or a methyl or methoxy radical, and preferably a hydrogen, chlorine or fluorine atom or a methyl radical; and Y represents a monocyclic or polycyclic heteroaryl group, —NH—(C=O)—$R_6$, —(C=O)—NH—$R_6$ or —NH—(C=O)—NH—$R_6$ in which $R_6$ represents a phenyl group optionally substituted with a halogen atom, an alkyl, diaminoalkyl or alkoxy radical, a cycloalkyl group, or an aryl group; a cycloalkyl group; a pyridinyl group; a naphthyl group; a furyl group, a thiophenyl group; an isopropyl radical.

According to one preferred embodiment of the present invention, the group Y is chosen from indole and imidazole fused to a thiazole group, when said group Y represents a monocyclic or polycyclic heteroaryl group.

According to another preferred embodiment of the present invention, $R_6$ represents a phenyl group optionally substituted with a chlorine atom, a methoxy radical, a morpholine, or a phenyl or phenoxy group; a cyclohexyl group; a pyridinyl group; a naphthyl group; a furyl group; when said group Y represents an —NH—(C=O)—$R_6$, —(C=O)—NHR_6 or —NH—(C=O)—NH—$R_6$ group.

Another subject of the present invention relates to novel acyl guanidine derivatives as such, corresponding to formula (I) below:

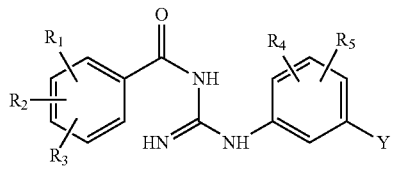

(I)

in which:
- $R_1$, $R_2$ and $R_3$, which may be identical or different, and independently of one another, represent a hydrogen or halogen atom, a hydroxyl radical, an alkyl group, a perfluoroalkyl group, an optionally substituted alkoxy group, an alkylthio group, a nitrile group, or a fused heterocycle obtained from two of $R_1$, $R_2$ and $R_3$ which are fused with two adjacent carbon atoms of the phenyl ring to which they are bonded, the phenyl ring with said fused heterocycle preferably representing a benzodioxole, an oxindole, a benzoxazolone or a quinoline;
- Y represents a monocyclic or polycyclic heteroaryl group chosen from indole or imidazole fused to a thiazole group, or Y represents an —NH—(C═O)—$R_6$, —(C═O)—NH—$R_6$ or —NH—(C═O)—NH—$R_6$ group, in which $R_6$ represents an unsubstituted monocyclic or polycyclic aryl group, an aryl group comprising one or more substituents chosen from a halogen atom, an alkyl, alkoxy or alkoxyaryl, monoalkylamino or dialkylamino radical, an aryl or heteroaryl group, a heterocycle; a monocyclic or polycyclic heteroaryl group; a linear or branched alkyl radical; a saturated or unsaturated, monocyclic or polycyclic hydrocarbon-based group;
- $R_4$ and $R_5$, which may be identical or different, and independently of one another, represent a hydrogen or halogen atom, or an alkoxy, alkylthio, alkyl, perfluoroalkyl, nitrile or nitro group.

According to one preferred embodiment of the invention, the compounds of formula (I) as such are chosen from those in which:
- $R_1$, $R_2$ and $R_3$, which may be identical or different, represent a hydrogen atom, a methyloxy or ethyloxy radical, or a dioxolane fused with two adjacent carbon atoms of the phenyl ring to which they are bonded;
- $R_4$ and $R_5$, which may be identical or different, represent a hydrogen, chlorine, bromine or fluorine atom, or a methyl or methoxy radical, and preferably a hydrogen, chlorine or fluorine atom or a methyl radical; and
- Y represents a monocyclic or polycyclic heteroaryl group chosen from indole or imidazole fused to a thiazole group, or Y represents an —NH—(C═O)—$R_6$, —(C═O)—NH—$R_6$ or —NH—(C═O)—NH—$R_6$ group in which $R_6$ represents a phenyl group optionally substituted with a halogen atom, an alkyl, diaminoalkyl or alkoxy radical, a cycloalkyl group, or an aryl group; a cycloalkyl group; a pyridinyl group; a naphthyl group; a furyl group; a thiophenyl group; an isopropyl radical.

According to one even more preferred embodiment of the present invention, in the compounds of formula (I) as such, $R_6$ represents a phenyl group optionally substituted with a chlorine atom, a methoxy radical, a morpholine, or a phenyl or phenoxy group; a cyclohexyl group; a pyridinyl group; a naphthyl group; a furyl group; when said group Y represents an —NH—(C═O)—$R_6$, —(C═O)—NH—$R_6$ or —NH—(C═O)—NH—$R_6$ group.

By way of compounds of formula (I), mention may in particular be made of, in a nonlimiting manner:

3,4,5-trimethoxy-N—(N-(3-(4-methoxybenzamido)phenyl)carbamimidoyl)benzamide:

(Compound 1)

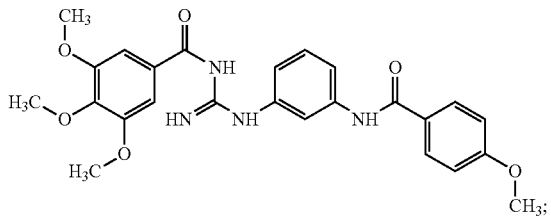

N—(N-(3-(2-chlorobenzamido)phenyl)carbamimidoyl)-3,4,5-trimethoxybenzamide:

(Compound 2)

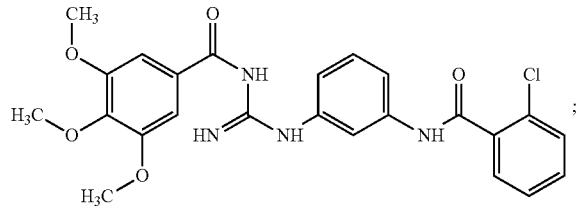

3,4,5-trimethoxy-N—(N-(3-(3-methoxybenzamido)phenyl)carbamimidoyl)benzamide:

(Compound 3)

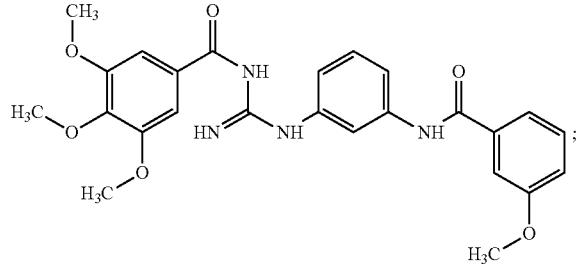

N-(3-(3-(3,4,5-trimethoxybenzoyl)guanidino)phenyl)biphenyl-4-carboxamide:

(Compound 4)

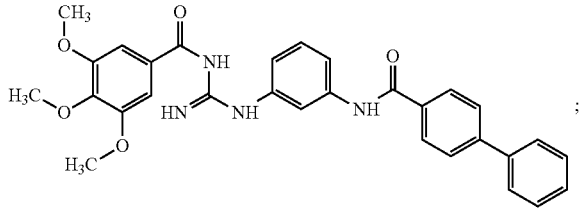

N—(N-(3-(cyclohexanecarboxamido)phenyl)carbamimidoyl)-3,4,5-trimethoxybenzamide:

(Compound 5)

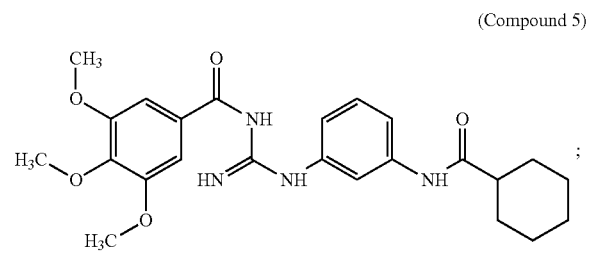 [SMILES: COc1cc(C(=O)NC(=N)Nc2cccc(NC(=O)C3CCCCC3)c2)cc(OC)c1OC]

N-(3-(3-(3,4,5-trimethoxybenzoyl)guanidino)phenyl)-2-naphthamide:

(Compound 6)

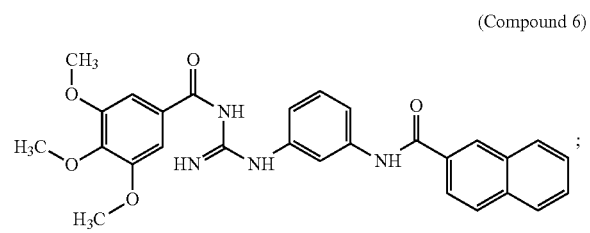 [SMILES: COc1cc(C(=O)NC(=N)Nc2cccc(NC(=O)c3ccc4ccccc4c3)c2)cc(OC)c1OC]

N-(3-(3-(3,4,5-trimethoxybenzoyl)guanidino)phenyl)isonicotinamide:

(Compound 7)

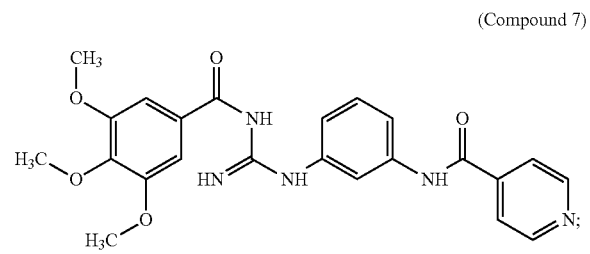 [SMILES: COc1cc(C(=O)NC(=N)Nc2cccc(NC(=O)c3ccncc3)c2)cc(OC)c1OC]

N-(3-(3-(3,4,5-trimethoxybenzoyl)guanidino)phenyl)furan-2-carboxamide:

(Compound 8)

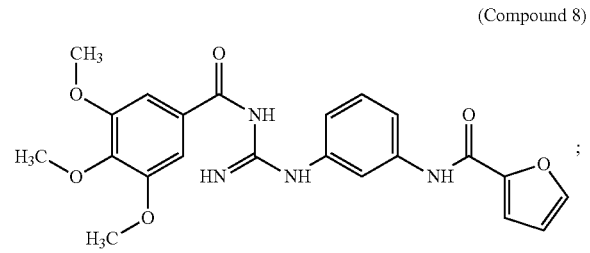 [SMILES: COc1cc(C(=O)NC(=N)Nc2cccc(NC(=O)c3ccco3)c2)cc(OC)c1OC]

N—(N-(3-benzamidophenyl)carbamimidoyl)-3,5-dimethoxybenzamide:

(Compound 9)

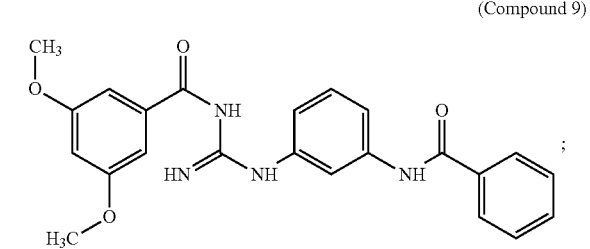 [SMILES: COc1cc(OC)cc(C(=O)NC(=N)Nc2cccc(NC(=O)c3ccccc3)c2)c1]

N—(N-(3-benzamidophenyl)carbamimidoyl)-4-ethoxy-3,5-dimethoxybenzamide:

(Compound 10)

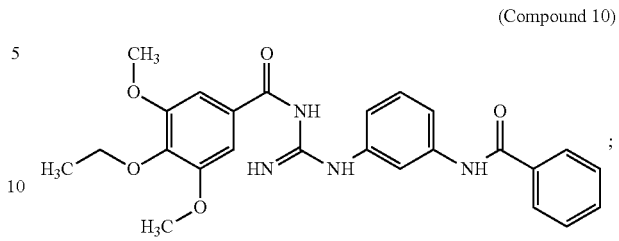

N—(N-(3-benzamidophenyl)carbamimidoyl)-3,4-diethoxy-5-methoxybenzamide:

(Compound 11)

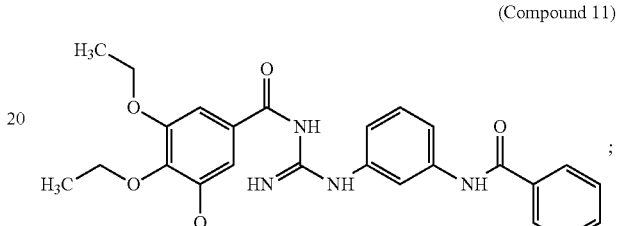

N—(N-(3-benzamidophenyl)carbamimidoyl)-7-methoxybenzo[d][1,3]dioxole-5-carboxamide:

(Compound 12)

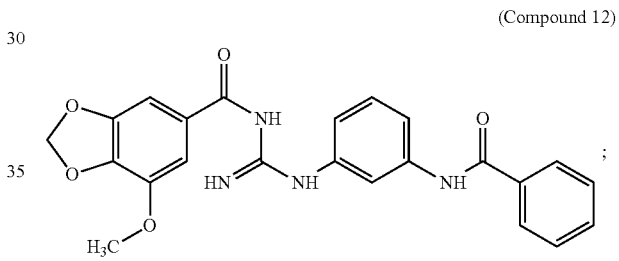

N—(N-(3-benzamidophenyl)carbamimidoyl)-2,4-dimethoxybenzamide:

(Compound 13)

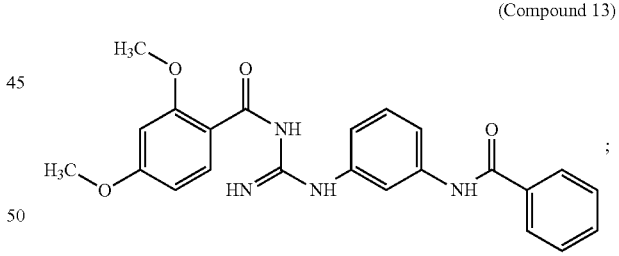

N—(N-(3-benzamido-4-fluorophenyl)carbamimidoyl)-3,4,5-trimethoxybenzamide:

(Compound 14)

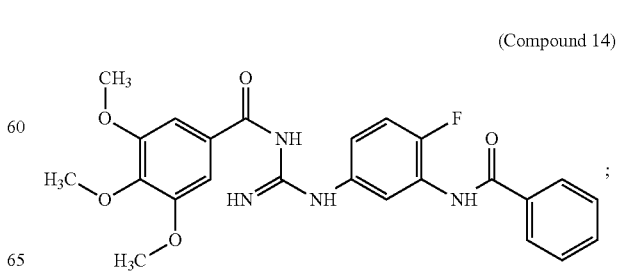

N—(N-(3-benzamidophenyl)carbamimidoyl)-3,4,5-tri-methoxybenzamide:

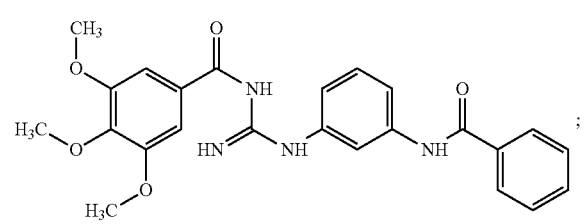

(Compound 15)

N—(N-(3-benzamido-4-chlorophenyl)carbamimidoyl)-3,4,5-trimethoxybenzamide:

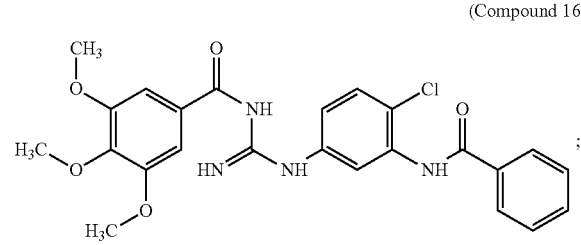

(Compound 16)

N-(2-chloro-5-(3-(3,4,5-trimethoxybenzoyl)guanidino)phenyl)biphenyl-4-carboxamide:

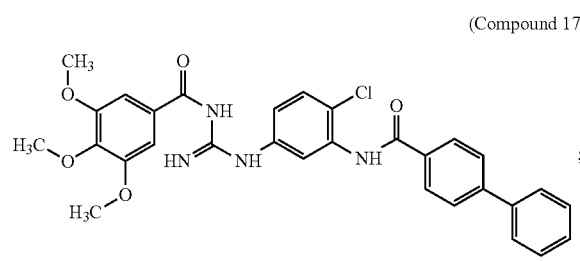

(Compound 17)

3,4,5-trimethoxy-N—(N-(3-(4-morpholinobenzamido)phenyl)carbamimidoyl)benzamide:

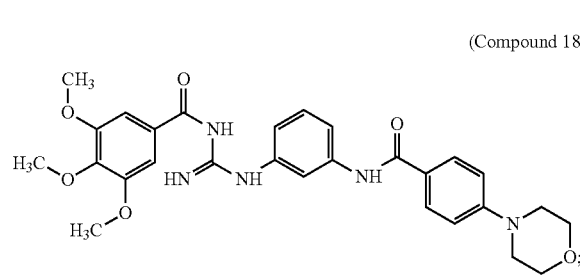

(Compound 18)

N—(N-(3-(1H-indol-2-yl)phenyl)carbamimidoyl)-3,4,5-trimethoxybenzamide:

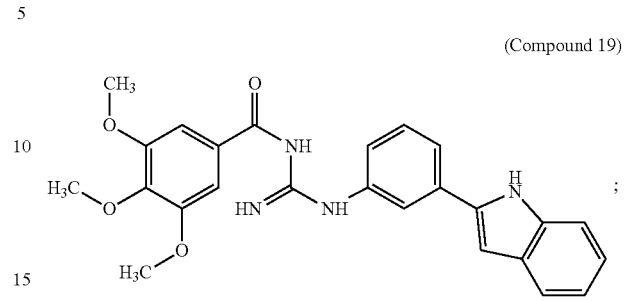

(Compound 19)

N—(N-(4-chloro-3-(4-methoxyphenylcarbamoyl)phenyl)carbamimidoyl)-3,4,5-trimethoxybenzamide:

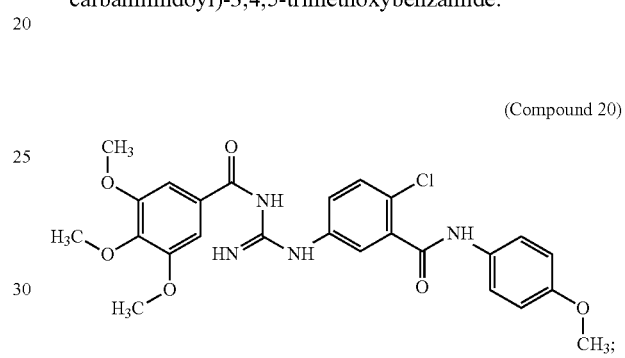

(Compound 20)

N—(N-(4-chloro-3-(phenylcarbamoyl)phenyl)carbamimidoyl)-3,4,5-trimethoxybenzamide:

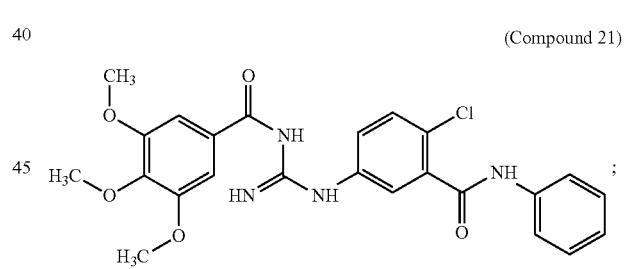

(Compound 21)

3,4,5-trimethoxy-N—(N-(4-methyl-3-(phenylcarbamoyl)phenyl)carbamimidoyl)benzamide:

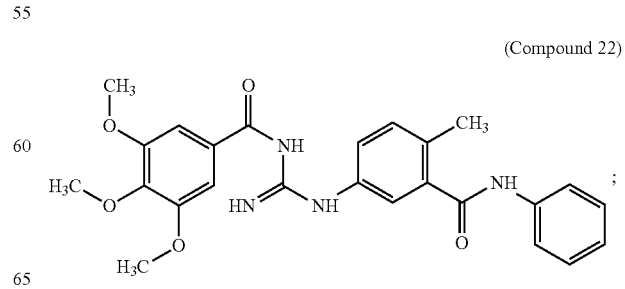

(Compound 22)

4'-fluoro-N-(3-(3-(3,4,5-trimethoxybenzoyl)guanidino)phenyl)biphenyl-4-carboxamide:

N—N-(3-benzamido-4-methylphenyl)carbamimidoyl)-3,4,5-trimethoxybenzamide:

(Compound 23)

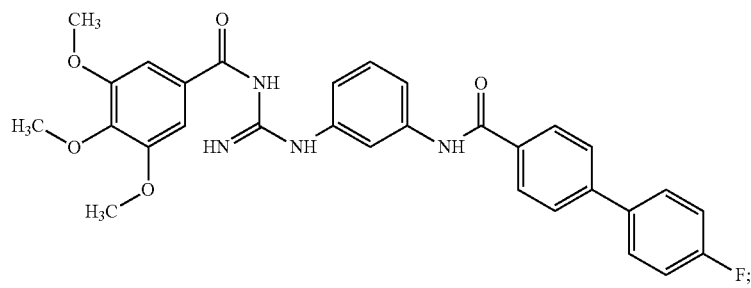

N-(2-methyl-5-(3-(3,4,5-trimethoxybenzoyl)guanidino)phenyl)biphenyl-4-carboxamide:

(Compound 27)

(Compound 24)

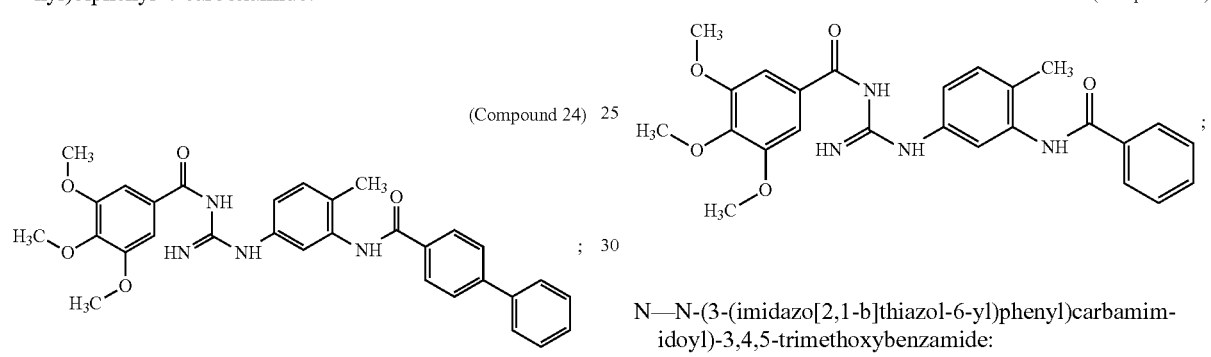

N—N-(3-(imidazo[2,1-b]thiazol-6-yl)phenyl)carbamimidoyl)-3,4,5-trimethoxybenzamide:

N-(2-methyl-5-(3-(3,4,5-trimethoxybenzoyl)guanidino)phenyl)biphenyl-3-carboxamide:

(Compound 28)

(Compound 25)

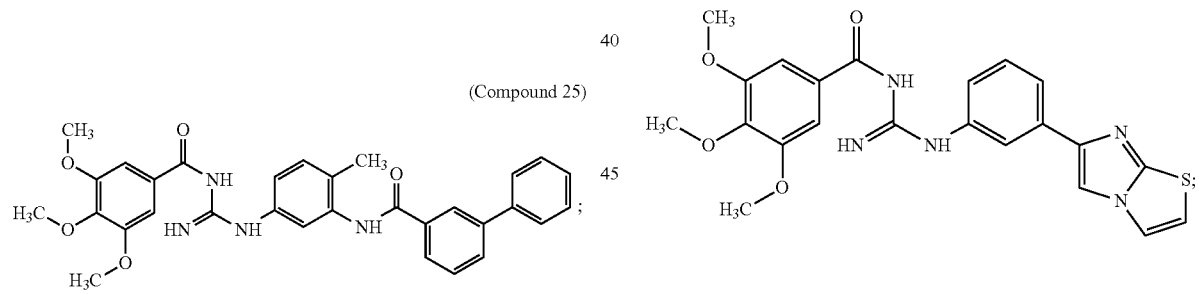

N—(N-(3-(1H-indol-1-yl)phenyl)carbamimidoyl)-3,4,5-trimethoxybenzamide:

N-(2-chloro-5-(3-(3,4,5-trimethoxybenzoyl)guanidino)phenyl)biphenyl-3-carboxamide:

(Compound 29)

(Compound 26)

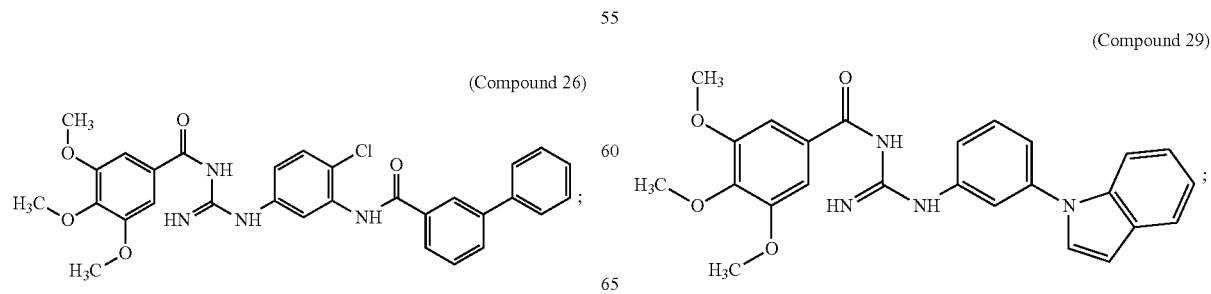

4'-fluoro-N-(2-methyl-5-(3-(3,4,5-trimethoxybenzoyl)guanidino)phenyl)biphenyl-4-carboxamide:

N-(2-methyl-3-(3-(3,4,5-trimethoxybenzoyl)guanidino)phenyl)biphenyl-4-carboxamide:

(Compound 30)

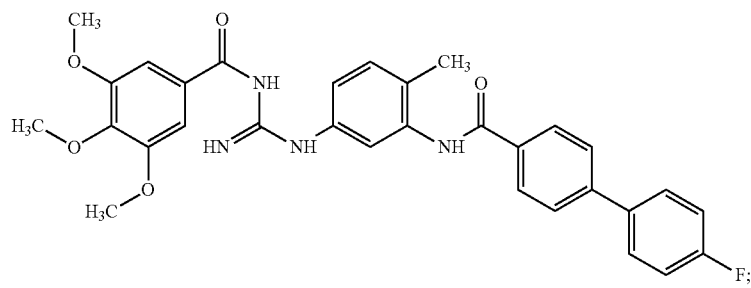

3,4,5-trimethoxy-N—(N-(4-methyl-3-(4-(pyridin-4-yl)benzamido)phenyl)carbamimidoyl)-benzamide:

(Compound 31)

(Compound 34)

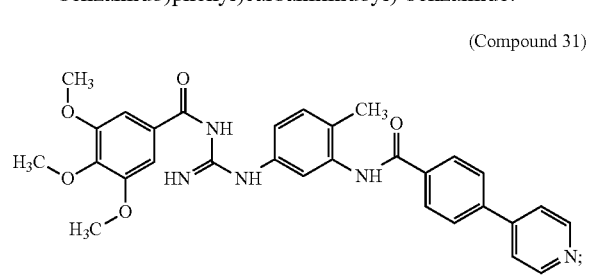

N—(N-(4-chloro-3-(4-phenoxybenzamido)phenyl)carbamimidoyl)-3,4,5-trimethoxybenzamide:

N-(4-methyl-3-(3-(3,4,5-trimethoxybenzoyl)guanidino)phenyl)biphenyl-4-carboxamide:

(Compound 32)

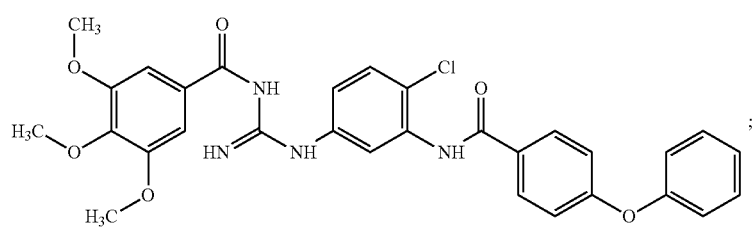

N-(3-(3-benzoylguanidino)phenyl)biphenyl-4-carboxamide:

(Compound 35)

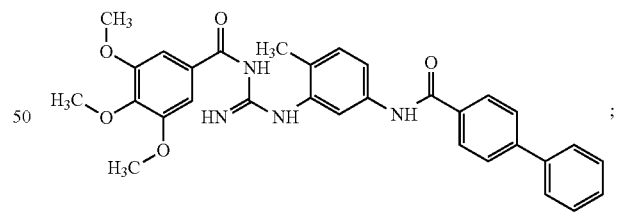

(Compound 33)

N—(N-(3-benzamidophenyl)carbamimidoyl)benzamide:

(Compound 36)

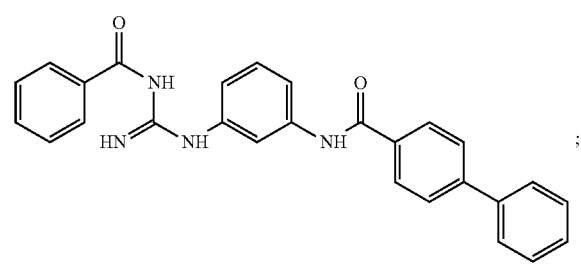

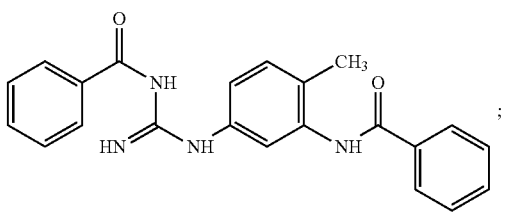

N—(N-(3-(3-biphenyl-4-ylureido)phenyl)carbamimidoyl)-3,4,5-trimethoxybenzamide:

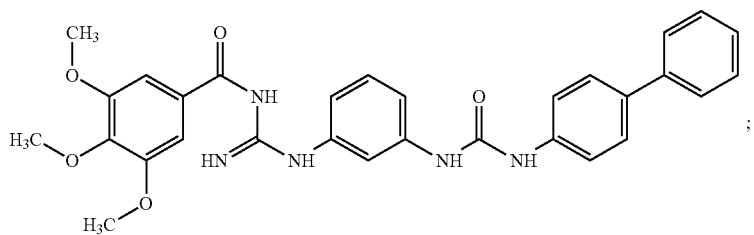

(Compound 37)

N—(N-(4-chloro-3-(3-phenylureido)phenyl)carbamimidoyl)-3,4,5-trimethoxybenzamide:

(Compound 38)

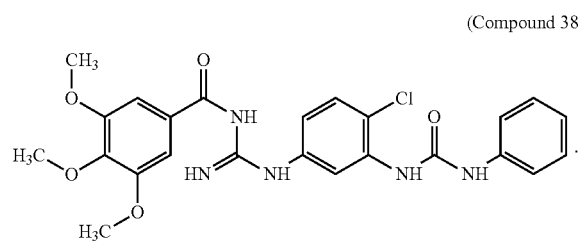

Among these compounds, the following compounds are particularly preferred since they exhibit an inhibitory activity on the Hedgehog protein signaling pathway which is greater than or equal to 80% inhibition, said inhibition being measured after activation of the Hedgehog protein signaling pathway with SAG, according to the method described by Chen et al. (Proc. Natl. Acad. Sci. USA, 2002, 99, 14071):
3,4,5-trimethoxy-N—(N-(3-(4-methoxybenzamido)phenyl) carbmimidoyl)benzamide (Compound 1);
N—(N-(3-(2-chlorobenzamido)phenyl)carbamimidoyl)-3,4,5-trimethoxybenzamide (Compound 2);
3,4,5-trimethoxy-N—(N-(3-(3-methoxybenzamido)phenyl) carbamimidoyl)benzamide (Compound 3);
N-(3-(3-(3,4,5-trimethoxybenzoyl)guanidino)phenyl)-2-naphthamide (Compound 6);
N-(3-(3-(3,4,5-trimethoxybenzoyl)guanidino)phenyl)furan-2-carboxamide (Compound 8);
N—(N-(3-benzamidophenyl)carbamimidoyl)-3,5-dimethoxybenzamide (Compound 9);
N—(N-(3-benzamidophenyl)carbamimidoyl)-7-methoxybenzo[d][1,3]dioxole-5-carboxamide (Compound 12);
N—(N-(3-benzamidophenyl)carbamimidoyl)-2,4-dimethoxybenzamide (Compound 13);
N—(N-(3-benzamidophenyl)carbamimidoyl)-3,4,5-trimethoxybenzamide (Compound 15);
N-(2-chloro-5-(3-(3,4,5-trimethoxybenzoyl)guanidino)phenyl)biphenyl-4-carboxamide (Compound 17);
N—(N-(3-(1H-indol-2-yl)phenyl)carbamimidoyl)-3,4,5-trimethoxybenzamide (Compound 19);
N—(N-(4-chloro-3-(phenylcarbamoyl)phenyl)carbamimidoyl)-3,4,5-trimethoxybenzamide (Compound 21);
4'-fluoro-N-(3-(3-(3,4,5-trimethoxybenzoyl)guanidino)phenyl)biphenyl-4-carboxamide (Compound 23);
N-(2-methyl-5-(3-(3,4,5-trimethoxybenzoyl)guanidino)biphenyl-4-carboxamide (Compound 24);
N—(N-(3-(1H-indol-1-yl)phenyl)carbamimidoyl)-3,4,5-trimethoxybenzamide (Compound 29);
4'-fluoro-N-(2-methyl-5-(3-(3,4,5-trimethoxybenzoyl) guanidino)phenyebiphenyl-4-carboxamide (Compound 30);
N—(N-(4-chloro-3-(4-phenoxybenzamido)phenyl)carbamimidoyl)-3,4,5-trimethoxybenzamide (Compound 32);
N—(N-(4-chloro-3-(3-phenylureido)phenyl)carbamimidoyl)-3,4,5-trimethoxybenzamide (Compound 38).

The compounds of formula (I) in accordance with the invention can be easily prepared, generally in three or four steps, according to synthesis processes analogous to the conventional processes known to those skilled in the art.

The schemes for general synthesis of the compounds of formula (I) in accordance with the invention, in terms of the four variants thereof (I-a), (I-b), (I-c) and (I-d), can be represented according to the appended FIGS. 1a and 1b.

In accordance with the synthesis scheme represented in the appended FIGS. 1a and 1b, in a step a), of use for obtaining compounds of formula (I-a), a commercial 3-nitroaniline of formula (II) in which the $R_4$ and $R_5$ radicals have the same meanings as those indicated above for the compounds of formula (I), is condensed with an acid chloride of formula (III) in which $R_6$ has the same meaning as that indicated above for the compounds of formula (I), for example according to the Schotten-Baumann method, so as to obtain the corresponding amide compound of formula (IV). Step b) allows coupling between a commercial 3-nitroaniline of formula (II) having $R_4$ and $R_5$ residues as indicated in formula (I), and a commercial isocyanate (III'), so as to obtain a nitrourea of formula (IV'). Step b') consists in condensing a commercial 3-nitrobenzoic acid of formula (II') with an amine of formula (V), in which $R_4$, $R_5$ and $R_6$ have the same meanings as those indicated above for the compounds of formula (I), so as to obtain the corresponding nitroamide compound of formula (IV").

Other conventional methods well known to those skilled in the art for forming an amide bond can also be used to carry out condensation steps a), b) and b').

In steps c), c'), c") and d), the nitro group of the compounds of formulae (IV), (IV') and (IV") is reduced to an amine so as to obtain, respectively, the anilines corresponding to formulae (VI), (VI') and (VII"). The 3-nitroaromatic compound of formula (IV'''), in which $R_4$, $R_5$ and Z have the same meanings as those indicated above for the compounds of formula (I), is obtained according to conventional processes known to those skilled in the art (Yang et al., Angew. Chem. Int., Ed. 2008, 47, 1473; Burkholder et al., Tetrahedron Lett., 2001, 42, 3077: Zhang et al., J. Org. Chem., 2005, 70, 5164; Aggarwal et al., Synth. Comm., 2006, 36, 875; PCT International Application WO 2006/050506 in the name of Curis). The 3-nitroaromatic compound (IV''') is then subjected to a reduction step so as to obtain the corresponding aniline (VI'''), it being possible for this reduction step to be carried out in a reducing medium, for example via the action of a reducing agent such as lead dichloride or tin dichloride, or else by hydrogenation, using for example microwave activation. Other hydrogenation methods can also be used depending on the nature of the substituents $R_4$ and $R_5$ optionally present on the phenyl ring. In this regard, when $R_4$ and/or $R_5$ represent a halogen atom such as chlorine, bromine or iodine, the reduction step is preferably carried out via the action of tin dichloride. In all other cases, a catalytic hydrogenation in the presence of Pd/C or Raney nickel is preferably carried out.

During steps e) and f), an acylisothiocyanate of formula (VIII) in which the radicals $R_1$ to $R_3$ have the same meaning as that indicated above for the compounds of formula (I) is prepared from a benzoic acid of formula (VII) or from a benzoic acid chloride of formula (VII'), for example in a solvent medium at reflux (acetonitrile or acetone) in the presence, for example, of phosgene and of ammonium thiocyanate. The compound of formula (VIII), a benzoylisothiocyanate, thus obtained is then coupled to a compound of formula (VI) or of formula (VI') so as give the corresponding acyl thiourea compounds of formulae (IX) and (X). In steps g) and g'), the same benzoylisocyanate (VIII) is condensed at reflux in a solvent with the anilines (VI'') and (VI'''), to give the acyl thioureas of formulae (XI) and (XII). Generally, the compounds of formulae (IX), (X), (XI) and (XII) are obtained in the form of solids which are then purified conventionally by recrystallization from an alcohol (Rasmussen et al., Synthesis, 1988, 456-459).

The conversion of the acyl thioureas into acyl guanidines can be carried out according to methods well known to those skilled in the art, such as that described by Shirada et al., Tetrahedron Lett., 2006, 47, 1945. The acyl thioureas (IX), (X), (XI) and (XII) are thus converted into acyl guanidines (I-a), (I-b), (I-c) and (I-d). Carrying out steps h), h'), h'') and h''') in acetonitrile, in the presence of 1-ethyl-3-(3-dimethylamino)propylcarbodiimide hydrochlorate (EDCI) and an excess of hexamethyldisilazane (HMDS), makes it possible to obtain very good yields of acyl guanidines (I-a), (I-b), (I-c) and (I-d). These compounds are obtained in the form of solids, and can be converted into the form of water-soluble salts, one of the advantages of the compounds of formula (I) being their solubility in water. Among the derived salts, mention may be made of the salts formed with hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkanesulfonic acids, such as methanesulfonic acid and ethanesulfonic acid, arylsulfonic acids, such as benzenesulfonic acid and para-toluenesulfonic acid, or arylcarboxylic acids, the salts formed with hydrochloric acid being the preferred salts. The conversion of the acyl guanidine (I-a), (I-b), (I-c) and (I-d) compounds into the form of salts is carried out under stoichiometric conditions, by simple mixing with the acid selected.

The compounds of formula (I) in accordance with the invention have the property of negatively modulating (inhibitory effect) or positively modulating (activating effect) the Hedgehog protein signaling pathway and can therefore be used, as active ingredient, for the preparation of a pharmaceutical composition intended for treatments of pathological conditions associated with hyperactivation or a deficiency of the Hedgehog protein signaling pathway.

Consequently, a subject of the present invention is also the compounds of formula (I) as medicaments, for the following treatments:

i) as a medicament intended for the treatment of tumors associated with hyperactivation of the Hedgehog protein signaling pathway; such tumors are in particular, in a nonlimiting manner, nervous tissue tumors (medulloblastomas, primative neuroectodermal tumors, glioblastomas, meningiomas and oligodendrogliomas), skin tumors (basal cell carcinomas, trichoepitheliomas, melanomas), muscle and bone tissue tumors (rhabdomyosarcomas, osteosarcomas) and tumors of other tissues (kidney, bladder, prostate, lung, stomach, pancreas, breast, liver), ii) as a medicament intended for the treatment of diseases linked to brain development (holoprosencephaly), it being possible for the compounds of formula (I) to be used in vitro for controlling and modulating the renewal of human or animal stem cells, for the treatment of strokes and cardiovascular events, and also for diseases of oligodentrocytes and Schwann cells (which provide the electrical insulation of axons), iii) as a medicament intended for the treatment of pathological conditions requiring a modulation of the Hedgehog pathway, in particular neurodegenerative pathological conditions such as Parkinson's disease, Huntington's chorea, Alzheimer's disease, multiple sclerosis and motoneuron disease, or else other pathological conditions in which modulation of the Hedgehog signaling pathway could be beneficial, such as diabetes.

The dosage employed will vary according to the condition to be treated, the route and frequency of administration, and also the nature and weight of the species to be treated (human or animal); it may vary, for example, from 1 mg to 2 g per day in adults when given orally.

In addition to the various applications as medicaments mentioned above, the compounds of formula (I) can also be used as markers for detecting the presence of proteins, or as diagnostic tools for screening for proteins, in tissues or cell lines. More particularly, the compounds of formula (I) can be used as markers or diagnostic tools for detecting or screening for the Smoothened protein, or related proteins such as Patched (Patched 1 and Patched 2), the Dispatched proteins (Dispatched 1 and Dispatched 2), or else the HIP protein. Another subject of the present invention is a pharmaceutical composition, characterized in that it comprises, as active ingredient, at least one compound of formula (I) as defined above, and at least one pharmaceutically acceptable excipient.

Within the pharmaceutical compositions in accordance with the invention, the compound(s) of formula (I) is (are) preferably used in an amount which allows unitary doses of between approximately 1 mg and 2 g to be administered.

Those skilled in the art will select one or more pharmaceutically acceptable excipients according to the route of administration of the pharmaceutical composition. Of course, those skilled in the art will take care, at this time, to ensure that the excipient(s) used is (are) compatible with the intrinsic properties associated with the composition in accordance with the present invention.

In addition, the form of the medicament or of the pharmaceutical composition (for example, a solution, a suspension, an emulsion, tablets, gel capsules, suppositories, etc.) will depend on the route of administration selected.

Thus, for the purpose of the present invention, the medicament or the pharmaceutical composition can be administered via any appropriate route, for example orally, anally, locally, systemically, intravenously, intramuscularly or mucosally, or else using a patch, or alternatively in a form encapsulated in, or immobilized on, liposomes, microparticles, microcapsules, and the like.

By way of nonlimiting examples of excipients suitable for oral administration, mention may in particular be made of talc, lactose, starch and its derivatives, cellulose and its derivatives, polyethylene glycols, acrylic acid polymers, gelatin, magnesium stearate, animal, vegetable or synthetic fats, paraffin derivatives, glycols, stabilizers, preservatives, antioxidants, wetting agents, anti-caking agents, dispersing agents, emulsifiers, taste modifiers, penetrating agents, solubilizing agents, etc.

The techniques for formulating and administering the medicaments and pharmaceutical compositions are well known in the art under consideration here, it being possible in particular for those skilled in the art to refer to the handbook Remington's Pharmaceutical Sciences, (21$^{st}$ edition).

BRIEF DESCRIPTION OF THE DRAWINGS

In addition to the above arrangements, the invention also comprises other arrangements which will emerge from the following description, which refers to examples of synthesis of the compounds of formula (I), to an example of use of the compounds of formula (I) according to the present invention, and also to the appended drawings in which.

DETAILED DESCRIPTION OF THE INVENTION

Example 1

Syntheses of Various Compounds of Formula (I)

In these examples, the reactions were carried out under an inert gas (nitrogen) atmosphere using Schlenk (standard) techniques. The solvents were dried according to standard methods and distilled under nitrogen before use. All the reagents were obtained commercially and used as they were, without prior purification.

The mass spectrometries (ESI+) were recorded on an LC/MSD spectrometer sold under the reference Agilent® 1100. The nuclear magnetic resonance (NMR) spectra were recorded on a Bruker® AC200 apparatus at 200 MHz ($^1$H) or on a Bruker® AC400 apparatus at 400 MHz ($^1$H) or at 100 MHz ($^{13}$C).

A) Synthesis of Compound 19

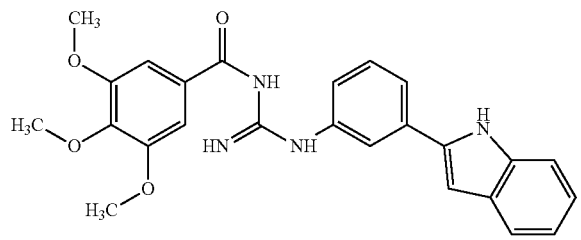

(Compound 19)

Figure 1A:
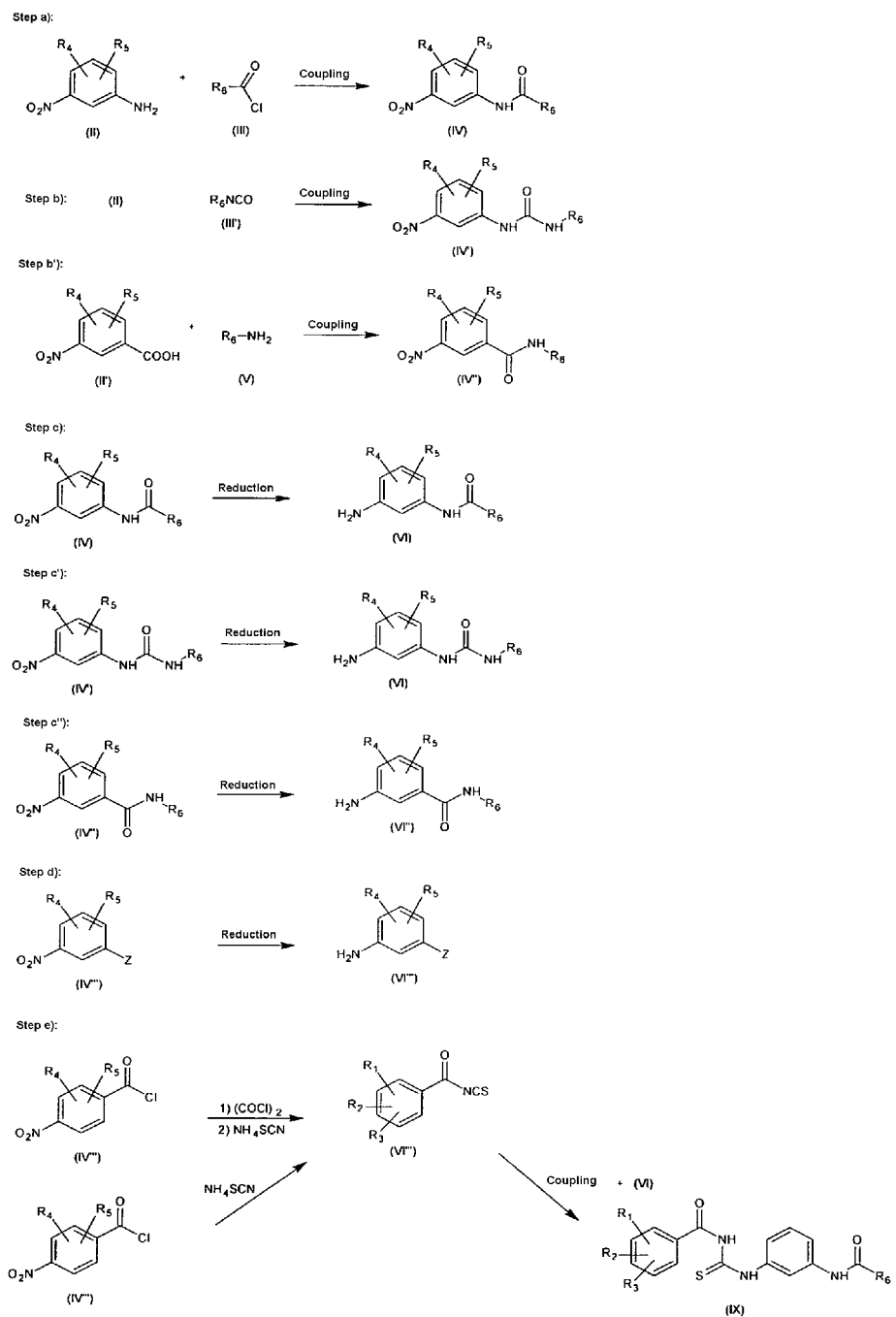
FIGS. 1a and 1b illustrate the general synthesis pathways for the compounds of formula (I)

1) Preparation of the Aniline of Formula (VP''') (FIG. 1a)

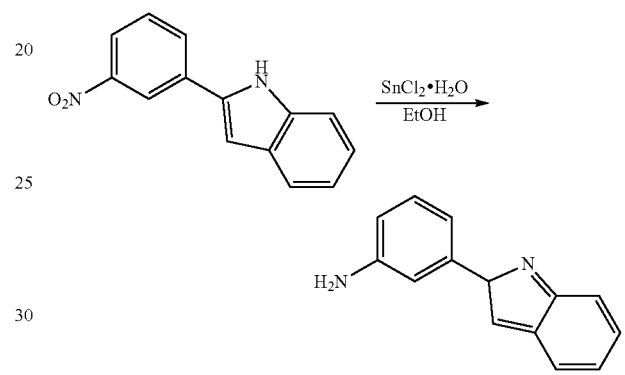

2-(3-Nitrophenyl)-1H-indole is prepared according to the method described in Yang et al., Angew. Chem., Int., Ed. 2008, 47, 1473. The nitroindole derivative (1.19 g, 5 mmol) is dissolved in 32 ml of ethanol, and the medium is heated at 80° C. SnCl$_2$.H$_2$O (3.8 g, 5 eq., 16 mmol) is added in one go. The medium is then heated for a further 2 hours, and then poured onto a water/ice mixture and basified with Na$_2$CO$_3$. The mixture is then extracted with ethyl acetate. The organic phase is washed with a saturated solution of NaCl, then dried and concentrated under vacuum so as to obtain crystals. This residue is recrystallized from ethanol, so as to obtain a solid (980 mg, yield=86%).

Mp=134° C.; [ES/MS] m/z 210 [M+1]$^+$

Figure 1B:
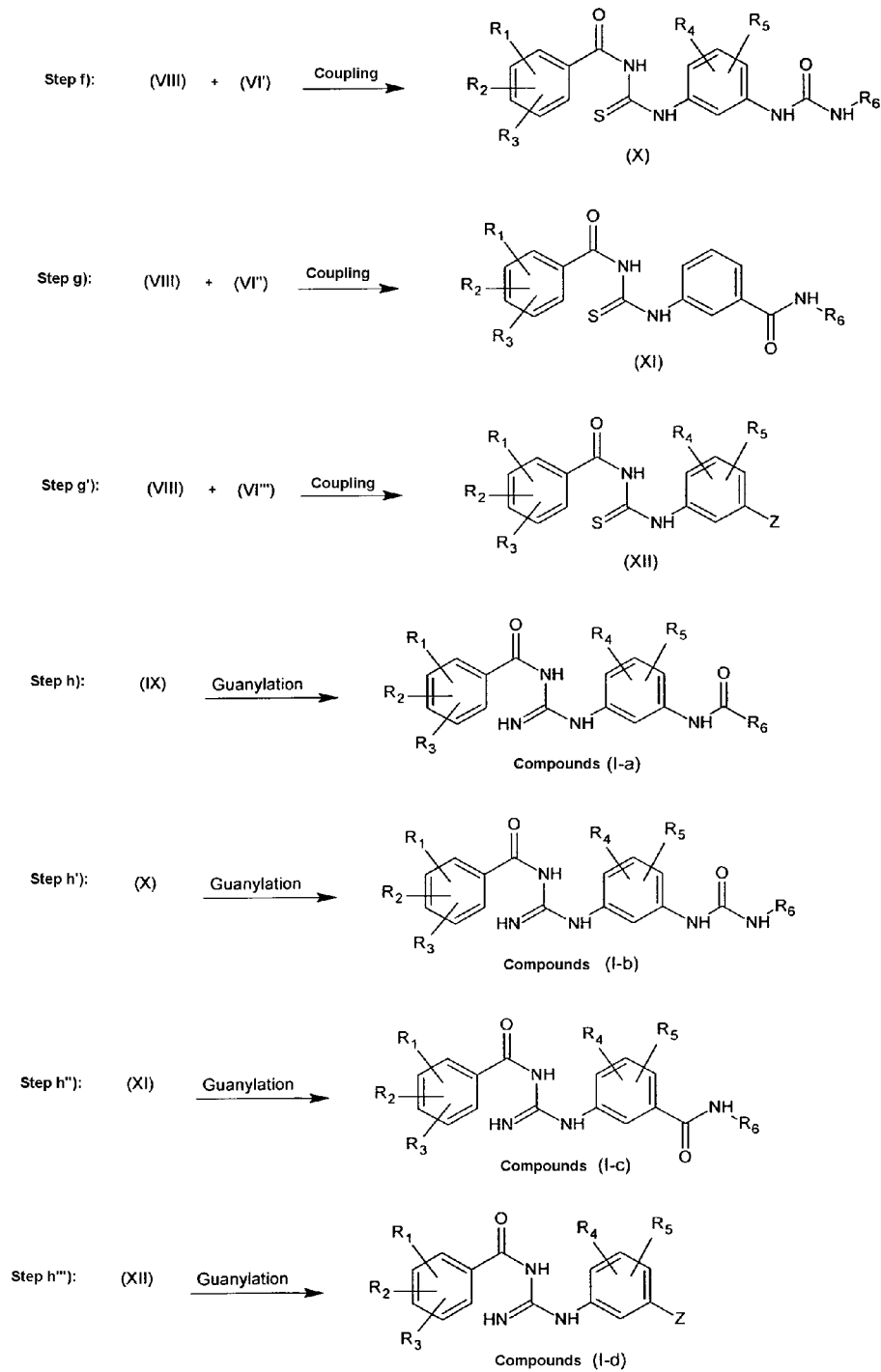

2) Preparation of the Acyl Thiourea of Formula (XII) (FIG. 1b)

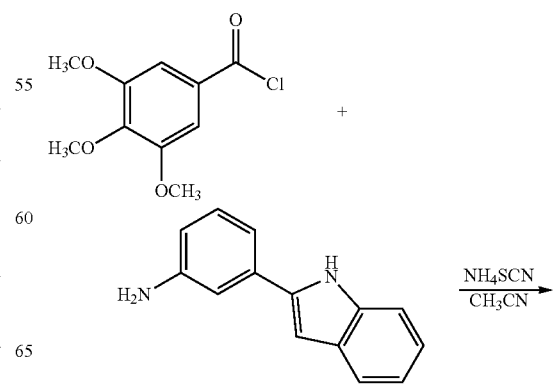

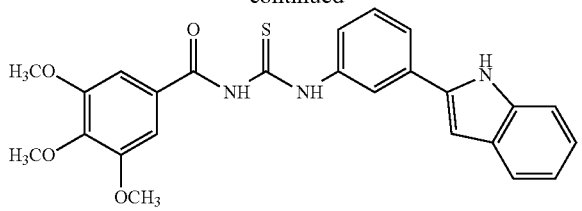

Ammonium thiocyanate (123 mg, 1.2 eq., 1.63 mmol) and 3,4,5-trimethoxybenzoyl chloride (345 mg, 1.1 eq., 1.5 mmol) are dissolved in 5 ml of acetone. The mixture is refluxed for 1 hour. The aniline obtained during the preceding step (315 mg, 1 eq., 1.45 mmol) is added, and the reflux is maintained for a further 1 hour. The mixture is then poured into water, and then filtered and recrystallized from acetonitrile, so as to obtain the acyl thiourea of formula (XII) (320 mg, 52%).

Mp=136° C., [ES/MS] m/z 462 [M+1]$^+$

3) Production of Compound 19 (FIG. 1b)

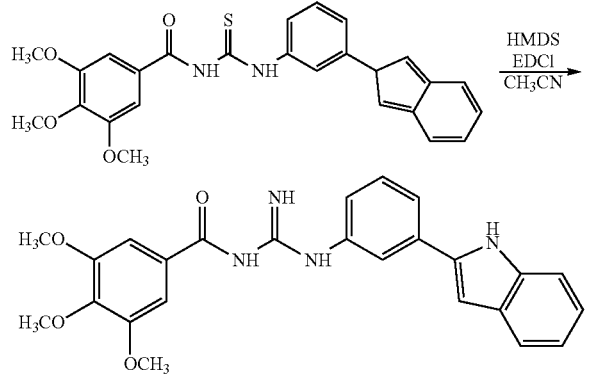

The acyl thiourea of formula (XII) previously obtained (69 mg, 0.15 mmol) and hexamethyldisilazane (0.32 ml, 10 eq., 1.5 mmol) are dissolved in 1.5 ml of acetonitrile, and then cooled to 0° C. 1-Ethyl-3-(3-dimethylamino)-propylcarbodiimide hydrochloride (58 mg, 2 eq., 0.3 mmol) is then added. The mixture is stirred at ambient temperature for 5 hours. The reaction medium is poured into water, extracted with ethyl acetate, washed with a saturated solution of NaCl, and then dried and concentrated under vacuum. The residue obtained is purified by chromatography on SiO$_2$ (eluent: ethyle acetate/heptane: 1/1). A white solid corresponding to compound 19 is obtained (52 mg, 78%).

Mp=149° C.; [ES/MS] m/z 446 [M+1]$^+$

4) Preparation of the Hydrochloride of Compound 19

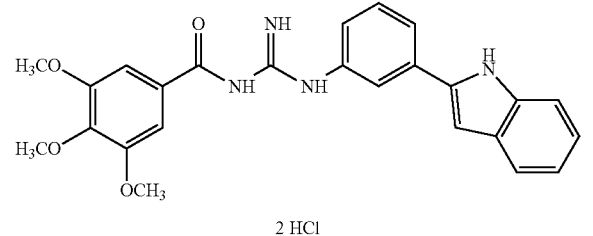 [SMILES: COc1cc(C(=O)NC(=N)Nc2cccc(-c3cc4ccccc4[nH]3)c2)cc(OC)c1OC]

2 HCl

Compound 19 (55 mg, 0.123 mmol) is dissolved in 5 ml of isopropanol. An HCl solution is then added in Et$_2$O (0.14 ml, 0.27 mmol), and the medium is then stirred for 2 hours. The reaction medium is evaporated and then the salt is crystallized from ether. The hydrochloride of compound 19 (43 mg, 68%) having an Mp of 225° C. is then obtained.

B) Synthesis of Compound 20

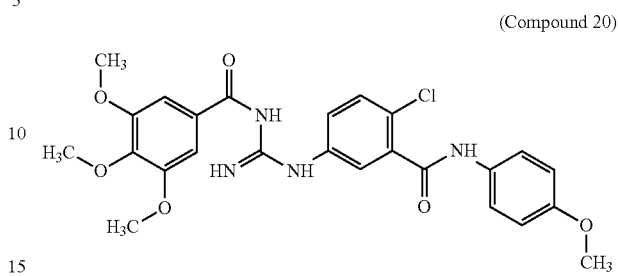

(Compound 20)

1) Preparation of the Acid Chloride of Formula (III) (FIG. 1a)

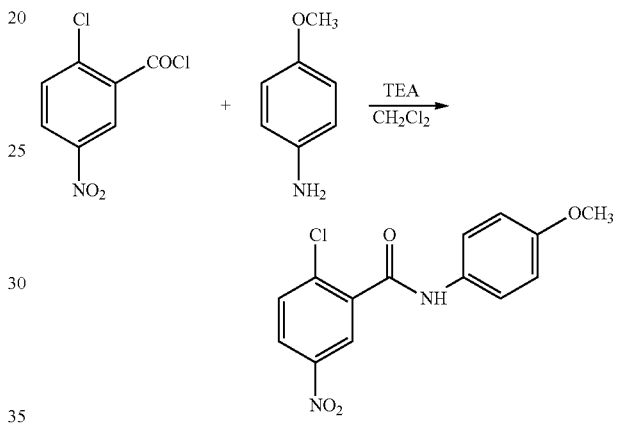

2-Chloro-5-nitrobenzoic acid (6.04 g, 0.03 mol) is dissolved in 200 ml of dichloromethane. Oxalyl chloride (3.88 ml, 1.5 eq., 0.045 mol) is then added, followed, dropwise, by dimethylformamide (DMF), and the reaction medium is stirred for 3 hours. The solvent is then evaporated off so as to recover the acid chloride of formula (III).

2) Preparation of the Amide of Formula (IV') (FIG. 1a)

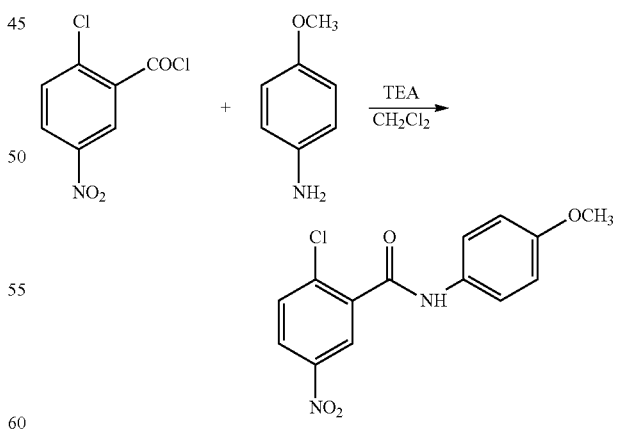

4-Methoxyaniline (1.02 g, 1 eq., 8.3 mmol) and triethylamine (1.4 ml, 1.2 eq., 10 mmol) are dissolved in 12 ml of dichloromethane. The acid chloride of formula (III) previously prepared (2 g, 1 eq., 0.9 mmol), dissolved in 15 ml of CH$_2$Cl$_2$, is then added and the reaction medium is stirred for 12 hours. Water and ethyl acetate are then added, before recovering the organic phase, drying it and concentrating it under vacuum. This residue is crystallized from isopropanol, so as to obtain a solid (2.12 g, 83%).

Mp=143° C.; [ES/MS] m/z 307 [M+1]$^+$

3) Preparation of the Aniline of Formula (VII") (FIG. 1a)

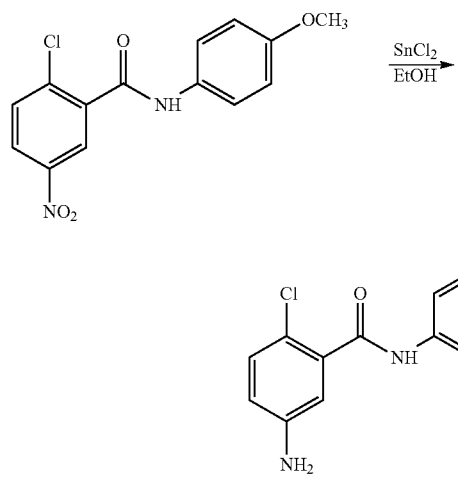

The amide of formula (IV') previously obtained (1.53 g, 5 mmol) is dissolved in 30 ml of absolute ethanol, and then heated at 80° C. SnCl$_2$.H$_2$O (3.3 g) is added, and the heating is maintained for a further 2 hours. The solvent is evaporated off, and then the residue is washed with water and then basified with a saturated aqueous Na$_2$CO$_3$ solution. The mixture is then extracted with ethyl acetate. The organic phase is washed with a saturated solution of NaCl, and then dried and concentrated, so as to obtain a residue which is recrystallized from isopropanol. A solid is recovered (845 mg, 61%).

Mp=132-133° C.; [ES/MS] m/z 277 [M+1]$^+$

4) Preparation of the Acyl Thiourea of Formula (XI) (FIG. 1b)

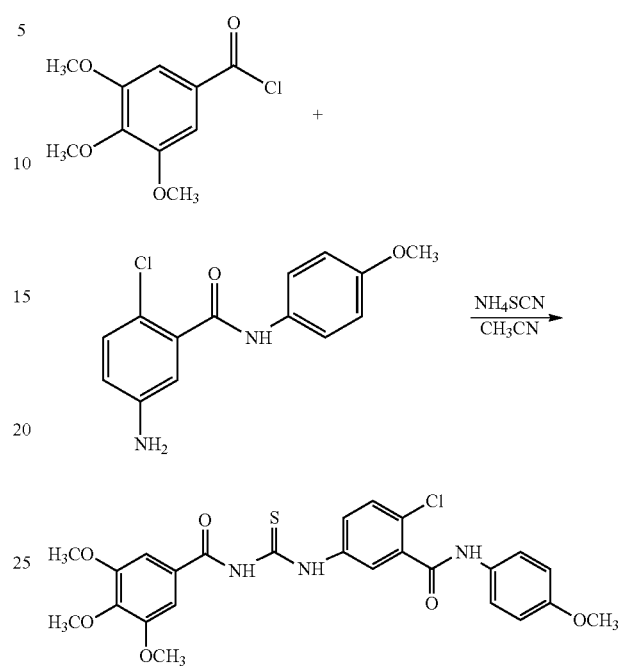

Ammonium thiocyanate (82 mg, 1.2 eq., 1.09 mmol) and acid chloride of formula (VII) (in this case 3,4,5-trimethoxybenzoyl chloride) (230 mg, 1.1 eq., 1 mmol) are dissolved in 5 ml of acetone. The mixture is refluxed for 1 hour. The aniline obtained during the preceding step (250 mg, 1 eq., 0.9 mmol) is added, and the reflux is maintained for a further 1 hour. The mixture is then poured into ice-cold water, and then filtered and recrystallized from acetonitrile, so as to obtain the acyl thiourea of formula (XI) (180 mg, 38%).

Mp=165° C., [ES/MS] m/z 556 [M+1]$^+$

5) Production of Compound 20

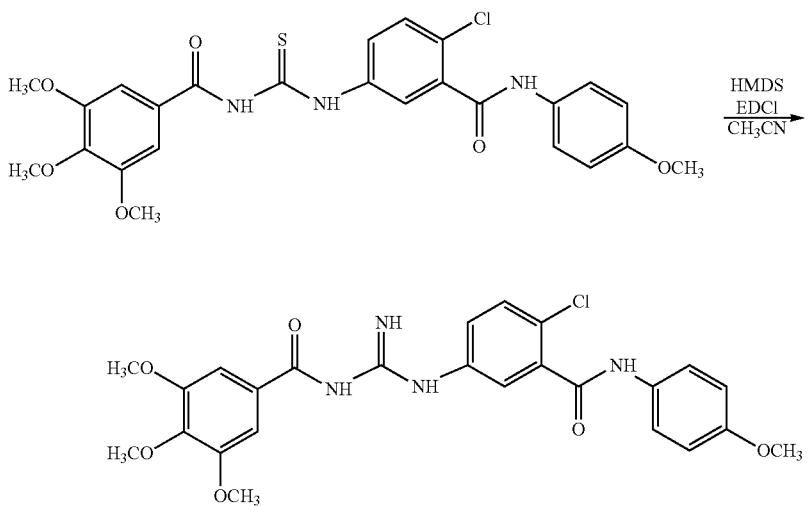

The acyl thiourea of formula (XI) previously obtained (66 mg, 0.125 mmol) and hexamethyldisilazane (0.26 ml, 1.25 mmol) are dissolved in 1.5 ml of acetonitrile, and then cooled to 0° C. in an ice bath. 1-Ethyl-3-(3-dimethylamino)propyl-carbodiimide hydrochloride (48 mg, 2 eq., 0.25 mmol) is then added. The mixture is stirred at ambient temperature for 5 hours. The reaction medium is poured onto ice, and the aqueous phase is extracted several times with ethyl acetate. The organic phase is washed with a saturated solution of NaCl, and then dried and concentrated under vacuum. The residue obtained is crystallized from an isopropanol/heptane mixture, and then purified by chromatography on $SiO_2$ (eluent: ethyl acetate/heptane: 1/1, then pure ethyl acetate), so as to obtain 51 mg of compound 20.

Mp=105° C.; [ES/MS] m/z 513 [M+1]$^+$

C) Synthesis of Compound 24

(Compound 24)

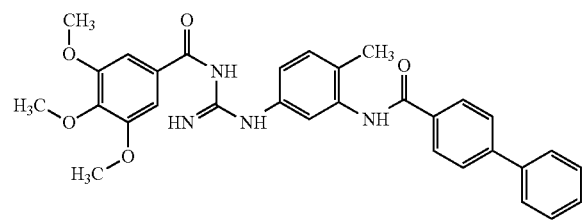

1) Preparation of the Amide of Formula (IV) (FIG. 1a)

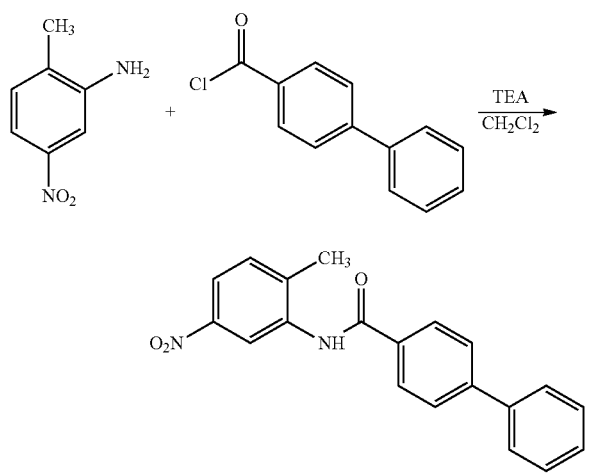

2-Methyl-5-nitroaniline (1.26 g, 1 eq., 8.3 mmol) is dissolved in 40 ml of dichloromethane. Triethylamine (1.4 ml, 1.2 eq., 10 mmol) is then added, followed, dropwise, by 4-phenylbenzoyl chloride (2.1 g, 10 mmol, prepared from the corresponding acid of oxalyl chloride) in solution in 20 ml of dichloromethane, and the medium is stirred at ambient temperature for 4 hours. The organic phase is then diluted with $CH_2Cl_2$, washed with water, and then dried with $Na_2SO_4$. The organic phase is then concentrated, and the crystals recovered are then recrystallized from methanol, so as to obtain 2.36 g (yield=85%) of amide of formula (IV).

Mp=186° C.; [ES/MS] m/z 332 [M+1]$^+$

2) Preparation of the Aniline of Formula (VI) (FIG. 1a)

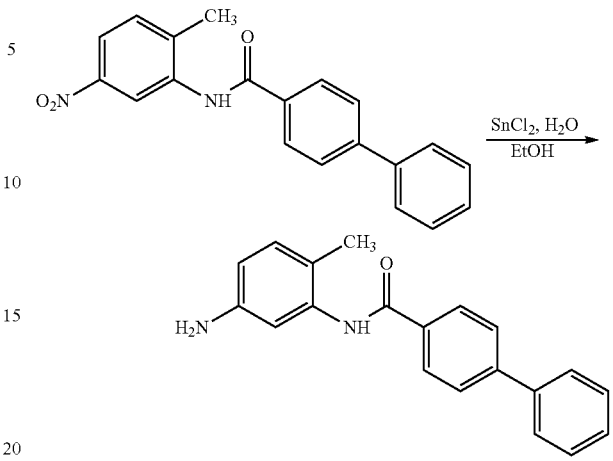

The amide of formula (IV) obtained (1.1 g, 3 mmol) is then dissolved in 32 ml of ethanol, and the medium is heated at 80° C. $SnCl_2.H_2O$ (3.8 g, 5 eq., 16 mmol) is added in one go. The medium is then heated for a further 2 hours, and then poured into a water/ice mixture and basified with $Na_2CO_3$. The mixture is then extracted with ethyl acetate. The organic phase is washed with a saturated solution of NaCl, and then dried and concentrated under vacuum, so as to obtain crystals. This residue is recrystallized from ethanol, so as to obtain a solid (920 mg, 66%).

Mp=96° C.; [ES/MS] m/z 303 [M+1]$^+$

3) Preparation of the Acyl Thiourea of Formula (IX) (FIG. 1a)

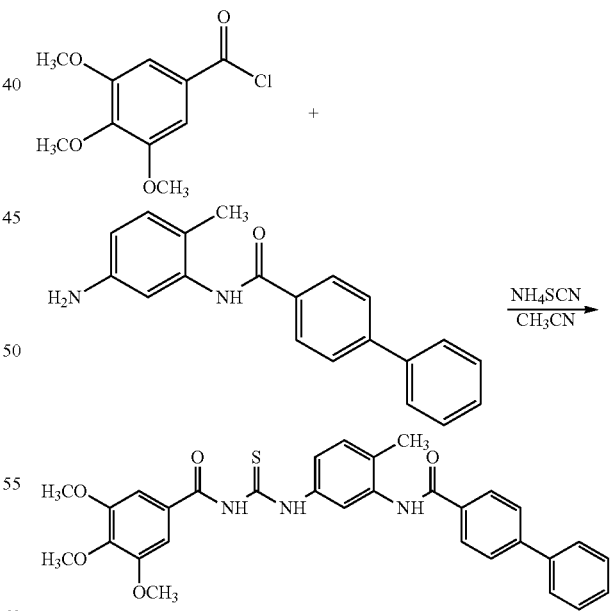

Ammonium thiocyanate (123 mg, 1.2 eq., 1.63 mmol) and 3,4,5-trimethoxybenzoyl chloride (345 mg, 1.1 eq., 1.5 mmol) are dissolved in 5 ml of acetone. The mixture is refluxed for 1 hour. The aniline obtained during the preceding step (408 mg, 1 eq., 1.35 mmol) is added, and the reflux is maintained for a further 1 hour. The mixture is then poured into water, and then filtered and recrystallized, so as to obtain the acyl thiourea of formula (IX) (587 mg, 78%).

Mp=173° C.; [ES/MS] m/z 556 [M+1]$^+$

4) Production of Compound 24

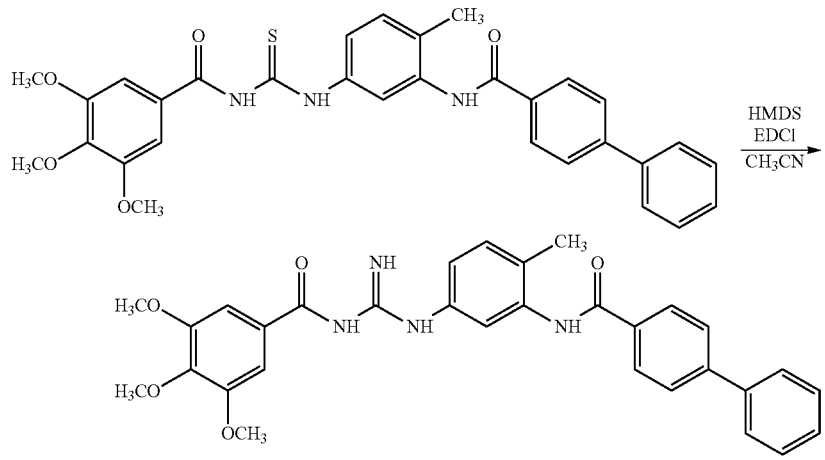

The acyl thiourea of formula (IX) previously obtained (250 mg, 0.125 mmol) and hexamethyldisilazane (0.95 ml, 1.25 mmol) are dissolved in 6 ml of acetonitrile, and then cooled to 0° C. in an ice bath. 1-Ethyl-3-(3-dimethylamino)propylcarbodiimide hydrochloride (171 mg, 2 eq., 0.9 mmol) is then added. The mixture is stirred at ambient temperature for 5 hours. The reaction medium is poured onto ice, and the aqueous phase is extracted several times with ethyl acetate. The organic phase is washed with a saturated solution of NaCl, and then dried and concentrated under vacuum. The residue obtained is crystallized from an isopropanol/heptane mixture, and then purified by chromatography on SiO$_2$ (eluent: ethyl acetate/heptane: 4/1, then pure ethyl acetate), so as to obtain 161 mg of compound 24.

Mp=135° C.; [ES/MS] m/z 513 [M+1]$^+$

D) Synthesis of Compound 38

(Compound 38)

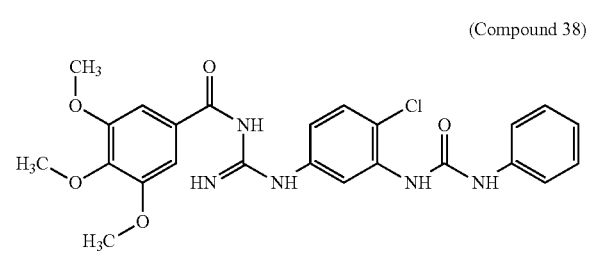 [SMILES: COc1cc(C(=O)NC(=N)Nc2ccc(Cl)c(NC(=O)Nc3ccccc3)c2)cc(OC)c1OC]

1) Preparation of the Adduct of Formula (IV') (FIG. 1a)

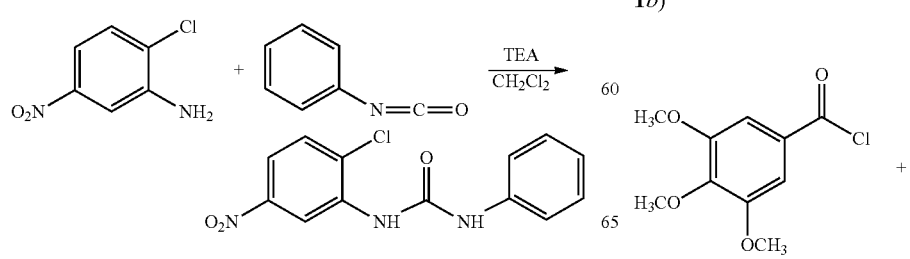

2-Chloro-5-nitroaniline (5.17 g, 30 mmol) and phenyl isocyanate (3.57 g, 3.5 ml, 30 mmol) are dissolved in 30 ml of tetrahydrofuran (THF), and then refluxed for 4 hours. The residue obtained is evaporated under vacuum and purified by chromatography on SiO$_2$ (eluent: ethyl acetate/heptane: 3/7), so as to obtain the adduct of formula (IV') (116 mg, 79%).

Mp=142° C.; [ES/MS] m/z 292 [M+1]$^+$

2) Preparation of the Aniline of Formula (VI') (FIG. 1a)

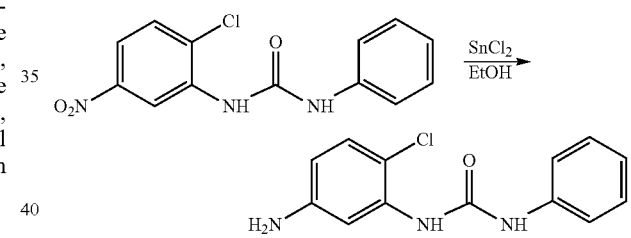

The adduct of formula (IV') (514 mg, 2 mmol) is dissolved in 20 ml of ethanol, and the medium is heated at 80° C. SnCl$_2$.H$_2$O (2.3 g, 5 eq., 10 mmol) is added in one go. The medium is then heated for a further 2 hours, and then poured into a water/ice mixture and basified with Na$_2$CO$_3$. The mixture is then extracted with ethyl acetate. The organic phase is washed with a saturated solution of NaCl, and then dried and concentrated under vacuum, so as to obtain crystals. This residue is purified by chromatography on SiO$_2$, so as to obtain an oil (404 mg, 89%).

Mp=134° C.; [ES/MS] m/z 228 [M+1]$^+$

3) Preparation of the Acyl Thiourea of Formula (X) (FIG. 1b)

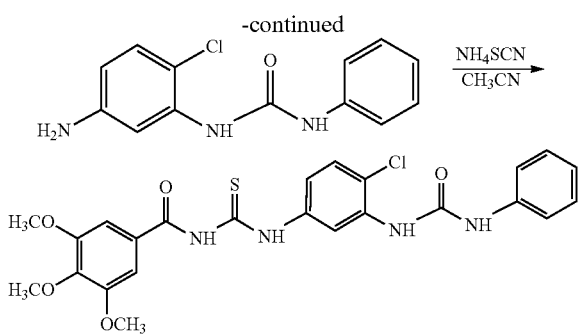

Ammonium thiocyanate (82 mg, 1.2 eq., 1.09 mmol) and 3,4,5-trimethoxybenzoyl chloride (230 mg, 1.1 eq., 1 mmol) are dissolved in 5 ml of acetone. The mixture is refluxed for 1 hour. The aniline obtained during the preceding step (204 mg, 1 eq., 0.9 mmol) is added, and the reflux is maintained for a further 1 hour. The mixture is then poured into water, and then filtered and recrystallized from acetonitrile, so as to obtain the acyl thiourea of formula (X) (185 mg, 42%).

Mp=250° C., [ES/MS] m/z 481 [M+1]$^+$

4) Production of Compound 38

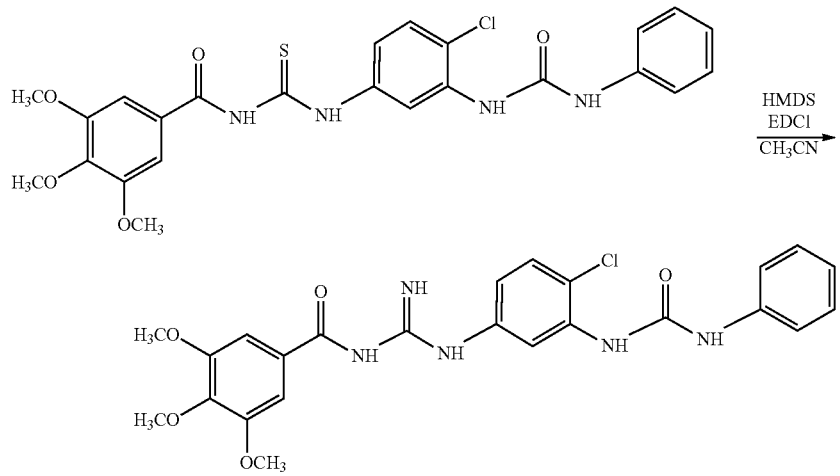

The acyl thiourea of formula (X) previously obtained (72 mg, 0.15 mmol) and hexamethyldisilazane (0.32 ml, 10 eq., 1.5 mmol) are dissolved in 1.5 ml of acetonitrile, and then cooled to 0° C. in an ice bath. 1-Ethyl-3-(3-dimethylamino) propylcarbodiimide hydrochloride (58 mg, 2 eq., 0.3 mmol) is then added. The mixture is stirred at ambient temperature for 5 hours. The reaction medium is poured into water, and the aqueous phase is extracted with ethyl acetate. The organic phase is washed with a saturated solution of NaCl, and then dried and concentrated under vacuum. The residue obtained is purified by chromatography on SiO$_2$ (eluent:ethyl acetate/heptane: 1/1), so as to obtain compound 38 (35 mg, 52%), having an Mp of 179° C.

The analyses obtained for all the compounds of formula (I), synthesized by analogy according to the processes described in detail above, are given hereinafter:

Compound 1: 3,4,5-trimethoxy-N—(N-(3-(4-methoxy-benzamido)phenyl)-carbamimidoyl)benzamide ($C_{25}H_{26}N_4O_6$)

Molecular weight (MW)=478; [ES/MS] m/z 479 [M+1]$^+$; Mp=126° C.

Compound 2: N—(N-(3-(2-chlorobenzamido)phenyl)car-bamimidoyl)-3,4,5-trimethoxybenzamide ($C_{24}H_{23}ClN_4O_5$)

MW=482; [ES/MS] m/z 483 [M+1]$^+$; Mp=139° C.

Compound 3: 3,4,5-trimethoxy-N—(N-(3-(3-methoxy-benzamido)phenyl)-carbamimidoyl)benzamide ($C_{25}H_{26}N_4O_5$)

MW=478; [ES/MS] m/z 479 [M+1]$^+$; Mp=118° C.

Compound 4: N-(3-(3-(3,4,5-trimethoxybenzoyl)guanidino)phenyl)biphenyl-4-carboxamide MW=524; [ES/MS] m/z 525 [M+1]$^+$; Mp=134° C.

Compound 5: N—(N-(3-(cyclohexanecarboxamido)phenyl)carbamimidoyl)-3,4,5-trimethoxybenzamide ($C_{24}H_{30}N_4O_5$)

MW=454; [ES/MS] m/z 455 [M+1]$^+$; Mp=168° C.

Compound 6: N-(3-(3-(3,4,5-trimethoxybenzoyl)guanidino)phenyl)-2-naphthamide ($C_{27}H_{26}N_4O_5$)

MW=483; [ES/MS] m/z 484 [M+1]$^+$; Mp=154° C.

Compound 7: N-(3-(3-(3,4,5-trimethoxybenzoyl)guanidino)phenyl)-isonicotinamide ($C_{23}H_{23}N_5O_6$)

MW=449; [ES/MS] m/z 450 [M+1]$^+$; Mp=126° C.

Compound 8: N-(3-(3-(3,4,5-trimethoxybenzoyl)guanidino)phenyl)furan-2-carboxamide ($C_{22}H_{22}N_4O_6$)

MW=438; [ES/MS] m/z 439 [M+1]$^+$; Mp=151° C.

Compound 9: N—(N-(3-benzamidophenyl)carbamimidoyl)-3,5-dimethoxybenzamide ($C_{23}H_{22}N_4O_4$)

MW=418; [ES/MS] m/z 419 [M+1]$^+$; Mp=125° C.

Compound 10: N—(N-(3-benzamidophenyl)carbamimidoyl)-4-ethoxy-3,5-dimethoxybenzamide ($C_{25}H_{26}N_4O_5$)

MW=462; [ES/MS] m/z 463 [M+1]$^+$; Mp=127° C.

Compound 11: N—(N-(3-benzamidophenyl)carbamimidoyl)-3,4-diethoxy-5-methoxybenzamide ($C_{26}H_{28}N_4O_5$)

MW=476; [ES/MS] m/z 477 [M+1]$^+$; Mp=129° C.

Compound 12: N—(N-(3-benzamidophenyl)carbamimidoyl)-7-methoxy-benzo[d][1,3]dioxole-5-carboxamide ($C_{23}H_{20}N_4O_5$)

MW=432; [ES/MS] m/z 433 [M+1]$^+$; Mp=140° C.

Compound 13: N—(N-(3-benzamidophenyl)carbamimidoyl)-2,4-dimethoxybenzamide ($C_{23}H_{22}N_4O_4$)

MW=418; [ES/MS] m/z 419 [M+1]$^+$; Mp=136° C.

Compound 14: N—(N-(3-benzamido-4-fluorophenyl)carbamimidoyl)-3,4,5-trimethoxybenzamide ($C_{24}H_{23}FN_4O_5$)

MW=466; [ES/MS] m/z 467 [M+1]$^+$; Mp=153° C.

Compound 15: N—(N-(3-benzamidophenyl)carbamimidoyl)-3,4,5-trimethoxybenzamide ($C_{24}H_{24}N_4O_5$)
MW=448; [ES/MS] m/z 449 [M+1]$^+$; Mp=138° C.

Compound 16: N—(N-(3-benzamido-4-chlorophenyl)carbamimidoyl)-3,4,5-trimethoxybenzamide ($C_{24}H_{23}ClN_4O_5$)
MW=482; [ES/MS] m/z 483 [M+1]$^+$; Mp=146° C.

Compound 17: N-(2-chloro-5-(3-(3,4,5-trimethoxybenzoyl)guanidino)phenyl)-biphenyl-4-carboxamide
MW=559; [ES/MS] m/z 560 [M+1]$^+$; Mp=177° C.

Compound 18: 3,4,5-trimethoxy-N—(N-(3-(4-morpholinobenzamido)phenyl)-carbamimidoyl)benzamide ($C_{28}H_{31}N_5O_6$)
MW=533; [ES/MS] m/z 531 [M+1]$^+$; Mp=137° C.

Compound 19: N—(N-(3-(1H-indol-2-yl)phenyl)carbamimidoyl)-3,4,5-trimethoxybenzamide ($C_{25}H_{24}N_4O_4$)
MW=444; [ES/MS] m/z 445 [M+1]$^+$; Mp=225° C.

Compound 20: N—(N-(4-chloro-3-(4-methoxyphenylcarbamoyl)phenyl)-carbamimidoyl)-3,4,5-trimethoxybenzamide ($C_{25}H_{25}ClN_4O_6$)
MW=512; [ES/MS] m/z 513 [M+1]$^+$; Mp=105° C.

Compound 21: N—(N-(4-chloro-3-(phenylcarbamoyl)phenyl)carbamimidoyl)-3,4,5-trimethoxybenzamide ($C_{24}H_{23}ClN_4O_5$)
MW=482; [ES/MS] m/z 483 [M+1]$^+$; Mp=142-146° C.

Compound 22: 3,4,5-trimethoxy-N—(N-(4-methyl-3-(phenylcarbamoyl)phenyl)-carbamimidoyl)benzamide
MW=462; [ES/MS] m/z 463 [M+1]$^+$; Mp=114° C.

Compound 23: 4'-fluoro-N-(3-(3-(3,4,5-trimethoxybenzoyl)guanidino)phenyl)-biphenyl-4-carboxamide ($C_{30}H_{27}FN_4O_5$)
MW=542; [ES/MS] m/z 543 [M+1]$^+$; Mp=127° C.

Compound 24: N-(2-methyl-5-(3-(3,4,5-trimethoxybenzoyl)guanidino)phenyl)-biphenyl-4-carboxamide ($C_{31}H_{30}N_4O_5$)
MW=538; [ES/MS] m/z 539 [M+1]$^+$; Mp=155° C.

Compound 25: N-(2-methyl-5-(3-(3,4,5-trimethoxybenzoyl)guanidino)phenyl)-biphenyl-3-carboxamide ($C_{31}H_{30}N_4O_5$)
MW=538; [ES/MS] m/z 539 [M+1]$^+$; Mp=128° C.

Compound 26: N-(2-chloro-5-(3-(3,4,5-trimethoxybenzoyl)guanidino)phenyl)-biphenyl-3-carboxamide
MW=559; [ES/MS] m/z 560 [M+1]$^+$; Mp=142° C.

Compound 27: N—N-(3-benzamido-4-methylphenyl)carbamimidoyl)-3,4,5-trimethoxybenzamide
MW=462; [ES/MS] m/z 463 [M+1]$^+$; Mp=121° C.

Compound 28: N—N-(3-(imidazo[2,1-b]thiazol-6-yl)phenyl)carbamimidoyl)-3,4,5-trimethoxybenzamide ($C_{22}H_{21}N_5O_4S$)
MW=451; [ES/MS] m/z 452 [M+1]$^+$; Mp=74° C.

Compound 29: N—(N-(3-(1H-indol-1-yl)phenyl)carbamimidoyl)-3,4,5-trimethoxybenzamide ($C_{25}H_{24}N_4O_4$)
MW=444; [ES/MS] m/z 445 [M+1]$^+$; Mp=163° C.

Compound 30: 4'-fluoro-N-(2-methyl-5-(3-(3,4,5-trimethoxybenzoyl)-guanidino)phenyl)biphenyl-4-carboxamide ($C_{31}H_{29}FN_4O_5$)
MW=556; [ES/MS] m/z 557 [M+1]$^+$; Mp=121° C.

Compound 31: 3,4,5-trimethoxy-N—(N-(4-methyl-3-(4-(pyridin-4-yl)-benzamido)phenyl)carbamimidoyl)-benzamide ($C_{30}H_{29}ClN_5O_5$)
MW=539; [ES/MS] m/z 540 [M+1]$^+$; Mp=156° C.

Compound 32: N—(N-(4-chloro-3-(4-phenoxybenzamido)phenyl)-carbamimidoyl)-3,4,5-trimethoxybenzamide ($C_{30}H_{27}ClN_4O_6$)
MW=575; [ES/MS] m/z 576 [M+1]$^+$; Mp=132° C.

Compound 33: N-(3-(3-benzoylguanidino)phenyl)biphenyl-4-carboxamide ($C_{27}H_{22}N_4O_2$)
MW=434; [ES/MS] m/z 435 [M+1]$^+$; Mp=148° C.

Compound 34: N-(2-methyl-3-(3-(3,4,5-trimethoxybenzoyl)guanidino)phenyl)-biphenyl-4-carboxamide ($C_{31}H_{30}N_4O_5$)
MW=538; [ES/MS] m/z 539 [M+1]$^+$; Mp=125° C.

Compound 35: N-(4-methyl-3-(3-(3,4,5-trimethoxybenzoyl)guanidino)phenyl)-biphenyl-4-carboxamide ($C_{31}H_{30}N_4O_5$)
MW=538; [ES/MS] m/z 539 [M+1]$^+$; Mp=132° C.

Compound 36: N—(N-(3-benzamidophenyl)carbamimidoyl)benzamide ($C_{22}H_{20}N_4O_2$)
MW=372; [ES/MS] m/z 373 [M+1]$^+$; Mp=127° C.

Compound 37: N—(N-(3-(3-biphenyl-4-ylureido)phenyl)carbamimidoyl)-3,4,5-trimethoxybenzamide ($C_{30}H_{29}N_5O_5$)
MW=539; [ES/MS] m/z 540 [M+1]$^+$; Mp=173° C.

Compound 38: N—(N-(4-chloro-3-(3-phenylureido)phenyl)carbamimidoyl)-3,4,5-trimethoxybenzamide ($C_{24}H_{25}N_5O_5$)
MW=463; [ES/MS] m/z 464 [M+1]$^+$; Mp=147° C.

Example 2

Demonstration of the Modulatory Effect of the Compounds of Formula (1) on the Hedgehog Protein Signaling Pathway and of the Binding thereof to the Smoothened Receptor The effect of the compounds of formula (I) in accordance with the invention on inhibition of the Hedgehog protein signaling pathway was determined in vitro by analysis of the differentiation of the pluripotent fibroblast cell line C3H10T1/2 (ATCC) after activation of this pathway in these cells using a synthetic activator: SAG. The in vivo activity of one of the compounds was demonstrated on the cells of the subventricular zone of the adult mouse brain after stereotaxic injection in the presence of the Sonic Hedgehog protein. The capacity of the compounds of formula (I) to bind to the mouse Smoothened receptor was also determined by competition with bodipycyclopamine, a fluorescent compound derived from cyclopamine which binds to the transmembrane domains of the receptor, as described by Chen et al., Genes Dev., 2002, 16, 2743.

1) Materials and Methods 1) 1—Inhibition of the Hedgehog Pathway by the Compounds of Formula (I)

The compounds of formula (I) to be tested were dissolved in dimethyl sulfoxide until a concentration of 10 mM was obtained, and then stored at a temperature of −20° C. until use.

The pluripotent fibroblast cell line C3H10T1/2 was cultured under the conditions recommended by the American Type Culture Collection (ATCC). These cells were activated using 0.1 μM of SAG according to the methods described by Chen et al., Proc. Natl. Acad. Sci. USA, 2002, 99, 14071 and Frank-Kamenetsky et al., J. Biol., 2002, 1, 10.

Activation with SAG causes the cell line to differentiate and allows the cells to express alkaline phosphatase. It was thus possible to measure the activity of the Hedgehog protein signaling pathway by measuring the alkaline phosphatase activity.

The C3H10T1/2 cells were seeded onto 96-well plates at a density of 5×10$^3$ cells per well, 24 hours before the addition of the test compounds at a concentration ranging from 1 nM to 30 μM and in the presence of 0.1 μM of SAG, using DMEM (Dulbecco's Modified Eagle's Medium) with 10% fetal calf serum, as culture medium. The tests were carried out in quadruplicate. The plates were then incubated for 5 to 6 days at a temperature of 37° C. under an atmosphere of 5% $CO_2$. The cells were then washed in a cold phosphate buffer (Phosphate Buffered Saline: PBS), and then lysed by sonication at 4° C. in 50 μL of solution containing 0.9% of NaCl and 0.2% of Triton X-100.

By way of comparison, the activity of other known inhibitors of the Hedgehog protein signaling pathway:

CURIS 61414 (Cur61414), as described, for example, by Frank-Kamenetsky M. et al., J. Biol., 2002, 1, 10, and corresponding to the following formula:

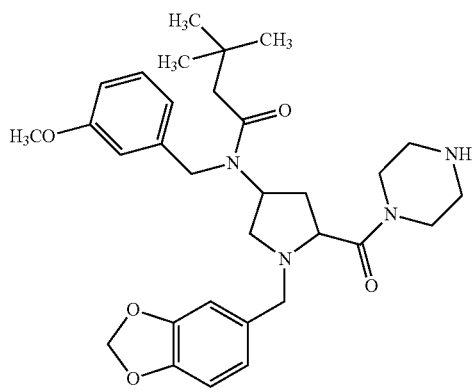 [SMILES: COc1cccc(CN(C(=O)CC(C)(C)C)C2CC(C(=O)N3CCNCC3)N(Cc3ccc4c(c3)OCO4)C2)c1]

cyclopamine, as described by Indardona et al., Development, 1998, 125, 3553, and corresponding to the following formula:

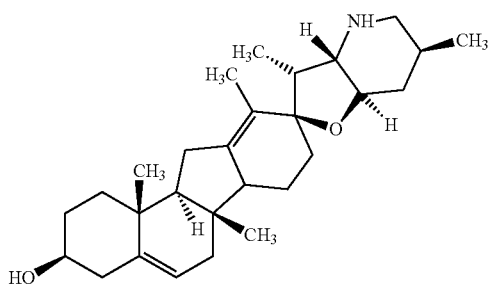

GDC-0449, as described by Miller-Moslin et al., J. Med. Chem., 2009, 52, 3954-3968, of formula:

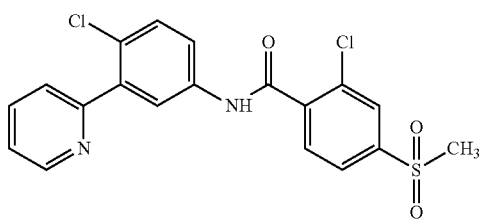 [SMILES: CS(=O)(=O)c1ccc(C(=O)Nc2ccc(Cl)c(-c3ccccn3)c2)c(Cl)c1]

were tested under the same conditions as those used to test the various compounds of formula (I) in accordance with the invention.

The measurement of the alkaline phosphatase activity in the resulting lysates was then carried out according to the method described by Pepinsky et al. (J. Biol. Chem., 1998, 273, 14037). After the addition of 100 μl of reaction buffer (200 mM Tris-HCl; pH 10.5; 0.4 M of 2-amino-2-methylpropanol and 8 mM of $MgCl_2$) and of 50 μl of substrate (4 mM of disodium p-nitrophenylphosphate), the lysates were incubated at 37° C. for 30 to 60 minutes, and then the optical density was read at a wavelength of 415 nm.

1) 2—Competition of the Compounds of Formula (I) with Bodipycyclopamine

Figure 2:
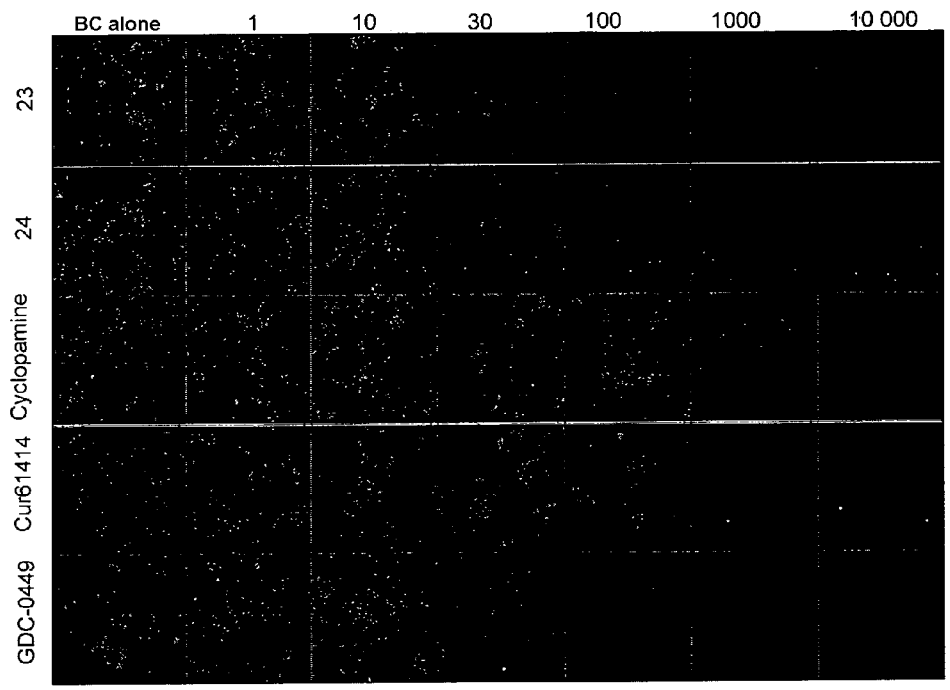
FIG. 2 represents a series of photos taken with a fluorescence microscope, showing the competition of the compounds of formula (I) with bodipycyclopamine.

HEK293 cells are seeded at 70 000 cells per well onto glass cover slips treated with poly-D-lysine in a 24-well plate, and transfected the following day with 0.25 μg of plasmid encoding the mouse Smoothened protein using 0.7 μl of Fugene6 (Roche biochemicals) according to the protocol described by the supplier (i.e. 0.7 μl of Fugene 6 are added to 24 μl of DMEM without any additive, in each well. The mixture is then incubated for 5 minutes at ambient temperature, 0.25 μg of plasmid DNA are added, and then the whole is mixed and incubated for 20 to 30 minutes at ambient temperature. 25 μl of the mixture thus prepared are then added directly to the cell culture medium, in each well of the plate containing 24 wells). After 48 hours, the culture medium is removed, and the cells are rinsed once with 1 ml of a PBS (Phosphate Buffered Saline) phosphate buffer solution, and then fixed for 20 minutes in the presence of an ice-cold solution of paraformaldehyde (PFA) at 4%, and 0.12 M glucose in a PBS phosphate buffer solution. The cells are then rinsed once and washed twice for 5 minutes with 1 ml of a PBS phosphate buffer solution containing 0.5% of fetal calf serum (PBS-FCS). Next, 1 ml of bodipycyclopamine (BC) (Chen, J. K., Taipale, J., Cooper, M. K., and Beachy, P. A., Genes Dev., 2002, 16(21), 2743-2748), diluted to 5 nM in PBS-FCS, in the presence or absence of increasing concentrations of the test compounds, is applied to the cells for 2 hours at 37° C. The cells are then washed twice for 5 minutes with 1 ml of PBS-FCS, then brought into contact with 1 ml of a 1×PBS phosphate buffer solution. Finally, the cover slips are mounted on a glass slide in the presence of Vectashield containing DAPI (4',6'-diamidino-2-phenylindole) so as to label the cell nuclei (Vector). Series of three photos per cover slip are taken with a fluorescence microscope (DMRXA2, Leica; software openlab3.1.2, improvision) (FIG. 2). The fluorescence intensity is then analyzed using the Simple PCI 6.2 software (Hamamatsu Corporation), and then related to the surface area of the nuclei present on the photograph. This intensity depends on the inhibition of the bodipycyclopamine by the compounds analyzed.

1) 3—Inhibitory Activity of the Compounds of Formula (I) In Vivo with Respect to the Activation of the Shh Pathway in the Neural Precursor Niches in the Mouse Brain Adult male Swiss mice (8 weeks old, 35 g) were anesthetized with a mixture of ketamine (Mérial®, Lyon, France) (0.1 mg/g) and xylazine (Bayer®, Puteaux, France) (0.01 mg/g) by intraperitoneal (i. p.) injection. The recombinant Shh protein (290 ng in a buffer solution containing 150 mM of sodium chloride NaCl and 0.5 mM of dithitheritol DTT), was diluted in 4.5 μl of a solution of 2-hydroxypropyl-beta-cyclodextrin (HBC) at 45% in PBS optionally containing 4.5 pmol of Cur61414 or of compound 24. This mixture was injected stereotaxically into the right lateral ventricle (LV) (n=5 animals for each group), at the following coordinates given relative to the Bregma axis: anteroposterior+0.2 mm; lateral+0.8 mm; dorsoventral−2.5 mm. The reference atlas for the stereotaxic coordinates is: *The mouse brain in stereotaxic coordinates*, Georges Paxinos, Keith B. J., Franklin, $2^{nd}$ edition, 2001, Academic Press (San Diego, United States).

The detection of the Patched messenger RNA by in situ hybridization was carried out 48 hours after the injection, as described by Traiffort et al., Eur. J. Neursci, 1999, 11, 3199-3214.

2) Results 2) 1—Inhibition of the Hedgehog Pathway by the Compounds of Formula (I)

Results obtained with compounds of formula (I) are reported in table 1 hereinafter. For each of the compounds, the concentration which makes it possible to inhibit 50% of the alkaline phosphatase activity ($IC_{50}$) after induction with 0.1

µM SAG was evaluated. In this table, the letter A corresponds to an $IC_{50}$ between 3 and 30 nM. The letter B corresponds to an $IC_{50}$ between 30 and 300 nM and the letter C to an $IC_{50}$ between 300 and 1000 nM.

TABLE 1

| COMPOUNDS | $IC_{50}$ (µM) |
|---|---|
| Cur61414* | C |
| Cyclopamine* | C |
| GDC-0449* | A |
| 15 | C |
| 16 | C |
| 17 | B |
| 18 | B |
| 19 | B |
| 20 | C |
| 21 | C |
| 22 | B |
| 23 | A |
| 24 | A |
| 28 | C |
| 29 | C |
| 30 | A |

*Reference compounds which are not part of the invention 2) 2—Competition of the Compounds of Formula (I) with Bodipycyclopamine The incubation in the presence of increasing concentrations of compounds is reflected by a gradual inhibition of the binding of bodipycyclopamine to the cells transfected with the Smoothened receptor, and therefore of the fluorescence observed. FIG. 2 shows an example of a competition experiment carried out in parallel for cyclopamine, Cur61414, GDC-0449 and Compounds 23 and 24.

Figure 3:
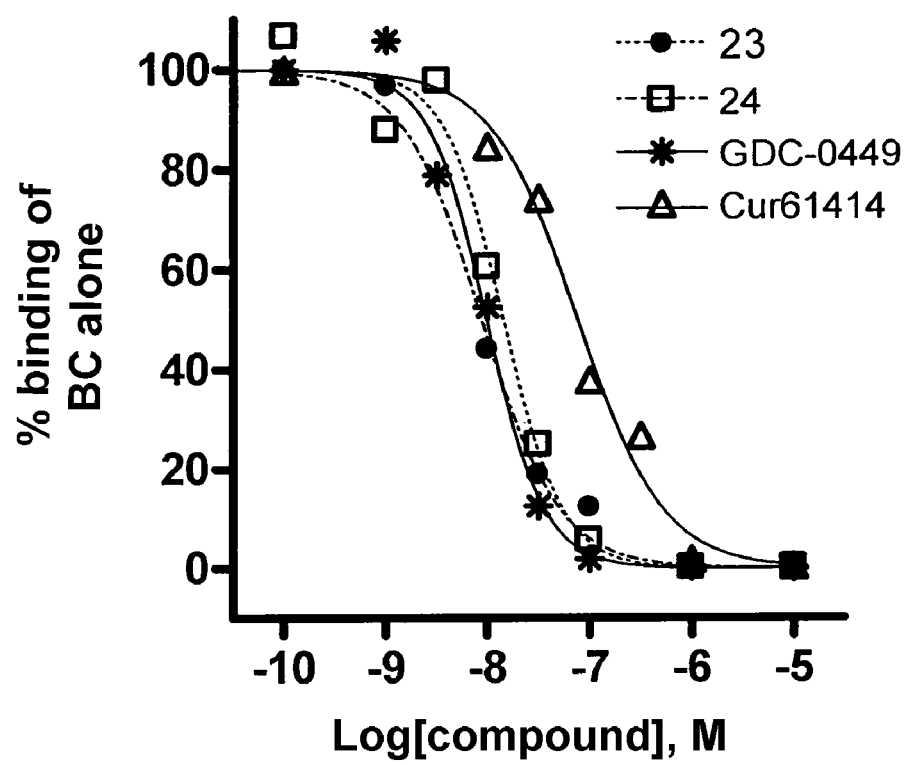
FIG. 3 represents the inhibition curves for compounds 23 and 24, Cur61414 and GDC-0449, on bodipycyclopamine.

Three competition experiments were carried out independently, and the corresponding inhibition curves were plotted in FIG. 3. The concentration which makes it possible to inhibit 50% of the bodipycyclopamine binding ($IC_{50}$) for the compounds of formula (I) and the reference compounds was measured. The results obtained are reported in table 2 hereinafter. In this table, the letter A corresponds to an $IC_{50}$ between 3 and 30 nM and the letter B corresponds to an $IC_{50}$ of between 30 and 300 nM.

TABLE 2

| COMPOUNDS | $IC_{50}$ (µM) |
|---|---|
| Cur61414* | B |
| Cyclopamine* | B |
| GDC-0449* | A |
| 23 | A |
| 24 | A |

*Reference compounds which are not part of the invention

These results show that the compounds of formula (I) in accordance with the invention are modulators of the Hedgehog protein signaling pathway and that they bind to the Smoothened receptor. They are consequently of use for the treatment of pathological conditions requiring blocking of the Hedgehog pathway, such as cancer, or for the treatment of pathological conditions requiring modulation of the Hedgehog pathway, such as neurodegenerative diseases and diabetes.

Some of these compounds demonstrate an affinity which is equal to, or even greater than, that of GDC-0449 which is currently in the clinical phase.

Figure 4:
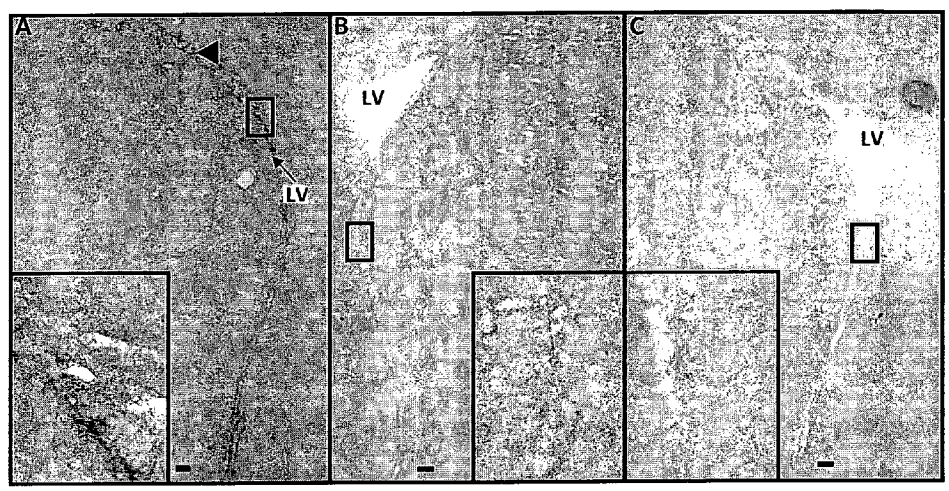
FIG. 4 represents a frontal section of the subventricular zone (SVZ) of brains of adult mice hybridized with an antisense riboprobe for the Ptc gene. The sections stem from mice having received the recombinant ShhN protein alone (A), in the presence of Cur61414 (B), or in the presence of compound 24 (C). The arrow shows specific labeling of the Ptc mRNA. The scale bar corresponds to 0.1 mm. Three to five brain sections are hybridized for each condition.

2) 3—Inhibitory Activity of the Compounds of Formula (I) In Vivo with Respect to Activation of the Shh Pathway in the Neural Precursor Niches in the Mouse Brain Injection of the recombinant Sonic Hedgehog protein into the mouse brain lateral ventrical makes it possible to stimulate the Shh pathway in the subventricular zone (SVZ), a region which contains the stem cells and the neural precursors in the mammalian brain (Charytoniuk et al., 2002; Loulier et al., 2006; Angot et al., 2008). These cells are capable of generating new neurons and new glial cells. The regulation of these proliferating cells in the mature brain involves the Shh signaling pathway (Ahn and Joyner, Nature, 2005, 437, 894-897). The involvement of the Shh pathway in the development of central nervous system tumors can be explained by modifications of the activity of the pathway in the regions of neurogenesis in the adult brain. Thus, blocking of the Shh signaling pathway in this niche of neurogenesis can be considered to be a good indication of the antagonist activity of a molecule. The injection of Shh into the lateral ventricle is reflected by the induction of target genes including Gli1 and Patched (Ptc). The induction of the Ptc gene messenger RNA was measured by in situ hybridization using a specific riboprobe. This induction is visible following injection of the recombinant protein alone, but disappears when compound 24 or Cur61414 is added to this protein (FIG. 4, which demonstrates a decrease in the activity of the ShhN protein on the expression of Patched in the subventricular zone of mice in the presence of compound 24 and of Cur61414 (A, B, C)).

These results demonstrate the capacity of the compounds of formula (I) and of Cur61414 to inhibit the Shh pathway in vivo in adult rodents, and suggest the involvement of the Smoothened protein, which is expressed in the neural precursors, in this inhibition.

All of the experiments carried out bring to light the capacity of the compounds of formula (I) to modulate the Shh pathway both in vitro and in vivo. The activity thereof could be explained by binding to the Smoothened protein on a competing site for bodipycyclopamine.

The invention claimed is:
1. Compounds corresponding to formula (I) below:

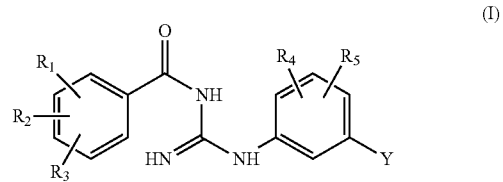

in which:
R$_1$, R$_2$ and R$_3$, which may be identical or different, and independently of one another, are selected from the group consisting of:
a hydrogen or halogen atom,
a hydroxyl radical,
an alkyl group,
a perfluoroalkyl group,
an optionally substituted alkoxy group,
an alkylthio group,
a nitrile group, and
a heterocycle obtained from two of R$_1$, R$_2$ and R$_3$ which are fused with two adjacent carbon atoms of the phenyl ring to which they are bonded;
Y is selected in the group consisting of:
a monocyclic or polycyclic heteroaryl group chosen from indole or imidazole fused to a thiazole group,
—NH—(C=O)—R$_6$,
—(C=O)—NH—R$_6$ and
—NH—(C=O)—NH—R$_6$,
in which R$_6$ is selected from the group consisting of:
an unsubstituted monocyclic or polycyclic aryl group;
an aryl group comprising one or more substituents selected from the group consisting of a halogen atom, an alkyl radical, an alkoxy radical, an alkoxyaryl radical, monoalkylamino or dialkylamino radical, an aryl group, an heteroaryl group and a heterocycle;
monocyclic or polycyclic heteroaryl group;
a linear or branched alkyl radical; and
a saturated or unsaturated, monocyclic or polycyclic hydrocarbon-based group;

$R_4$ and $R_5$, which may be identical or different, and independently of one another, are selected from the group consisting of a hydrogen atom, a halogen atom, an alkoxy group, an alkylthio group, an alkyl group, a perfluoroalkyl group, a nitrile group and a nitro group, as medicaments.

2. The compounds of formula (I) as claimed in claim 1, wherein the compounds are chosen from those in which:

$R_1$, $R_2$ and $R_3$, which may be identical or different, represent a hydrogen atom, a methyloxy or ethyloxy radical, or a dioxolane fused with two adjacent carbon atoms of the phenyl ring to which they are bonded;

$R_4$ and $R_5$, which may be identical or different, represent a hydrogen, chlorine, bromine or fluorine atom, or a methyl or methoxy radical; and Y represents a monocyclic or polycyclic heteroaryl group, —NH—(C=O)—$R_6$, —(C=O)—NH—$R_6$ or —NH—(C=O)—NH—$R_6$ in which $R_6$ represents:

a phenyl group, optionally substituted with a halogen atom, an alkyl, diaminoalkyl or alkoxy radical, a cycloalkyl group, or an aryl group;
a cycloalkyl group;
a pyridinyl group;
a naphthyl group;
a furyl group;
a thiophenyl group; or
an isopropyl radical.

3. The compounds of formula (I) as claimed in claim 2, wherein said group Y is chosen from indole or imidazole fused to a thiazole group, when said group Y represents a monocyclic or polycyclic heteroaryl group.

4. The compounds of formula (I) as claimed in claim 2, wherein $R_6$ represents:

a phenyl group, optionally substituted with a chlorine atom, a methoxy radical, a morpholine, or a phenyl or phenoxy group;
a cyclohexyl group;
a pyridinyl group;
a naphthyl group; or
a furyl group, when said group Y represents an —NH—(C=O)—$R_6$, —(C=O)—NH—$R_6$ or —NH—(C=O)—NH—$R_6$ group.

5. The compounds of formula (I) as claimed in claim 1, wherein the compounds are selected from the group consisting of:

3,4,5-trimethoxy-N—(N-(3-(4-methoxybenzamido)phenyl)carbamimidoyl)benzamide:

(Compound 1)

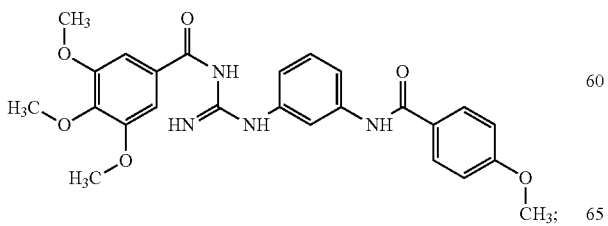

N—(N-(3-(2-chlorobenzamido)phenyl)carbamimidoyl)-3,4,5-trimethoxybenzamide:

(Compound 2)

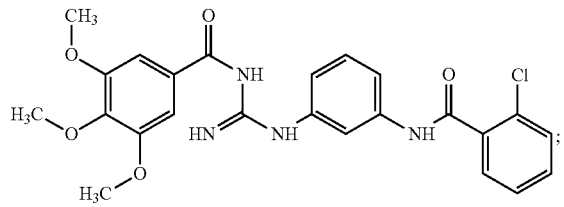

3,4,5-trimethoxy-N—(N-(3-(3-methoxybenzamido)phenyl)carbamimidoyl)benzamide:

(Compound 3)

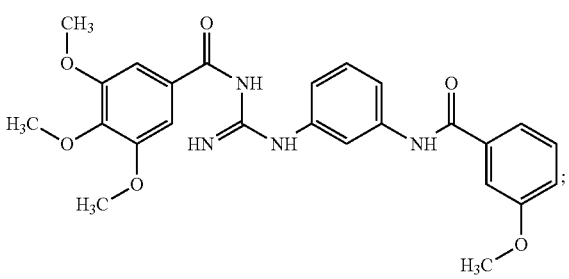

N-(3-(3-(3,4,5-trimethoxybenzoyl)guanidino)phenyl)biphenyl-4-carboxamide:

(Compound 4)

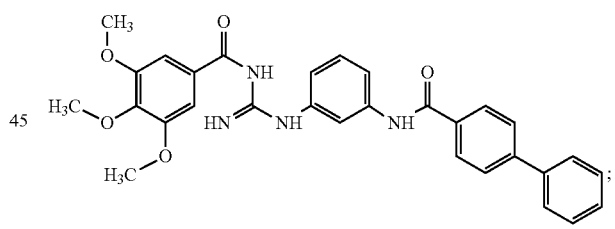

N—(N-(3-(cyclohexanecarboxamido)phenyl)carbamimidoyl)-3,4,5-trimethoxybenzamide:

(Compound 5)

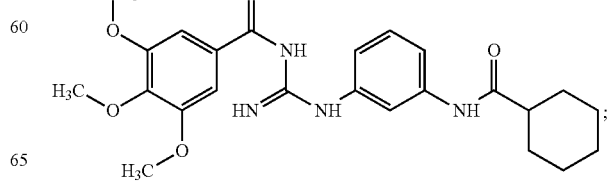

N-(3-(3-(3,4,5-trimethoxybenzoyl)guanidino)phenyl)-2-naphthamide:

(Compound 6)

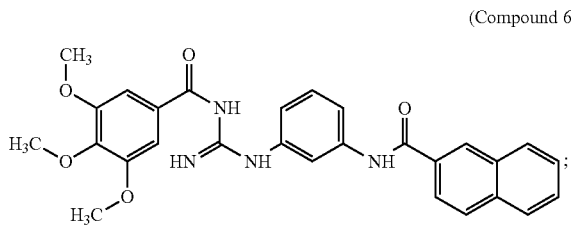

N-(3-(3-(3,4,5-trimethoxybenzoyl)guanidino)phenyl)isonicotinamide:

(Compound 7)

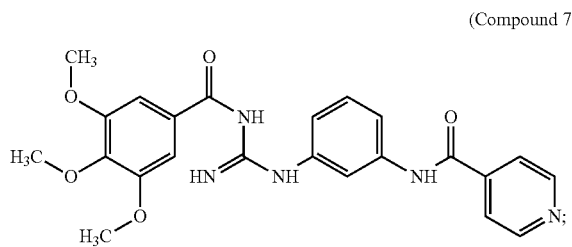

N-(3-(3-(3,4,5-trimethoxybenzoyl)guanidino)phenyl)furan-2-carboxamide:

(Compound 8)

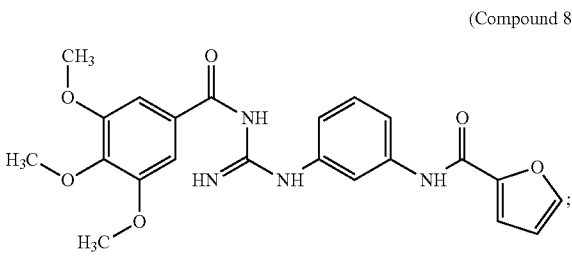

N—(N-(3-benzamidophenyl)carbamimidoyl)-3,5-dimethoxybenzamide:

(Compound 9)

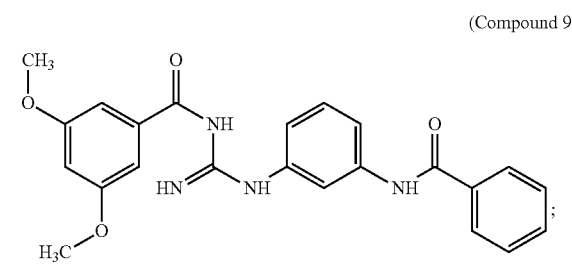

N—(N-(3-benzamidophenyl)carbamimidoyl)-4-ethoxy-3,5-dimethoxybenzamide:

(Compound 10)

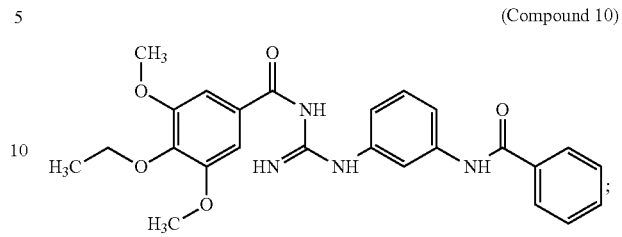

N—(N-(3-benzamidophenyl)carbamimidoyl)-3,4-diethoxy-5-methoxybenzamide:

(Compound 11)

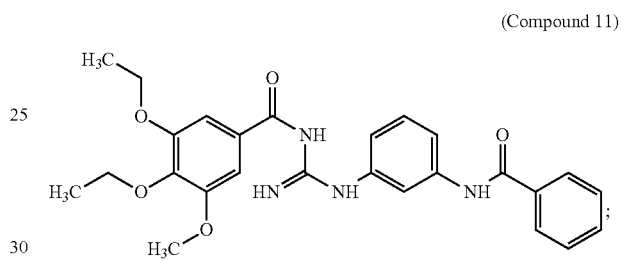

N—(N-(3-benzamidophenyl)carbamimidoyl)-7-methoxybenzo[d][1,3]dioxole-5-carboxamide:

(Compound 12)

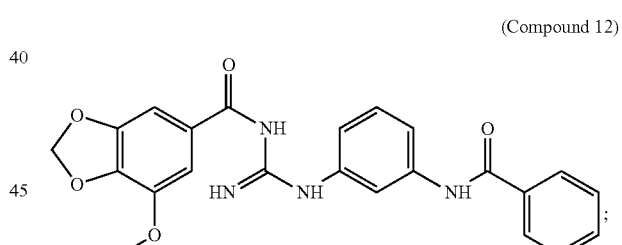

N—(N-(3-benzamidophenyl)carbamimidoyl)-2,4-dimethoxybenzamide:

(Compound 13)

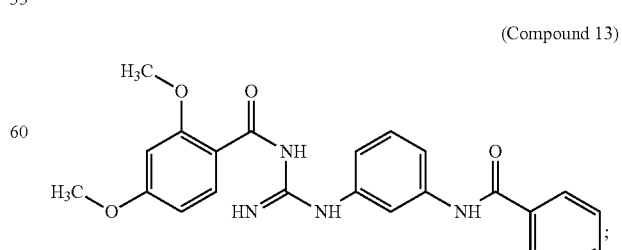

N—(N-(3-benzamido-4-fluorophenyl)carbamimidoyl)-3,4,5-trimethoxybenzamide:

(Compound 14)

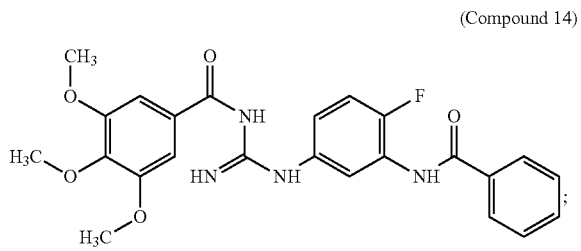 [SMILES: COc1cc(C(=O)NC(=N)Nc2ccc(F)c(NC(=O)c3ccccc3)c2)cc(OC)c1OC]

N—(N-(3-benzamidophenyl)carbamimidoyl)-3,4,5-trimethoxybenzamide:

(Compound 15)

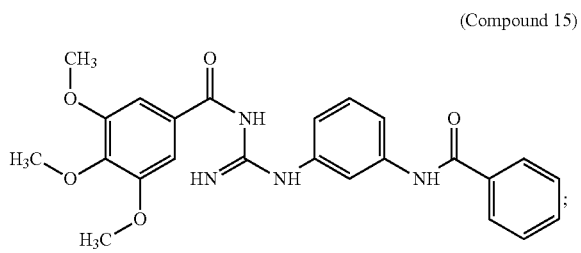 [SMILES: COc1cc(C(=O)NC(=N)Nc2cccc(NC(=O)c3ccccc3)c2)cc(OC)c1OC]

N—(N-(3-benzamido-4-chlorophenyl)carbamimidoyl)-3,4,5-trimethoxybenzamide:

(Compound 16)

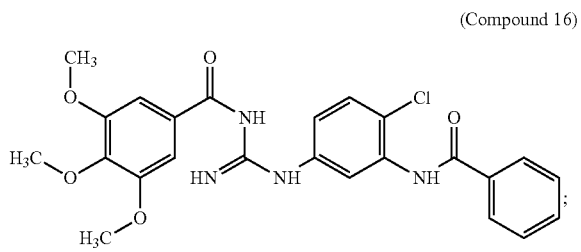 [SMILES: COc1cc(C(=O)NC(=N)Nc2ccc(Cl)c(NC(=O)c3ccccc3)c2)cc(OC)c1OC]

N-(2-chloro-5-(3-(3,4,5-trimethoxybenzoyl)guanidino)phenyl)biphenyl-4-carboxamide:

(Compound 17)

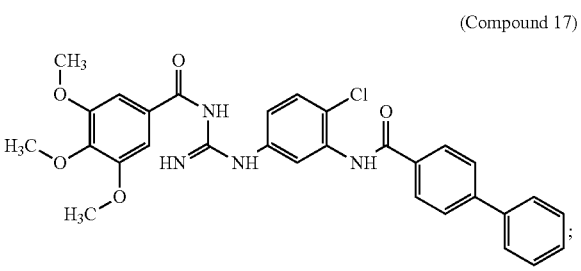 [SMILES: COc1cc(C(=O)NC(=N)Nc2ccc(Cl)c(NC(=O)c3ccc(-c4ccccc4)cc3)c2)cc(OC)c1OC]

3,4,5-trimethoxy-N—(N-(3-(4-morpholinobenzamido)phenyl)carbamimidoyl)benzamide:

(Compound 18)

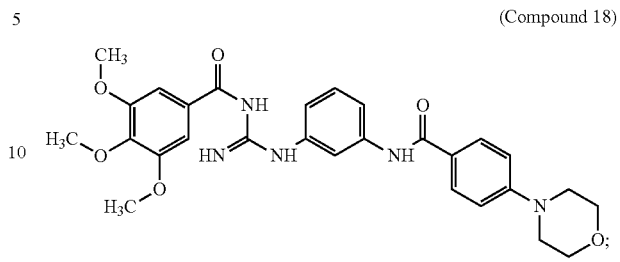

N—(N-(3-(1H-indol-2-yl)phenyl)carbamimidoyl)-3,4,5-trimethoxybenzamide:

(Compound 19)

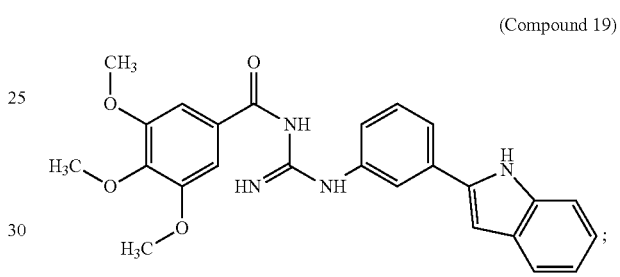

N—(N-(4-chloro-3-(4-methoxyphenylcarbamoyl)phenyl)carbamimidoyl)-3,4,5-trimethoxybenzamide:

(Compound 20)

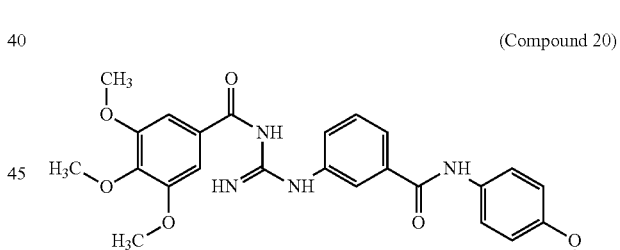

N—(N-(4-chloro-3-(phenylcarbamoyl)phenyl)carbamimidoyl)-3,4,5-trimethoxybenzamide:

(Compound 21)

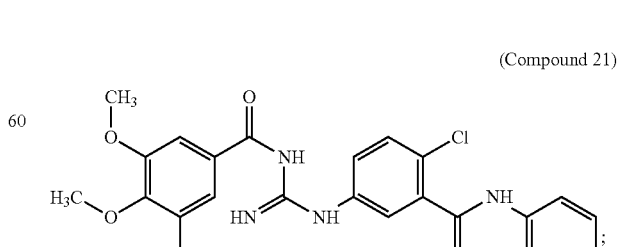

3,4,5-trimethoxy-N—(N-(4-methyl-3-(phenylcarbamoyl)phenyl)carbamimidoyl)benzamide:

(Compound 22)

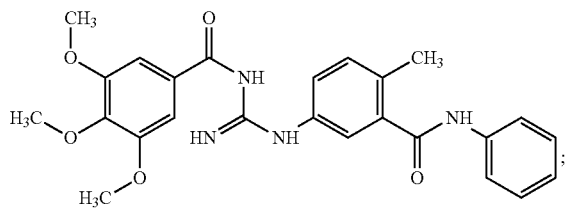

4'-fluoro-N-(3-(3-(3,4,5-trimethoxybenzoyl)guanidino)phenyl)biphenyl-4-carboxamide:

(Compound 23)

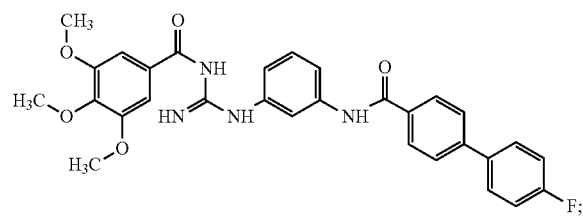

N-(2-methyl-5-(3-(3,4,5-trimethoxybenzoyl)guanidino)phenyl)biphenyl-4-carboxamide:

(Compound 24)

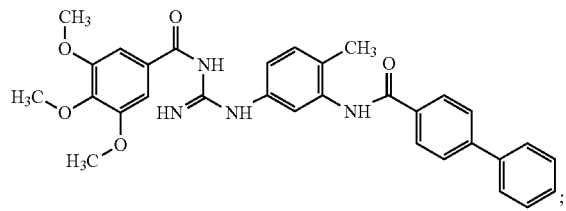

N-(2-methyl-5-(3-(3,4,5-trimethoxybenzoyl)guanidino)phenyl)biphenyl-3-carboxamide:

(Compound 25)

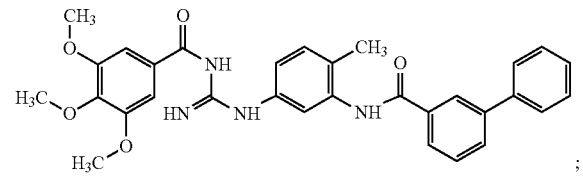

N-(2-chloro-5-(3-(3,4,5-trimethoxybenzoyl)guanidino)phenyl)biphenyl-3-carboxamide:

(Compound 26)

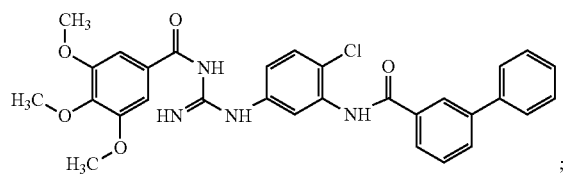

N—N-(3-benzamido-4-methylphenyl)carbamimidoyl)-3,4,5-trimethoxybenzamide:

(Compound 27)

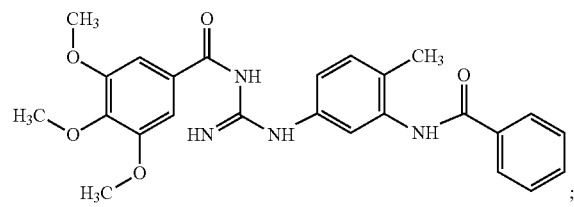

N—N-(3-(imidazo[2,1-b]thiazol-6-yl)phenyl)carbamimidoyl)-3,4,5-trimethoxybenzamide:

(Compound 28)

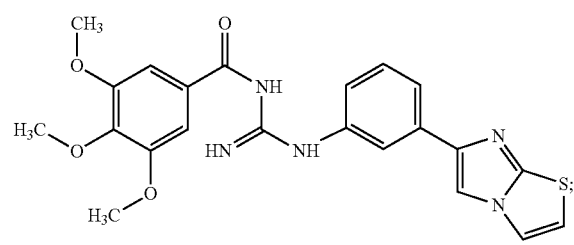

N—(N-(3-(1H-indol-1-yl)phenyl)carbamimidoyl)-3,4,5-trimethoxybenzamide:

(Compound 29)

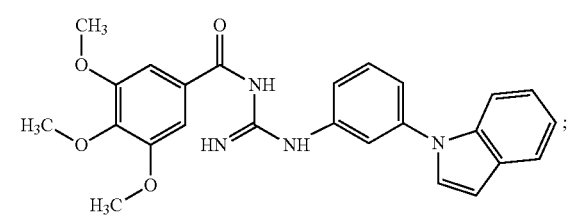

4'-fluoro-N-(2-methyl-5-(3-(3,4,5-trimethoxybenzoyl)guanidino)phenyl)biphenyl-4-carboxamide:

(Compound 30)

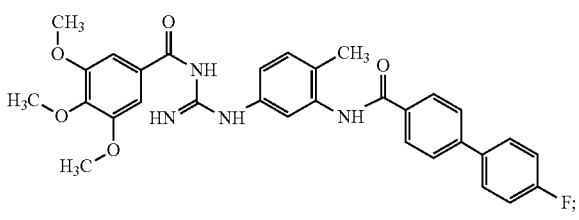

3,4,5-trimethoxy-N—(N-(4-methyl-3-(4-(pyridin-4-yl)benzamido)phenyl)carbamimidoyl)-benzamide:

(Compound 31)

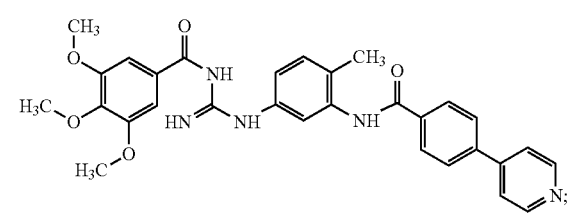

N—(N-(4-chloro-3-(4-phenoxybenzamido)phenyl)carbamimidoyl)-3,4,5-trimethoxybenzamide:

(Compound 32)

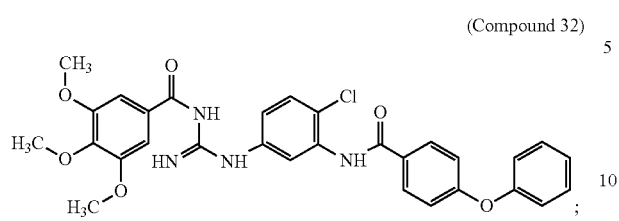

N-(3-(3-benzoylguanidino)phenyl)biphenyl-4-carboxamide:

(Compound 33)

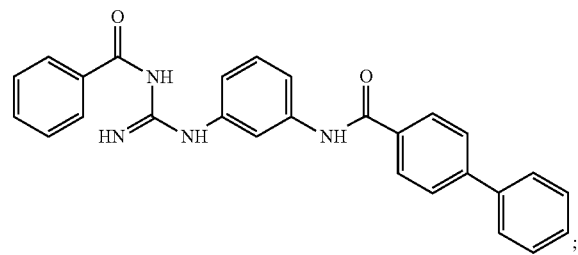

N-(2-methyl-3-(3-(3,4,5-trimethoxybenzoyl)guanidino)phenyl)biphenyl-4-carboxamide:

(Compound 34)

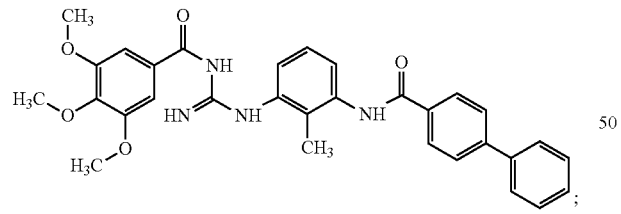

N-(4-methyl-3-(3-(3,4,5-trimethoxybenzoyl)guanidino)phenyl)biphenyl-4-carboxamide:

(Compound 35)

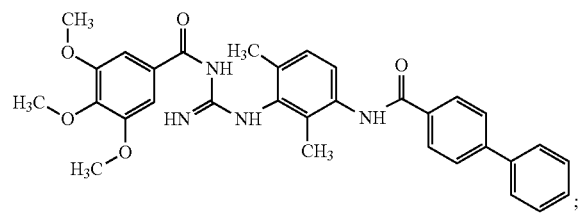

N—(N-(3-benzamidophenyl)carbamimidoyl)benzamide:

(Compound 36)

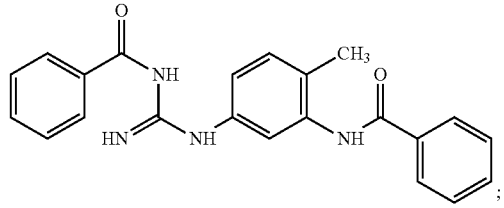

N—(N-(3-(3-biphenyl-4-ylureido)phenyl)carbamimidoyl)-3,4,5-trimethoxybenzamide:

(Compound 37)

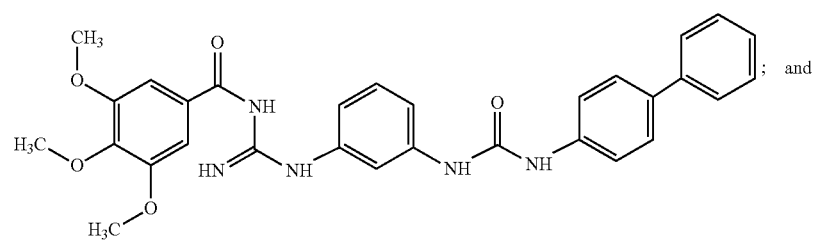

; and

N—(N-(4-chloro-3-(3-phenylureido)phenyl)carbamimidoyl)-3,4,5-trimethoxybenzamide:

(Compound 38)

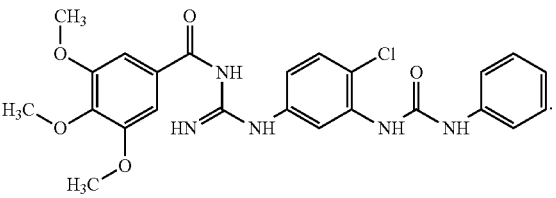

6. The compounds as claimed in claim 5, wherein the compounds are chosen from:
   3,4,5-trimethoxy-N—(N-(3-(4-methoxybenzamido)phenyl)carbamimidoyl)benzamide (Compound 1);
   N—(N-(3-(2-chlorobenzamido)phenyl)carbamimidoyl)-3,4,5-trimethoxybenzamide (Compound 2);
   3,4,5-trimethoxy-N—(N-(3-(3-methoxybenzamido)phenyl)carbamimidoyl)benzamide (Compound 3);
   N-(3-(3-(3,4,5-trimethoxybenzoyl)guanidino)phenyl)-2-naphthamide (Compound 6);
   N-(3-(3-(3,4,5-trimethoxybenzoyl)guanidino)phenyl)furan-2-carboxamide (Compound 8);
   N—(N-(3-benzamidophenyl)carbamimidoyl)-3,5-dimethoxybenzamide (Compound 9);
   N—(N-(3-benzamidophenyl)carbamimidoyl)-7-methoxybenzo[d][1,3]dioxole-5-carboxamide (Compound 12);
   N—(N-(3-benzamidophenyl)carbamimidoyl)-2,4-dimethoxybenzamide (Compound 13);
   N—(N-(3-benzamidophenyl)carbamimidoyl)-3,4,5-trimethoxybenzamide (Compound 15);
   N-(2-chloro-5-(3-(3,4,5-trimethoxybenzoyl)guanidino)phenyl)biphenyl-4-carboxamide (Compound 17);
   N—(N-(3-(1H-indol-2-yl)phenyl)carbamimidoyl)-3,4,5-trimethoxybenzamide (Compound 19);
   N—(N-(4-chloro-3-(phenylcarbamoyl)phenyl)carbamimidoyl)-3,4,5-trimethoxybenzamide (Compound 21);
   4'-fluoro-N-(3-(3-(3,4,5-trimethoxybenzoyl)guanidino)phenyl)biphenyl-4-carboxamide (Compound 23);

N-(2-methyl-5-(3-(3,4,5-trimethoxybenzoyl)guanidino)phenyl)biphenyl-4-carboxamide (Compound 24);

N—(N-(3-(1H-indol-1-yl)phenyl)carbamimidoyl)-3,4,5-trimethoxybenzamide (Compound 29);

4'-fluoro-N-(2-methyl-5-(3-(3,4,5-trimethoxybenzoyl)guanidino)phenyl)biphenyl-4-carboxamide (Compound 30);

N—(N-(4-chloro-3-(4-phenoxybenzamido)phenyl)carbamimidoyl)-3,4,5-trimethoxybenzamide (Compound 32);

N—(N-(4-chloro-3-(3-phenylureido)phenyl)carbamimidoyl)-3,4,5-trimethoxybenzamide (Compound 38).

7. The compounds of formula (I) as claimed in claim 1 wherein the compounds are in the form of salts.

8. The compounds of formula (I) as claimed in claim 7, wherein said salts are formed with hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkanesulfonic acids, such as methanesulfonic acid and ethanesulfonic acid, arylsulfonic acids, such as benzenesulfonic acid and para-toluenesulfonic acid or arylcarboxylic acids.

9. The compounds of formula (I) as claimed in claim 8, wherein said salts are formed with hydrochloric acid.

10. The compounds of formula (I) as claimed in claim 1, for use as a medicament intended for the treatment of tumors associated with hyperactivation of the Hedgehog protein signaling pathway.

11. The compounds of formula (I) as claimed in claim 10, for use as a medicament for the treatment of tumors selected from the group consisting of nervous tissue tumors, skin tumors, muscle tumors, bone tissue tumors, kidney tumors, bladder tumors, prostate tumors, lung tumors, stomach tumors, pancreas tumors, breast tumors, and liver tumors.

12. The compounds of formula (I) as claimed in claim 1, for use as a medicament intended for the treatment of neurodegenerative pathological conditions.

13. The compounds of formula (I) as claimed in claim 12, for use as a medicament for the treatment of Parkinson's disease, Huntington's chorea, Alzheimer's disease, multiplesclerosis and motoneuron disease.

14. The compounds of formula (I) as claimed in claim 1, for use as a medicament intended for the treatment of diseases linked to brain development, for the treatment of strokes and cardiovascular events, and also for diseases of oligodentrocytes and Schwann cells.

15. The compounds of formula (I) as claimed in claim 14, for use in vitro for controlling and modulating the renewal of human or animal stem cells.

16. The compounds of formula (I) as claimed in claim 1, for use as a medicament intended for the treatment of diabetes.

17. The compounds of formula (I) as claimed in claim 1, as markers for detecting the presence of proteins, such as the Smoothened, Patched (Patched 1 and Patched 2), Dispatched (Dispatched 1 and Dispatched 2) and HIP proteins, in tissues or cell lines.

18. The compounds of formula (I) as claimed in claim 1, as diagnostic tools for screening for proteins, such as the Smoothened, Patched (Patched 1 and Patched 2), Dispatched (Dispatched 1 and Dispatched 2) and HIP proteins, in tissues or cell lines.

19. A pharmaceutical composition comprising as active ingredient, at least one compound of formula (I) as defined according to claim 1, and at least one pharmaceutically acceptable excipient.

20. Compounds corresponding to formula (I) below:

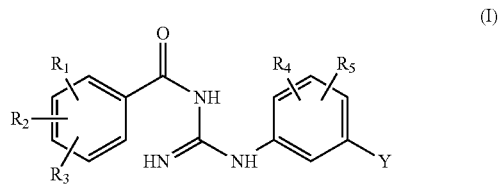

in which:

$R_1$, $R_2$ and $R_3$, which may be identical or different, and independently of one another, are selected from the group consisting of:
a hydrogen or halogen atom,
a hydroxyl radical,
an alkyl group,
a perfluoroalkyl group,
an optionally substituted alkoxy group,
an alkylthio group,
a nitrile group, and
a heterocycle obtained from two of $R_1$, $R_2$ and $R_3$ which are fused with two adjacent carbon atoms of the phenyl ring to which they are bonded;
Y is selected from the group consisting of:
a monocyclic or polycyclic heteroaryl group chosen from indole or imidazole fused to a thiazole group,
—NH—(C=O)—$R_6$,
—(C=O)—NH—$R_6$ and
—NH—(C=O)—NH—$R_6$ in which $R_6$ represents is selected from the group consisting of:
an unsubstituted monocyclic or polycyclic aryl group;
an aryl group comprising one or more substituents selected from the group consisting of a halogen atom, an alkyl radical, an alkoxy radical, an alkoxyaryl radical, a monoalkylamino or dialkylamino radical, an aryl group, an heteroaryl group, and a heterocycle;
a monocyclic or polycyclic heteroaryl group;
a linear or branched alkyl radical; and
a saturated or unsaturated, monocyclic or polycyclic hydrocarbon-based group;

$R_4$ and $R_5$, which may be identical or different, and independently of one another, are selected from the group consisting of a hydrogen atom, a halogen atom, an alkoxy group, an alkylthio group, an alkyl group, a perfluoroalkyl group, a nitrile, and a nitro group.

21. The compounds of formula (I) as claimed in claim 20, wherein the compounds are chosen from those in which:
$R_1$, $R_2$ and $R_3$, which may be identical or different, represent a hydrogen atom, a methyloxy or ethyloxy radical, or a dioxolane fused with two adjacent carbon atoms of the phenyl ring to which they are bonded;
$R_4$ and $R_5$, which may be identical or different, represent a hydrogen, chlorine, bromine or fluorine atom, or a methyl or methoxy radical; and
Y represents:
a monocyclic or polycyclic heteroaryl group selected from the group consisting of an indole, an imidazole fused to a thiazole group; or
an —NH—(C=O)—$R_6$, or —(C=O)—NH—$R_6$ or —NH—(C=O)—NH—$R_6$ group in which $R_6$ represents:
a phenyl group optionally substituted with a halogen atom, an alkyl, diaminoalkyl or alkoxy radical, a cycloalkyl group, or an aryl group;
a cycloalkyl group;
a pyridinyl group;

a naphthyl group;
a furyl group;
a thiophenyl group; or
an isopropyl radical.

22. The compounds of formula (I) as claimed in claim 21, wherein $R_6$ represents:
   a phenyl group optionally substituted with a chlorine atom, a methoxy radical, a morpholine, or a phenyl or phenoxy group;
   a cyclohexyl group;
   a pyridinyl group;
   a naphthyl group; or
   a furyl group,
when said group Y represents an —NH—(C=O)—$R_6$, —(C=O)—NH—$R_6$ or —NH—(C=O)—NH—$R_6$ group.

23. The compounds of formula (I) as claimed in claim 20, wherein the compounds are selected from the group consisting of:

3,4,5-trimethoxy-N—(N-(3-(4-methoxybenzamido)phenyl)carbamimidoyl)benzamide:

(Compound 1)

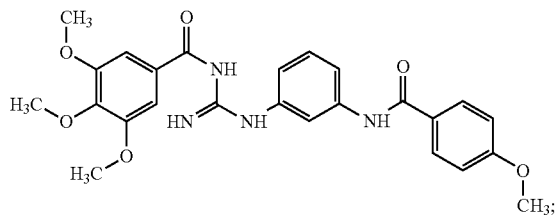

N—(N-(3-(2-chlorobenzamido)phenyl)carbamimidoyl)-3,4,5-trimethoxybenzamide:

(Compound 2)

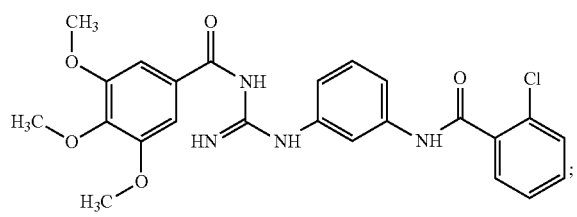

3,4,5-trimethoxy-N—(N-(3-(3-methoxybenzamido)phenyl)carbamimidoyl)benzamide:

(Compound 3)

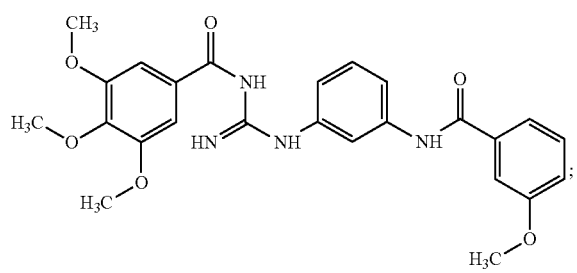

N-(3-(3-(3,4,5-trimethoxybenzoyl)guanidino)phenyl)biphenyl-4-carboxamide:

(Compound 4)

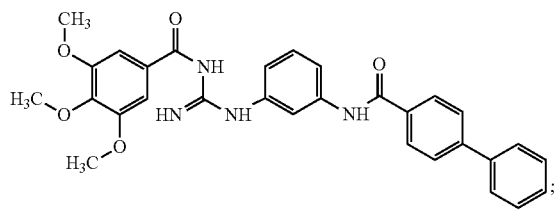

N—(N-(3-(cyclohexanecarboxamido)phenyl)carbamimidoyl)-3,4,5-trimethoxybenzamide:

(Compound 5)

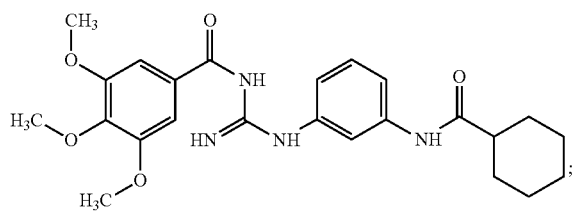

N-(3-(3-(3,4,5-trimethoxybenzoyl)guanidino)phenyl)-2-naphthamide:

(Compound 6)

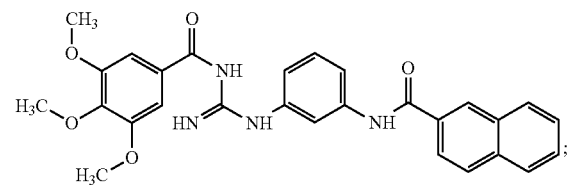

N-(3-(3-(3,4,5-trimethoxybenzoyl)guanidino)phenyl)isonicotinamide:

(Compound 7)

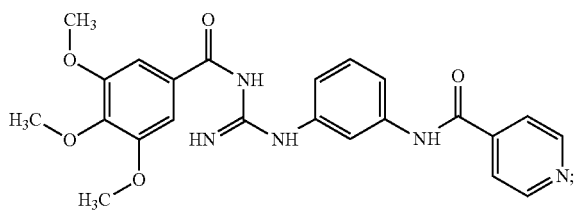

N-(3-(3-(3,4,5-trimethoxybenzoyl)guanidino)phenyl)furan-2-carboxamide:

(Compound 8)

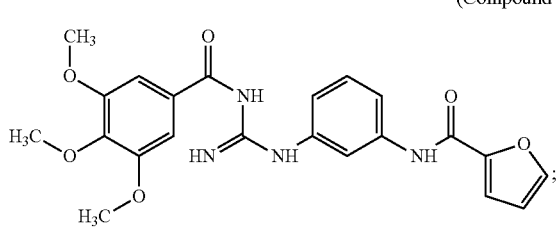

N—(N-(3-benzamidophenyl)carbamimidoyl)-3,5-dimethoxybenzamide:

(Compound 9)

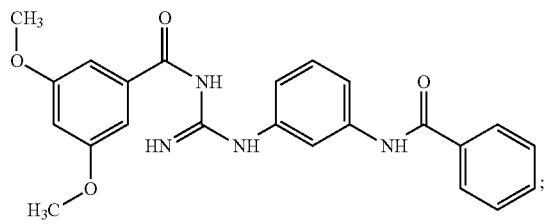

N—(N-(3-benzamidophenyl)carbamimidoyl)-4-ethoxy-3,5-dimethoxybenzamide:

(Compound 10)

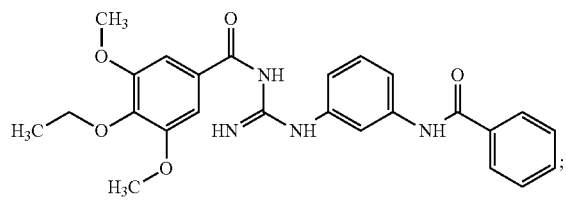

N—(N-(3-benzamidophenyl)carbamimidoyl)-3,4-diethoxy-5-methoxybenzamide:

(Compound 11)

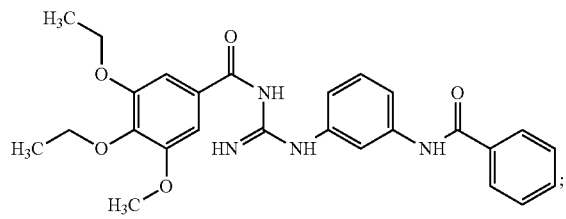

N—(N-(3-benzamidophenyl)carbamimidoyl)-7-methoxybenzo[d][1,3]dioxole-5-carboxamide:

(Compound 12)

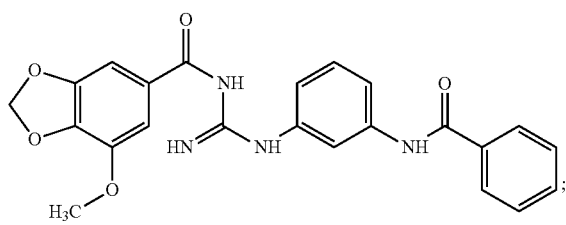

N—(N-(3-benzamidophenyl)carbamimidoyl)-2,4-dimethoxybenzamide:

(Compound 13)

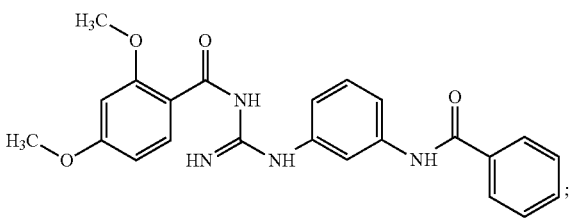

N—(N-(3-benzamido-4-fluorophenyl)carbamimidoyl)-3,4,5-trimethoxybenzamide:

(Compound 14)

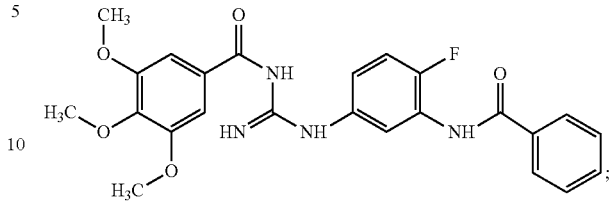

N—(N-(3-benzamidophenyl)carbamimidoyl)-3,4,5-trimethoxybenzamide:

(Compound 15)

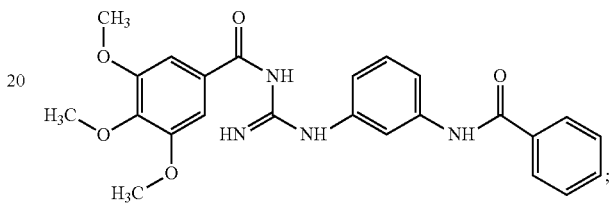

N—(N-(3-benzamido-4-chlorophenyl)carbamimidoyl)-3,4,5-trimethoxybenzamide:

(Compound 16)

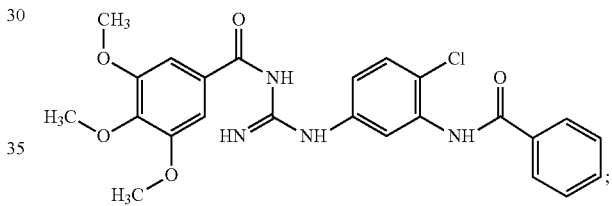

N-(2-chloro-5-(3-(3,4,5-trimethoxybenzoyl)guanidino)phenyl)biphenyl-4-carboxamide:

(Compound 17)

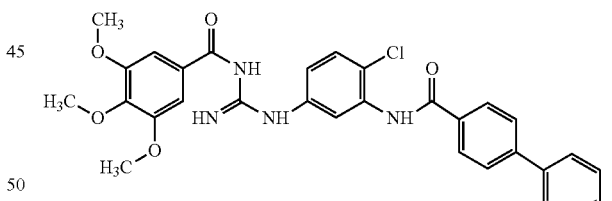

3,4,5-trimethoxy-N—(N-(3-(4-morpholinobenzamido)phenyl)carbamimidoyl)benzamide:

(Compound 18)

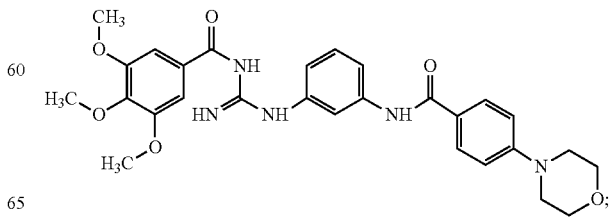

N—(N-(3-(1H-indol-2-yl)phenyl)carbamimidoyl)-3,4,5-trimethoxybenzamide:

(Compound 19)

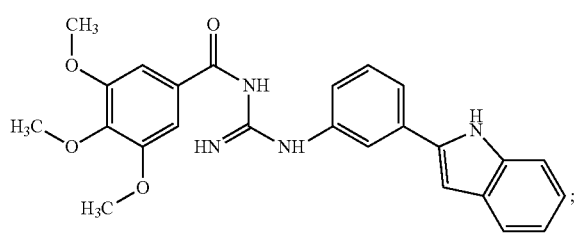

N—(N-(4-chloro-3-(4-methoxyphenylcarbamoyl)phenyl)carbamimidoyl)-3,4,5-trimethoxybenzamide:

(Compound 20)

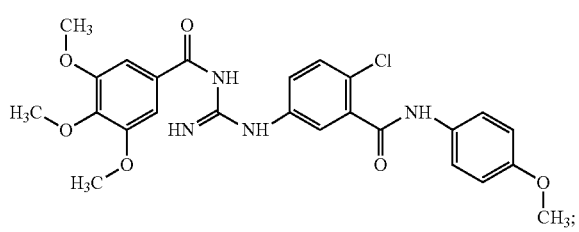

N—(N-(4-chloro-3-(phenylcarbamoyl)phenyl)carbamimidoyl)-3,4,5-trimethoxybenzamide:

(Compound 21)

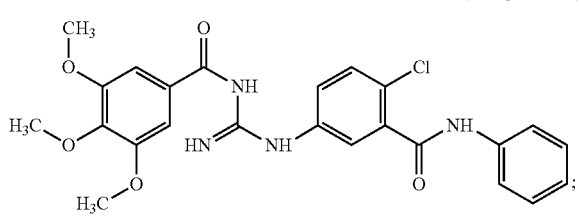

3,4,5-trimethoxy-N—(N-(4-methyl-3-(phenylcarbamoyl)phenyl)carbamimidoyl)benzamide:

(Compound 22)

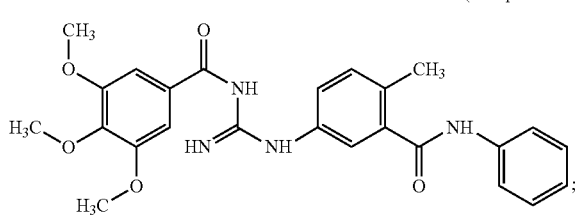

4'-fluoro-N-(3-(3-(3,4,5-trimethoxybenzoyl)guanidino)phenyl)biphenyl-4-carboxamide:

(Compound 23)

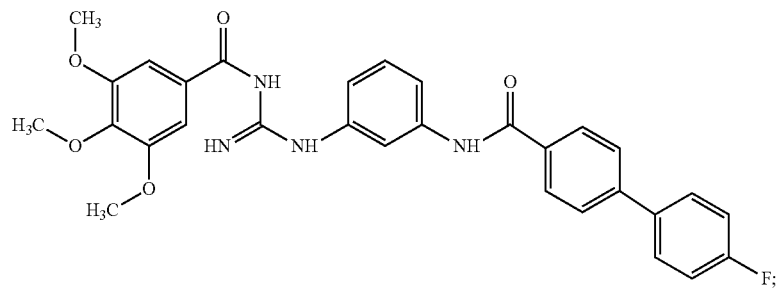

N-(2-methyl-5-(3-(3,4,5-trimethoxybenzoyl)guanidino)phenyl)biphenyl-4-carboxamide:

(Compound 24)

N-(2-methyl-5-(3-(3,4,5-trimethoxybenzoyl)guanidino)phenyl)biphenyl-3-carboxamide:

(Compound 25)

N-(2-chloro-5-(3-(3,4,5-trimethoxybenzoyl)guanidino)phenyl)biphenyl-3-carboxamide:

(Compound 26)

N—N-(3-benzamido-4-methylphenyl)carbamimidoyl)-3,4,5-trimethoxybenzamide:

(Compound 27)

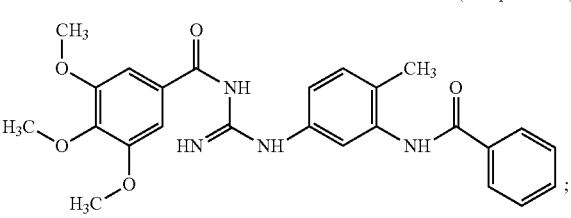

N—N-(3-(imidazo[2,1-b]thiazol-6-yl)phenyl)carbamimidoyl)-3,4,5-trimethoxybenzamide:

(Compound 28)

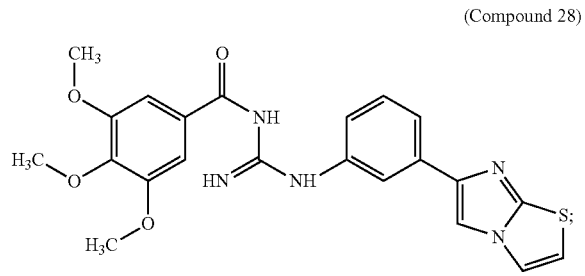 [SMILES: COc1cc(C(=O)NC(=N)Nc2cccc(-c3cn4ccsc4n3)c2)cc(OC)c1OC]

N—(N-(3-(1H-indol-1-yl)phenyl)carbamimidoyl)-3,4,5-trimethoxybenzamide:

(Compound 29)

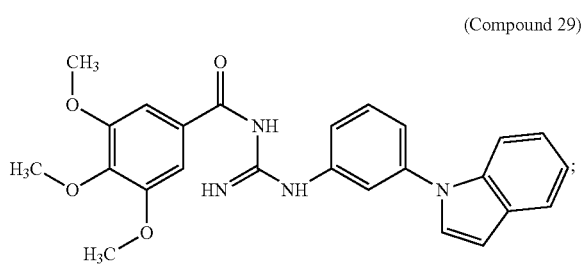 [SMILES: COc1cc(C(=O)NC(=N)Nc2cccc(-n3ccc4ccccc43)c2)cc(OC)c1OC]

4'-fluoro-N-(2-methyl-5-(3-(3,4,5-trimethoxybenzoyl)guanidino)phenyl)biphenyl-4-carboxamide:

(Compound 30)

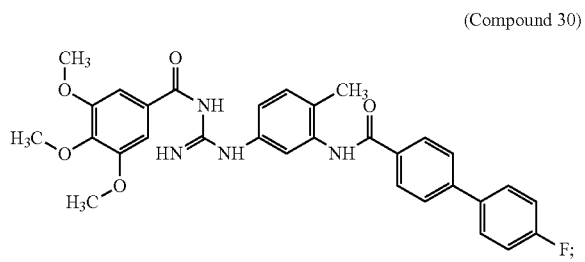 [SMILES: COc1cc(C(=O)NC(=N)Nc2ccc(C)c(NC(=O)c3ccc(-c4ccc(F)cc4)cc3)c2)cc(OC)c1OC]

3,4,5-trimethoxy-N—N-(4-methyl-3-(4-(pyridin-4-yl)benzamido)phenyl)carbamimidoyl)-benzamide:

(Compound 91)

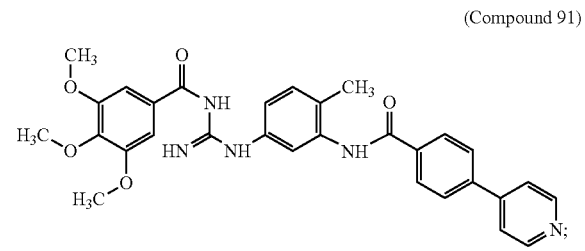 [SMILES: COc1cc(C(=O)NC(=N)Nc2ccc(C)c(NC(=O)c3ccc(-c4ccncc4)cc3)c2)cc(OC)c1OC]

N—(N-(4-chloro-3-(4-phenoxybenzamido)phenyl)carbamimidoyl)-3,4,5-trimethoxybenzamide:

(Compound 32)

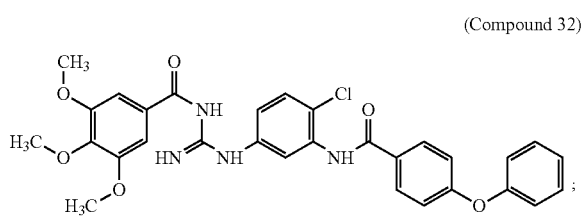 [SMILES: COc1cc(C(=O)NC(=N)Nc2ccc(Cl)c(NC(=O)c3ccc(Oc4ccccc4)cc3)c2)cc(OC)c1OC]

N-(3-(3-benzoylguanidino)phenyl)biphenyl-4-carboxamide:

(Compound 33)

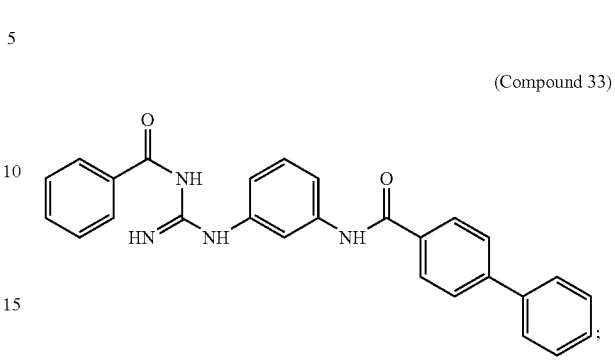

N-(2-methyl-3-(3-(3,4,5-trimethoxybenzoyl)guanidino)phenyl)biphenyl-4-carboxamide:

(Compound 34)

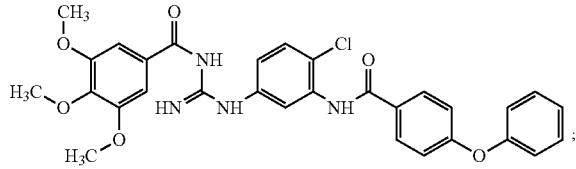

N-(4-methyl-3-(3-(3,4,5-trimethoxybenzoyl)guanidino)phenyl)biphenyl-4-carboxamide:

(Compound 35)

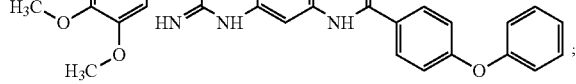

N—(N-(3-benzamidophenyl)carbamimidoyl)benzamide:

(Compound 36)

N—(N-(3-(3-biphenyl-4-ylureido)phenyl)carbamimidoyl)-3,4,5-trimethoxybenzamide:

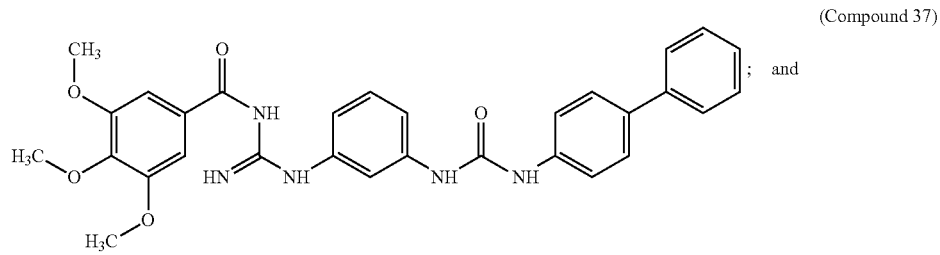 [SMILES: COc1cc(C(=O)NC(=N)Nc2cccc(NC(=O)Nc3ccc(-c4ccccc4)cc3)c2)cc(OC)c1OC]

(Compound 37)

; and

N—(N-(4-chloro-3-(3-phenylureido)phenyl)carbamimidoyl)-3,4,5-trimethoxybenzamide:

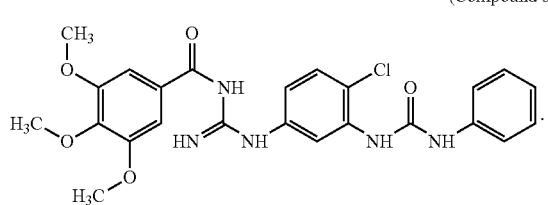

(Compound 38)

24. The compounds as claimed in claim 23, wherein the compounds are chosen from:
- 3,4,5-trimethoxy-N—(N-(3-(4-methoxybenzamido)phenyl)carbamimidoyl)benzamide (Compound 1);
- N—(N-(3-(2-chlorobenzamido)phenyl)carbamimidoyl)-3,4,5-trimethoxybenzamide (Compound 2);
- 3,4,5-trimethoxy-N—(N-(3-(3-methoxybenzamido)phenyl)carbamimidoyl)benzamide (Compound 3);
- N-(3-(3-(3,4,5-trimethoxybenzoyl)guanidino)phenyl)-2-naphthamide (Compound 6);
- N-(3-(3-(3,4,5-trimethoxybenzoyl)guanidino)phenyl)furan-2-carboxamide (Compound 8);
- N—(N-(3-benzamidophenyl)carbamimidoyl)-3,5-dimethoxybenzamide (Compound 9);
- N—(N-(3-benzamidophenyl)carbamimidoyl)-7-methoxybenzo[d][1,3]dioxole-5-carboxamide (Compound 12);
- N—(N-(3-benzamidophenyl)carbamimidoyl)-2,4-dimethoxybenzamide (Compound 13);
- N—(N-(3-benzamidophenyl)carbamimidoyl)-3,4,5-trimethoxybenzamide (Compound 15);
- N-(2-chloro-5-(3-(3,4,5-trimethoxybenzoyl)guanidino)phenyl)biphenyl-4-carboxamide (Compound 17);
- N—(N-(3-(1H-indol-2-yl)phenyl)carbamimidoyl)-3,4,5-trimethoxybenzamide (Compound 19);
- N—(N-(4-chloro-3-(phenylcarbamoyl)phenyl)carbamimidoyl)-3,4,5-trimethoxybenzamide (Compound 21);
- 4'-fluoro-N-(3-(3-(3,4,5-trimethoxybenzoyl)guanidino)phenyl)biphenyl-4-carboxamide (Compound 23);
- N-(2-methyl-5-(3-(3,4,5-trimethoxybenzoyl)guanidino)phenyl)biphenyl-4-carboxamide (Compound 24);
- N—(N-(3-(1H-indol-1-yl)phenyl)carbamimidoyl)-3,4,5-trimethoxybenzamide (Compound 29);
- 4'-fluoro-N-(2-methyl-5-(3-(3,4,5-trimethoxybenzoyl)guanidino)phenyl)biphenyl-4-carboxamide (Compound 30);
- N—(N-(4-chloro-3-(4-phenoxybenzamido)phenyl)carbamimidoyl)-3,4,5-trimethoxybenzamide (Compound 32);
- N—(N-(4-chloro-3-(3-phenylureido)phenyl)carbamimidoyl)-3,4,5-trimethoxybenzamide (Compound 38).

25. The compounds of formula (I) as claimed in claim 20, wherein the compounds are in the form of salts.

26. The compounds of formula (I) as claimed in claim 25, wherein said salts are formed with hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkanesulfonic acids, arylsulfonic acids, or arylcarboxylic acids.

27. The compounds of formula (I) as claimed in claim 26, wherein said salts are formed with hydrochloric acid.

* * * * *

UNITED STATES PATENT AND TRADEMARK OFFICE
CERTIFICATE OF CORRECTION

PATENT NO.      : 8,889,678 B2
APPLICATION NO. : 13/386782
DATED           : November 18, 2014
INVENTOR(S)     : Ruat et al.

It is certified that error appears in the above-identified patent and that said Letters Patent is hereby corrected as shown below:

In the Claims

Column 46,
Lines 41-49, the formula for Compound 20 should appear as follows:

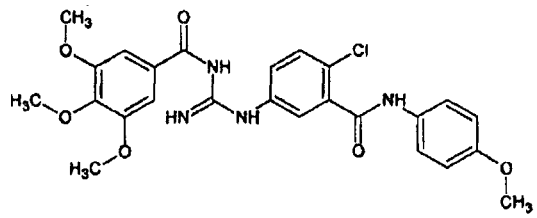

Column 59,
Line 45, "(Compound 91)" should read --(Compound 31)--.

Signed and Sealed this
Seventh Day of April, 2015

Michelle K. Lee
*Director of the United States Patent and Trademark Office*